United States Patent
Sung et al.

(10) Patent No.: US 9,737,518 B2
(45) Date of Patent: *Aug. 22, 2017

(54) TIOTROPIUM DRY POWDERS

(71) Applicant: Pulmatrix, Inc., Lexington, MA (US)

(72) Inventors: Jean C. Sung, Cambridge, MA (US); Diana Manzanedo, Cambridge, MA (US); Jason M. Perry, Cambridge, MA (US); Wesley Dehaan, Chelmsford, MA (US); Brian Trautman, Arlington, MA (US)

(73) Assignee: Pulmatrix Operating Company, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/870,736

(22) Filed: Sep. 30, 2015

(65) Prior Publication Data

US 2016/0120855 A1 May 5, 2016

Related U.S. Application Data

(63) Continuation of application No. PCT/US2014/025660, filed on Mar. 13, 2014.

(60) Provisional application No. 61/807,063, filed on Apr. 1, 2013, provisional application No. 61/874,146, filed on Sep. 5, 2013, provisional application No. 61/925,400, filed on Jan. 9, 2014.

(51) Int. Cl.
| | |
|---|---|
| *A61K 31/05* | (2006.01) |
| *A61K 31/4745* | (2006.01) |
| *A61K 31/56* | (2006.01) |
| *A61K 9/00* | (2006.01) |
| *A61K 31/439* | (2006.01) |
| *A61K 9/16* | (2006.01) |
| *A61K 45/06* | (2006.01) |
| *A61K 31/58* | (2006.01) |
| *A61K 31/57* | (2006.01) |

(52) U.S. Cl.
CPC .......... *A61K 31/439* (2013.01); *A61K 9/0075* (2013.01); *A61K 9/1611* (2013.01); *A61K 9/1617* (2013.01); *A61K 31/57* (2013.01); *A61K 31/58* (2013.01); *A61K 45/06* (2013.01)

(58) Field of Classification Search
CPC .. A61K 31/439; A61K 9/0075; A61K 9/1611; A61K 9/1617; A61K 31/58; A61K 31/57; A61K 45/06
See application file for complete search history.

(56) References Cited

U.S. PATENT DOCUMENTS

| | | |
|---|---|---|
| 3,861,386 A | 1/1975 | Harris et al. |
| 4,085,893 A | 4/1978 | Durley, III |
| 4,193,009 A | 3/1980 | Durley, III |
| 4,233,405 A | 11/1980 | Neubeck |
| 4,238,425 A | 12/1980 | Matsuoka et al. |
| 4,637,815 A | 1/1987 | Lemole |
| 4,643,351 A | 2/1987 | Fukamachi et al. |
| 4,828,844 A | 5/1989 | Rontgen-Odenthal et al. |
| 4,881,541 A | 11/1989 | Eger, II et al. |
| 4,921,639 A | 5/1990 | Chiu |
| 5,063,922 A | 11/1991 | Hakkinen |
| 5,175,152 A | 12/1992 | Singh |
| 5,230,884 A | 7/1993 | Evans et al. |
| 5,466,680 A | 11/1995 | Rudy |
| 5,514,665 A | 5/1996 | Speert et al. |
| 5,551,416 A | 9/1996 | Stimpson et al. |
| 5,571,535 A | 11/1996 | Flowers et al. |
| 5,612,053 A | 3/1997 | Baichwal et al. |
| 5,633,003 A | 5/1997 | Cantor |
| 5,654,007 A | 8/1997 | Johnson et al. |
| 5,709,202 A | 1/1998 | Lloyd et al. |
| 5,785,049 A | 7/1998 | Smith et al. |

(Continued)

FOREIGN PATENT DOCUMENTS

| | | |
|---|---|---|
| CN | 1240349 | 1/2000 |
| CN | 1446877 | 10/2003 |

(Continued)

OTHER PUBLICATIONS

Adi, et al., "Agglomerate strength and dispersion of pharmaceutical powders," Journal of Aerosol Science, 42:285-294, 2011.

(Continued)

*Primary Examiner* — Mina Haghighatian
(74) *Attorney, Agent, or Firm* — McDermott, Will & Emery LLP

(57) ABSTRACT

The present invention relates to respirable dry powder comprising respirable dry particles that comprise sodium chloride, leucine, and tiotropium bromide, wherein the sodium chloride is about 60% to about 90%, the leucine is about 10% to about 40%, the tiotropium bromide is about 0.01% to about 0.5%, and optionally one or more additional therapeutic agents up to about 20%, wherein all percentages are weight percentages on a dry basis and all the components of the respirable dry particles amount to 100%. The invention also relates to respirable dry powders that contain respirable dry particles that comprise sodium chloride, leucine, and tiotropium bromide, wherein the sodium chloride is 67% to 84%, the leucine is 12% to 28%, the tiotropium bromide is about 0.01% to about 0.5%, and optionally one or more additional therapeutic agents up to about 20%, wherein all percentages are weight percentages on a dry basis and all the components of the respirable dry particles amount to 100%. The invention also relates to respirable dry powders that contain respirable dry particles that comprise about 79.5% to about 80.5% (w/w) sodium chloride, about 19.5% to about 20.5% (w/w) leucine, and about 0.01% to about 0.5% (w/w) tiotropium bromide, and methods for treating a subject using the respirable dry powders.

23 Claims, 11 Drawing Sheets

(56) References Cited

U.S. PATENT DOCUMENTS

| | | |
|---|---|---|
| 5,817,028 A | 10/1998 | Anderson |
| 5,855,913 A | 1/1999 | Hanes et al. |
| 5,883,084 A | 3/1999 | Peterson et al. |
| 5,898,037 A | 4/1999 | Marx |
| 5,981,559 A | 11/1999 | Nagaoka et al. |
| 5,985,309 A | 11/1999 | Edwards et al. |
| 6,083,922 A | 7/2000 | Montgomery |
| 6,165,463 A | 12/2000 | Platz et al. |
| RE37,053 E | 2/2001 | Hanes et al. |
| 6,214,536 B1 | 4/2001 | Boucher |
| 6,254,854 B1 | 7/2001 | Edwards et al. |
| 6,339,075 B1 | 1/2002 | King et al. |
| 6,428,814 B1 | 8/2002 | Bosch et al. |
| 6,447,752 B2 | 9/2002 | Edwards et al. |
| 6,451,352 B1 | 9/2002 | Yvin et al. |
| 6,475,523 B1 | 11/2002 | Staniforth |
| 6,511,050 B2 | 1/2003 | Chu |
| 6,546,927 B2 | 4/2003 | Litherland et al. |
| 6,572,849 B2 | 6/2003 | Shahinian, Jr. |
| 6,582,728 B1 | 6/2003 | Platz et al. |
| 6,608,055 B2 | 8/2003 | Sieger et al. |
| 6,613,308 B2 | 9/2003 | Bartus et al. |
| 6,635,283 B2 | 10/2003 | Edwards et al. |
| 6,669,959 B1 | 12/2003 | Adjei et al. |
| 6,732,732 B2 | 5/2004 | Edwards et al. |
| 6,749,835 B1 | 6/2004 | Lipp et al. |
| 6,793,205 B2 | 9/2004 | Eom |
| 6,830,764 B2 | 12/2004 | Inui et al. |
| 6,851,626 B2 | 2/2005 | Patel et al. |
| 6,962,151 B1 | 11/2005 | Knoch et al. |
| 6,989,155 B1 | 1/2006 | Ganderton et al. |
| 7,008,644 B2 | 3/2006 | Batycky et al. |
| 7,112,572 B2 | 9/2006 | Deadman et al. |
| 7,182,961 B2 | 2/2007 | Batycky et al. |
| 7,192,919 B2 | 3/2007 | Tzannis et al. |
| 7,195,179 B2 | 3/2007 | Miller et al. |
| 7,306,787 B2 | 12/2007 | Tarara et al. |
| 7,384,649 B2 | 6/2008 | Batycky et al. |
| 7,556,798 B2 | 7/2009 | Edwards et al. |
| 7,575,761 B2 | 8/2009 | Bennett et al. |
| 7,838,532 B2 | 11/2010 | Surber et al. |
| 7,879,358 B2 | 2/2011 | Jackson et al. |
| 7,968,717 B2 | 6/2011 | Pfrengle et al. |
| 8,187,637 B2 | 5/2012 | Edwards et al. |
| 8,303,991 B2 | 11/2012 | Staniforth et al. |
| 8,591,866 B2 | 11/2013 | Edwards et al. |
| 8,759,369 B2 | 6/2014 | Zeng |
| 2001/0008632 A1 | 7/2001 | Freund et al. |
| 2001/0038858 A1 | 11/2001 | Roser et al. |
| 2002/0034477 A1 | 3/2002 | Edwards et al. |
| 2002/0056449 A1 | 5/2002 | Wakefield et al. |
| 2002/0129812 A1 | 9/2002 | Litherland et al. |
| 2002/0177562 A1 | 11/2002 | Weickert et al. |
| 2003/0055034 A1 | 3/2003 | Montgomery |
| 2003/0068280 A1 | 4/2003 | Bannister et al. |
| 2003/0129139 A1 | 7/2003 | Batycky et al. |
| 2003/0129141 A1 | 7/2003 | Platz et al. |
| 2003/0138403 A1 | 7/2003 | Drustrup |
| 2003/0146300 A1 | 8/2003 | Denyer et al. |
| 2003/0186894 A1 | 10/2003 | Kuo et al. |
| 2003/0203930 A1 | 10/2003 | Chaudry et al. |
| 2003/0232019 A1 | 12/2003 | Basu et al. |
| 2004/0009128 A1 | 1/2004 | Rabinowitz et al. |
| 2004/0047810 A1 | 3/2004 | Staniforth et al. |
| 2004/0076589 A1 | 4/2004 | Edwards et al. |
| 2004/0081627 A1 | 4/2004 | Jinks et al. |
| 2004/0105821 A1 | 6/2004 | Bernstein et al. |
| 2004/0256487 A1 | 12/2004 | Collins et al. |
| 2005/0004020 A1 | 1/2005 | Yu et al. |
| 2005/0054682 A1 | 3/2005 | Phillips |
| 2005/0123509 A1 | 6/2005 | Lehrman et al. |
| 2005/0211244 A1 | 9/2005 | Nilsson et al. |
| 2005/0220720 A1 | 10/2005 | Edwards et al. |
| 2005/0247306 A1 | 11/2005 | Harvey et al. |
| 2005/0247312 A1 | 11/2005 | Davies |
| 2005/0255049 A1 | 11/2005 | Slowey et al. |
| 2005/0271660 A1 | 12/2005 | Wang |
| 2005/0274378 A1 | 12/2005 | Bonney et al. |
| 2005/0276845 A1 | 12/2005 | Roser et al. |
| 2005/0279349 A1 | 12/2005 | Patton et al. |
| 2005/0281740 A1 | 12/2005 | Gong et al. |
| 2006/0073173 A1 | 4/2006 | Banach et al. |
| 2006/0142208 A1 | 6/2006 | Boucher |
| 2006/0147520 A1 | 7/2006 | Ruegg |
| 2006/0276483 A1 | 12/2006 | Surber et al. |
| 2007/0092535 A1 | 4/2007 | Watts |
| 2007/0104657 A1 | 5/2007 | Batycky et al. |
| 2007/0105086 A1 | 5/2007 | Qin et al. |
| 2007/0110678 A1 | 5/2007 | Zierenberg et al. |
| 2007/0202051 A1 | 8/2007 | Schuschnig |
| 2007/0270502 A1 | 11/2007 | Edwards et al. |
| 2007/0275091 A1 | 11/2007 | King et al. |
| 2007/0292454 A1 | 12/2007 | Bell et al. |
| 2008/0004247 A1* | 1/2008 | Lindmark ............ A61K 31/165 514/171 |
| 2008/0038207 A1 | 2/2008 | Edwards et al. |
| 2008/0063722 A1 | 3/2008 | Ward et al. |
| 2008/0127972 A1 | 6/2008 | Morton |
| 2008/0190424 A1 | 8/2008 | Lucking et al. |
| 2009/0192187 A1 | 7/2009 | Brambilla et al. |
| 2009/0208999 A1 | 8/2009 | Groenendaal et al. |
| 2009/0232744 A1 | 9/2009 | Keller et al. |
| 2009/0285905 A1 | 11/2009 | Gordon et al. |
| 2010/0136121 A1 | 6/2010 | Sanders |
| 2010/0150994 A1 | 6/2010 | Kotyla |
| 2010/0159007 A1 | 6/2010 | Staniforth |
| 2010/0226990 A1 | 9/2010 | Healy et al. |
| 2010/0285142 A1 | 11/2010 | Staniforth et al. |
| 2010/0326437 A1 | 12/2010 | Zeng |
| 2011/0023876 A1 | 2/2011 | Vehring et al. |
| 2011/0192397 A1 | 8/2011 | Saskar et al. |
| 2011/0236492 A1 | 9/2011 | Morton |
| 2011/0311618 A1 | 12/2011 | Amighi et al. |
| 2012/0070417 A1 | 3/2012 | Batycky |
| 2012/0101077 A1 | 4/2012 | Pandy et al. |
| 2012/0107414 A1 | 5/2012 | Lipp |
| 2012/0132204 A1 | 5/2012 | Lucking et al. |
| 2012/0135969 A1 | 5/2012 | Weiler et al. |
| 2013/0004542 A1 | 1/2013 | Martyn |
| 2013/0266653 A1* | 10/2013 | Lipp ................ A61K 9/0075 424/489 |

FOREIGN PATENT DOCUMENTS

| | | |
|---|---|---|
| CN | 1694689 A | 11/2005 |
| CN | 101106975 | 1/2008 |
| EP | 0367723 | 5/1990 |
| EP | 0652011 | 5/1995 |
| EP | 0681833 | 11/1995 |
| EP | 1142600 | 10/2001 |
| EP | 1466610 | 10/2004 |
| EP | 1709961 | 10/2006 |
| EP | 2050437 A1 | 4/2009 |
| JP | 05123398 | 5/1993 |
| KR | 1020050056622 | 6/2005 |
| KR | 1020070104657 | 10/2007 |
| NZ | 328476 | 5/1999 |
| NZ | 305168 | 8/1999 |
| NZ | 530123 | 1/2007 |
| WO | 9206695 | 4/1992 |
| WO | 9612470 | 5/1996 |
| WO | 9631221 | 10/1996 |
| WO | 9736574 | 10/1997 |
| WO | 9744013 | 11/1997 |
| WO | 98/16205 | 4/1998 |
| WO | 9848875 A1 | 11/1998 |
| WO | 9951096 | 10/1999 |
| WO | 9964014 | 12/1999 |
| WO | 0013677 | 3/2000 |
| WO | 0066206 | 11/2000 |
| WO | 0113892 | 3/2001 |
| WO | 0176610 A1 | 3/2001 |
| WO | 0185136 | 11/2001 |
| WO | 0185137 | 11/2001 |

(56) References Cited

FOREIGN PATENT DOCUMENTS

| WO | 0195874 | 12/2001 |
|---|---|---|
| WO | 0205730 A1 | 1/2002 |
| WO | 0209574 | 2/2002 |
| WO | 02060468 A2 | 8/2002 |
| WO | 02083079 | 10/2002 |
| WO | 03035028 A1 | 1/2003 |
| WO | 03/035028 | 5/2003 |
| WO | 03043585 | 5/2003 |
| WO | WO03/035028 | 5/2003 |
| WO | WO03043585 | 5/2003 |
| WO | 03103632 | 12/2003 |
| WO | 2004002551 | 1/2004 |
| WO | 2004/030659 A1 | 4/2004 |
| WO | 2004030659 A1 | 4/2004 |
| WO | 2004030659 A1 | 4/2004 |
| WO | 2004096204 | 11/2004 |
| WO | 2005004852 | 1/2005 |
| WO | 2005041921 | 5/2005 |
| WO | 2005041922 | 5/2005 |
| WO | 2005092289 | 10/2005 |
| WO | 2006029209 A2 | 3/2006 |
| WO | 2006038070 B2 | 4/2006 |
| WO | 2006084131 A2 | 8/2006 |
| WO | 2006102438 | 9/2006 |
| WO | 2006/125153 | 11/2006 |
| WO | 2006125153 A2 | 11/2006 |
| WO | WO2006/125153 | 11/2006 |
| WO | 2007057714 | 5/2007 |
| WO | 2007057714 A2 | 5/2007 |
| WO | WO2007/057714 | 5/2007 |
| WO | 2008062429 | 5/2008 |
| WO | 2008025560 | 6/2008 |
| WO | 2008065666 A2 | 6/2008 |
| WO | 2009/037503 | 3/2009 |
| WO | 2009037503 | 3/2009 |
| WO | 2009037503 A2 | 3/2009 |
| WO | 2009044141 A1 | 4/2009 |
| WO | 2009130560 A1 | 10/2009 |
| WO | 2009/140587 | 11/2009 |
| WO | 2009140587 | 11/2009 |
| WO | 2009140587 A1 | 11/2009 |
| WO | 2010/111680 | 9/2010 |
| WO | 2010110760 | 9/2010 |
| WO | 2010111640 | 9/2010 |
| WO | 2010111641 | 9/2010 |
| WO | 2010111644 | 9/2010 |
| WO | 2010111650 | 9/2010 |
| WO | 2010111680 A2 | 9/2010 |
| WO | WO2010/111680 | 9/2010 |
| WO | 2011006073 A1 | 1/2011 |
| WO | 2011037549 | 3/2011 |
| WO | 2011048379 | 4/2011 |
| WO | 2012030645 | 3/2012 |
| WO | 2012030647 | 3/2012 |
| WO | 2012030664 | 3/2012 |
| WO | 2012051426 | 4/2012 |
| WO | WO2012044736 A1 | 4/2012 |
| WO | 2013/104892 | 7/2013 |
| WO | 2013104892 | 7/2013 |
| WO | 2013104892 A1 | 7/2013 |

OTHER PUBLICATIONS

Adjei and Garren, "Pulmonary delivery of peptide drugs: effect of partical size on bioavailability of leuprolide acetate in healthy male volunteers", J.Pharm. Res., 7:565-569 (1990).
Aldrich Catalog pp. 1502, 1998-1999.
Anderson, et al., "Effect of cystic fibrosis on inhaled aerosol boluses" Am. Rev. Respir. Dis., 140: 1317-1324 (1989).
Bergeron, et al., "Controlling droplet deposition with polymer additives" Nature. 405:772-775 (2000).
Boren, "The development of a molecular model of lung" Arch Intern Med 126(3):491-495 (1970).

Broadhead, et al., The Spray Drying of Pharmaceuticals, Drug Development and Industrial Pharmacy, 18 (11&12):1169-1206, 1992.
Bromberg and Klibanov, "Transport of proteins dissolved in organic solvents across biomimetic membranes", Proc. Natl. Acad. Sci. USA, 92(5):1262-6 (1995).
Bucca, C. and G. Rolla, "Nebulised magnesium in asthma: the right solution for an old remedy?" The Lancet, 361:2095-2096 (2003).
Burg, et al., "Cellular Response to Hyperosmotic Stresses," Am. Physiological Soc., 87:1441-1474 (2007).
Cataldo, et al., "Induced sputum: comparison between isotonic and hypertonic saline solution inhalation in patients with asthma" Chest, 120(6):1815-21 (2001).
Chan, H., "Spray Dried Powders and Powder Blends of Recombinant Human Deoxyribonuclease (rhDNase) for Aerosol Delivery," Pharmaceutical Research, 14(4): 431-437, 1997.
Chiou, et al., "A novel production method for inhalable cyclosporine A powders by confined liquid impinging jet precipitation," Journal of Aerosol Science, 39:500-509, 2008.
Choi, et al., "Inhalation delivery of proteins from ethanol suspensions" Proc. Natl. Acad. Sci. 98:11103-11107 (2001).
Clarke, et al., "Resistance to two-phase-gas-liquid flow in airways" J. Appl. Physiol.29(4):464-471 (1970).
Copp, et al., "Hypertonic Shock Inhibits Growth Factor Receptor Signaling, Induces Caspase-3 Activation, and Causes Reversible Fragmentation of the Mitocholdrial Network," Am. J. Physiol, 288:C403-C415 (2005).
Costello, B., et al., "Use of the Du Nouy Ring with a Rotational Rheometer to Measure Interfacial Rheology Properties", Annual Transactions of The Nordic Rheology Society. 2006, 14.
Crowder, et al., "2001: An Odyssey in Inhaler Formulation and Design," Pharmaceutical Technology, 99-113, Jul. 2001.
Davis, et al., "Charged Polymers Modulate Retrovirus Transduction via Membrane Charge Neutralization and Virus Aggregation", Biophys J,86:1234-1242 (2004).
Dawson, et al., "Enhanced viscoelasticity of human cystic fibrotic sputum correlates with increasing microheterogeneity in particle transport", J. of Biol. Chem., 278(50):50393-50401 (2003).
Denn, M.M., "Viscoelasticity", In Process Fluid Mechanics, Prentice-Hall, Englewood Cliffs, New Jersey, pp. 358-373 (1980).
Edwards, et al., "Inhaling to mitigate exhaled bioaerosols," PNAS (2004), vol. 101, pp. 17383-17388.

Edwards, "The macrotransport of aerosol particles in the lung: aerosol deposition phenomena" J. Aerosol Sci., 26:293-317 (1995).

Edwards, et al., "Novel Inhalents for Control and Protection Against Airborne Infections," Respiratory Drug Delivery, 2006, pp. 41-48.

Eng Pa, et al., "Short-term efficacy of ultrasonically nebulized hypertonic saline in cystic fibrosis," Pediatr. Pulmonol., 21:77-83 (1996).

European Search Report from EP Appl. No. 11177874 dated Nov. 21, 2011.

Evrensel, et al., "Viscous airflow through a rigid tube with compliant lining: A simple model for the air-mucus interaction in pulmonary pathways", J.Biomech. Eng., 115:262-267 (1993).

Feng, et al., "Improved clearability of cystic fibrosis sputum with dextran treatment in vitro," Am. J. Respir. Crit. Care Med., 157(3):710-714 (1998).

Ferguson, et al., "Transmission intensity and impact of control policies on the foot and mouth epidemic in Great Britain", Nature, 414(6861):329 (2001).

Fiegel et al., "Airborne Infectious Disease and the Suppression of Pulmonary Bioaerolsols," DDT, Jan. 2006, 11 (1/2), pp. 51-57.

French, et al., "The influence of formulation on emission, deaggregation and deposition of dry powders for inhalation", J. Aerosol Sci., 27:769-783 (1996).

Friedmen, et al. "A Randomized, Prospective, Double-Blind Study on the Efficacy of Dead Sea Salt Nasal Irrigations," The Laryngoscope, 2006, pp. 878-882, 116.

Fuge, et al., "The geochemistry of iodine—a review", Environmental Geochemistry and Health, 8(2):31-54 (1986).

Gad-El-Hak, et al., "On the interaction of compliant coatings with boundary layer flows", J. Fluid Mech., 140:257-280 (1984).

(56) References Cited

OTHER PUBLICATIONS

Ganderton, "The generation of respirable clouds from coarse powder aggregates", Biopharmaceutical Sciences,3:101-105 (1992).
Geller, et al., "Development of a DPI Tobramycin Formulation using Pulmosphere Technology," J. of Aerosol Medicine and Pulmonary Drug Delivery, 24:175-182, 2011.
Ghoroi, et al., "A novel production method for inhalable cyclosporine A powders by confined liquid impinging jet precipitation," 85:11-24, 2013.
Goldberg, et al., "Mechanism of enhancement of microbial cell hydrophobicity by cationic polymers", J. Bacteriology, 172:5650-5654 (1990).
Gonda, "Aerosols for delivery of therapeutic and diagnostic agents to the respiratory tract", Critical Reviews in Therapeutic Drug Carrier Systems, 6:273-313 (1990).
Guo-Zhong Tao, et al., "Hyposmotic Stress Induces Cell Growth Arrest Via Proteasome Activation and Cyclin/Cyclin-Dependent Kinase Degradation," J. Biological Chemistry, 277(22): 19295-19303 (2002).
Hardy, et al. "Sensitivity of aerosol bolus behavior to methacholine-induced bronchoconstriction", Chest, 114 (2):404-10 (1998).
Hatch, G.E., "Comparative Biochemistry of Airway Lining Fluid," In: Parent, R.A., Ed., Treatise on Pulmonary Toxicology, vol. 1: Comparative Biology of the Normal Lung, CRC Press, Boca Raton, Florida (1992).
Hawley's Condensed Chemical Dictionary, 14th edition John Wiley & Sons, 2001, pp. 161 and 977.
Heyder J., et al., "Deposition of particles in the human respiratory tract in the size range 0.005-15µm" J. Aerosol Sci., 17:811-825 (1986).
Hirschman, et al., "Inhibition of human immunodeficiency virus type 1 replication by nonionic block polymer surfactants" J. Med. Virol. 42(3):249-54 (1994).
Hsu, et al., "Role of Viscoelasticity in Tube Model of Airway Reopening. I. Nonnewtonian Sols.", J. Appl Physiol. 76 (6):2481-2489 (1994).
Im, et al., "In vivo determination of surface tension in the horse trachea and in vitro model studies", Respir. Physiol., 109:81-93 (1997).
Iwasaki, et al., "Exacerbation of influenzavirus pneumonia by intranasal administration of surfactant in a mouse model" Arch. Virol., 144:675-685 (1999).
Jaffari, et al., "Rapid characterisation of the inherent dispersibility of respirable powders using dry dispersion laser diffraction," International Journal of Pharmaceuticals, 447:124-131, 2013.
Tansey, "The challenges in the development of metered dose inhalation aerosols using ozone-friendly propellants" Spray Technol. Market. 4:26-29 (1994).
Tibby, et al., "Exogenous surfactant supplementation in infants with respiratory syncytial virus bronciolitis" Am J Respir Crit Care Med., 162(4 Pt 1):1251 (2000).
Timsina, et al., Drug Delivery to the respiratory tract using dry powder inhalers Int. J. Pharm., 101:1-13 (1995).
Tsurumi et al., "Effect of high salt treatment on influenza B viral protein synthesis in MDCK cells," Microbiology and immunology, 1983, 27(6), pp. 519-529 (Full document).
Ulcerative Colitis: Inflammatory Bowel Disease (n. d.) retrieved from http://adam.about.com/reports/000069_1.htm.
Vehring, "Pharmaceutical Particle Engineering via Spray Drying" Pharma. Res., vol. 25, No. 5, May 2008.
Vinnikov, et al., "Aerosol Inhalations of Calcium Chloride in Combination Therapy of Pulmonary Tuberculosis," Kazanskii Meditsinskii Zhurnal (1962), vol. 4, pp. 7-9 (translation included).
Visser, "Van der Waals and other cohesive forces affecting powder fluidization", Powder Technology, 58:1-10 (1989).
Vollenbroich, et al., "Mechanism of inactivation of enveloped viruses by the biosurfactin from *Bacillus subtilis*" Biologicals, 25(3):289-97 (1997).
Wade, C.E., "Hypertonic saline resuscitation in sepsis," Critical Care, Oct. 2002, 6(5), 397-398.
Wark, Rab, McDonald V. Nebulized hypertonic saline for cystic fibrosis (Cochrane Review). In: The Cochrane Library. Oxford, UK: Update Software, 2005.
Watanabe et al., "Why Inhaling Salt Water Changes What We Exhale," Journal of Colloid and Interface Science, 307, pp. 71-78 (2007).
Watanabe, et al., "Immunogenicity and protective efficacy of replication-incompetent influenza virus-like particles" Journal of Virology 76(2):767-773 (2002).
Wikipedia, "Hypertonic" Wikipedia, 2006, accessed Nov. 21, 2006 (en.wikipedia.org/wiki/Hypertonic).
Williams, "Portal to the interior: viral pathogenesis and natural compounds that restore mucosal immunity and modulate inflammation", Alternative Medicine Review, 8(4):395-409 (2003).
Zanen and Lamm, "The optimal particle size for parasymathicolytic aerosols in mild asthmatics", J. Int. J. Pharm., 114:111-115 (1995).
Zasadzinski, et al., "The physics and physiology of lung surfactants", Current Opinion in Colloid & Interface Science, 6:506-513 (2001).
Zayas, et al., "A new paradigm in respiratory hygiene: modulating respiratory secretions to contain cough bioaerosol without affecting mucus clearance," BMC Pulm. Med., 11 (2007).
Shur, Jagdeep, et al., "Cospray-Dried Unfractionated Heparin With L-Leucine as a Dry Powder Inhaler Mucolytic for Cystic Fibrosis Therapy," J. Pharm Sci., 97:4857-4868 (2008).
Arold, et al., "Efficacy of Fluticasone and Salmeterol in a Novel Dry Powder Delivery Platform," ATS 2011 Meeting, Abstract #C22 (May 15, 2011).
Arold, et al., "A Novel Inhaled Dry Powder Delivery Platform; Efficacy of Fluticasone and Salmeterol during Allergic Asthma," ISAM 2011 Meeting, Poster (Apr. 6, 2011).
Arold, et al., "A Novel Inhaled Dry Powder Delivery Platform; Efficacy of Fluticasone and Salmeterol during Allergic Asthma," ISAM 2011 Meeting, Abstract (Apr. 6, 2011).
Sung, "A Novel Platform for DP Inhalation Drugs," 2011 Manufacturing Chemist J article Nov. 7, 2011, accessed online on Jan. 11, 2013.
Arold, et al., "iSPERSE: A Novel Inhaled Dry Powder Delivery Platform for the Delivery of Large Molecule Drugs to the Lung for Local and Systemic Treatments," ATS 2012 Meeting, Abstract (May 18, 2012).
Sung, et al., "Pulmonary Delivery of Combination Drug Products via a Novel Dry Powder Delivery Technology," US-Japan Drug Delivery Symposium 2011, Abstract (Dec. 16, 2011).
Sung, et al., "Pulmonary Delivery of Combination Drug Products via a Novel Dry Powder Delivery Technology," US-Japan Drug Delivery Symposium 2011, Poster (Dec. 16, 2011).
Manzanedo, et al., "Formulation Characterization of a Novel Levofloxacin Pulmonary Dry Powder Drug Delivery Technology," RDD 2012 Meeting, Abstract (May 13, 2012).
Manzanedo, et al., "Formulation Characterization of a Novel Levofloxacin Pulmonary Dry Powder Drug Delivery Technology," RDD 2012 Meeting, Poster (May 13, 2012).
Lawlor, et al., "Development of iSPERSE™ Based Platform for the Delivery of Macromolecules via Dry Powder Formulations," RDD 2012 Meeting, Abstract (May 13, 2012).
Lawlor, et al., "Development of iSPERSE™ Based Platform for the Delivery of Macromolecules via Dry Powder Formulations," RDD 2012 Meeting, Poster (May 13, 2012).
Manzanedo, et al., "Novel Respiratory Dry Powder Drug Delivery Technology for High Drug Load LABA/LAMA," AAPS 2012 Meeting, Abstract (May 21, 2012).
Sung, "A Next-Generation Inhaled Dry Powder Delivery Platform," Drug Development & Delivery, Jul./Aug. 2012, journal article.
Sung, ""New Formulation Expands Potential for Pulmonary and Systemic Therapies,"" Pharmaceutical Formulation & Quality (PFQ), Dec. 2011/Jan. 2012, Journal Article, accessed online Jan. 11, 2013.
Lawlor, "A High Load Macromolecule Delivery Platform for Pulmonary Dry Powder Drug Delivery," AAPS 2012 Meeting, Poster (May 21, 2012).

(56) References Cited

OTHER PUBLICATIONS

Edwards, et al., "Novel Inhalants for Control and Protection Against Airborne Infections," RDD 2006 Meeting, Abstract, (Apr. 23, 2006).
Sung, et al., "iSPERSE™: Formulation and In Vitro Characterization of a Novel Dry Powder Drug Delivery Technology," RDD Europe 2011 Meeting, Abstract, (May 3, 2011).
Sung, et al., "iSPERSE™: Formulation and In Vitro Characterization of a Novel Dry Powder Drug Delivery Technology," RDD Europe 2011 Meeting, Poster (May 3, 2011).
International Search Report dated Dec. 14, 2011 from PCT Application No. PCT/US2011/053829.
Kaye, et al., "Simultaneously Manufactured Nano-In-Micro(SIMANIM) Particles for Dry-Powder Modified-ReleaseDelivery of Antibodies," Pharmaceutics, Preformulations and Drug Delivery, 98:11:4055-4068, 2009.
Kilpatrick, et al., "Calcium Chloride and Adrenaline as Bronchial Dilators Compared by Sequential Analysis," British Medical Journal (1954), pp. 1388-1391.
King, "Rheology of cystic fibrosis sputum after in vitro treatment with hypertonic saline alone and in combination with recombinant human deoxyribonuclease I" Am. J. Respir. Crit. Care Med., 156(1):173-7 (1997).
King and Tarsitamo, "The effect of structured and unstructured pre-operative teaching: a replication", Nurs. Res., 31(6):324-9 (1982).
King, et al., "The role of mucus gel viscosity, spinnability, and adhesive properties in clearance by simulated cough", Biorheology, 26:737-745 (1989).
King, M., et al., "Mucomodulator Therapy in Cystic Fibrosis: Balancing Mucus Clearability Against the Spread of Airborne Pathogens," Pediatric Pulmonolgy, 2004, pp. 77-79, Supp. 26.
Kirkness, et al., "Decreased surface tension of upper airway mucosal lining liquid increases upper airway patency in anaesthetised rabbits", J. Physiol., 547(Pt 2):603-11(2003).
Kurashima, et al., "A pilot study of surfactant inhalation for the treatment of asthmatic attack" Arerugi, 40(2):160-3 (1991).
Lipp, et al., "Solving medical problems with chemical engineering", Chemtech, 42-57 (Mar. 1997).
Macosko, C.W., "Linear Viscoelasticity", in Rheology. Principles, Measurements, and Applications, Wiley-VCH, New York, pp. 109-133 (1994).
Mai, X.-M, et al., "Hypertonic saline challenge tests in the diagnosis of bronchial hyperresponsiveness and asthma in children," Pediatric Allergy & Immunology, Oct. 2002, 13(5), pp. 361-267.
Makker, et al., "Relation of hypertonic saline responsiveness of the airways to exercise induced asthma symptom severity and to histamine or methacholine reactivity," Thorax, 1993, 48, pp. 142-147.
Marriott, et al., "Changes in the Gel Properties of Tracheal Mucus Induced bu Divalent Cations," Biorheology, 1979, pp. 331-337, vol. 16.
The Merck Index, 12th edition, Merck &Co., Inc., Whitehouse Station, NJ, p. 1089. 1996, pp. 177 & 1614-1615.
Merck Manual Home Edition, "Asthma: Lung and Airway Disorders," accessed at www.merck.com/mmhe/print/sec04/ch044a/html accessed on May 5, 2010.
Merck Manual Home Edition, "Chronic Obstructive Pulmonary Disease," accessed at www.merck.com/mmhe/print/sec04/ch045a/ html accessed on Mar. 21, 2010.
Merck Manual Home Edition, "Acute Respiratory Distress Syndrome (ARDS)," accessed on Nov. 17, 2011 at www.merckmanuals. com/home/lung_and_airway_disorders/ respiratory_filure_ and_acute_respiratory_distress_syndrome/acute_respiratory_ distress_syndrome_ards.html#v727948.
The Online Merck Manual Medical Second Home Edition article, entitled, "Influenza"—accessed on Feb. 22, 2010 at www.merck. com/mmhe/print/sec17/ch198/ch198d.html.
Miller, M.J., "Assessing the use of Pharmacokinetic Models in Risk Assessments on Inhaled Toxicants", School of Public Health Sciences, Environmental Health, and Toxicology (1992).
Modler, "Calcium as an Adjuvant for Spray-Drying Acid Whey," Journal of Dairy Science, 61:294-299, 1978.
Morrison, F.A., "Introduction, How Much Do I Need to Learn about Rheology?" In Understanding Rheology, Oxford University Press, New York, pp. 1-11 (2001).
Mouro, D., et al. "Enhancement of Xcelodose Capsule-Filling Capabilities Using Roller Compaction," Pharmaceutical Technology, Feb. 2006.
Nanaumi, et al., "Properties of mixed monolayers of DPCC and viscoelasticity-giving substances", Colloids & Surfaces B: Bioinformatics, 17:167-174 (2000).
Nannini, L.J., et al., "Magnesium Sulfate as a Vehicle for Nebulized Salbutamol in Acute Asthma", Am. J. Med., 108:193-197 (2000).
Oneda, et al., "The Effect of Formulation Variables on the Dissolution and Physical Properties of Spray-Dried Microspheres Containing Organic Salts," Powder Technology, 130:377-384, 2003.
Papineni and Rosenthal, "The size distribution of droplets in the exhaled breath of healthy human subjects", J. Aerosol Med., 10(2):105-116 (1997).
Patton and Platz, "Pulmonary delivery of peptides and proteins for systemic action", Adv. Drug Del. Rev., 8:179-196 (1992).
Paul, Fundamental Immunology, Raven Press, New York, pp. 699-716, 1984.
Perry's Chemical Engineers' Handbook, 7th ed., 1997, pp. 2-10, 2-11, 2-120, 2-121.
Piret, et al., "Sodium lauryl sulfate, a microbicide effective against enveloped and nonenveloped viruses" Curr. Drug Targets. 3(1):17-30 (2002).
Rabbini, et al., "The Influence of formulation components on the aerosolisation properties of spray dried powders," J. of Controlled Release, 110:130-140, 2005.
Raynal, et al., "Calcium-dependent Protein Interactions in MUC5B Provide Reversible Cross-links in Salivary Mucus," The Journal of Biological Chemistry, Aug. 2003, pp. 28703-28710, vol. 278 (31).
Riedler, J., et al. "Inhaled hypertonic saline increases sputum expectoration in cystic fibrosis," J. Pediatr Child Health, 32:48-50 (1996).
Robinson, M., et al., "Effect of hypertonic saline amiloride, and cough on mucociliary clearance in patients with cystic fibrosis," Am J. Respir. Crit. Care Med., 153:1503-1509 (1996).
Robinson, M., et al., "Effect of increasing doses of hypertonic saline on mucociliary clearance in patients with cystic fibrosis," Thorax, 52:900-903 (1997).
Robinson, M., et al., The effect of inhaled mannitol on bronchial mucus clearance in cystic fibrosis patients: a pilot study, Eur. Respir. J., 14:678-685 (1999).
Rosenblum, E. E. ("fish." Grolier Multimedia Encyclopedia, 2006, Grolier Online, accessed Nov. 21, 2006 (gme.grolier.com/cgi-bin/ article?assetid=0106750-0).
Rote Liste Service, "Rote Liste 2002" (2002), Editor Cantor Verlag, Frankfurt/Main, XP002416908, par. [72087], par. [28005].
Rudt and Muller, "In vitro Phagocytosis Assay of Nano- and Microparticles by chemiluminescence. I. Effect of Analytical Parameters, Particle Size and Particle Concentration", J. Controlled Release, 22:263-272 (1992).
Sanders, et al., "Cystic fibrosis sputum: a barrier to the transport of nanospheres", Am J Respir Crit Care Med., 162:1905-1911 (2000).
Sarrell, et al., "Nebulized 3% Hypertonic Saline Solution Treatment in Ambulatory Children with Viral Bronchiolitis Decreases Symptoms," Chest, 2002, 122, pp. 2015-2020.
Schelling G., et al., Biophyiscal Journal, 66:134-140 (1994).
Schurch, et al., "Surfactant displaces particles toward the epithelium in airways and alveoli", Respir Physiol., 80:17-32 (1990).
Serrano, P., et al., "New Data on Pharmacological Properties and Indications of Magnesium," In New Perspectives in Magnesium Research, Springher-Verglag, London, pp. 127-139 (2007).
Seville, et al., "Spray-Dried Powders for Pulmonary Drug Delivery," Crit. Rev. in Therapeutic Drug Carrier Systems, 24(4), 307-360, 2007.

(56) References Cited

OTHER PUBLICATIONS

Shigeta, et al. "Synergistic Anti-Influenza Virua A (H1N1) Activities of PM-523 (Polyoxometalate) and Ribavarin In Vitro and In Vivo," Antimicrobial Agents & Chemotherapy, 1997, 41, pp. 1423-1427.
Suara, et al., "Effect of Zinc Salts on Respiratory Syncytial Virus Replication," Antimicrobial Agents and Chemotherapy, Mar. 2004, pp. 783-790, vol. 48 (3).
Tabata and Ikada, "Macrophage phagocytosis of biodegradable microspheres composed of L-lactic acid/glycolic acid homo- and copolymers", J. Biomed. Mater. Res., 22:837-858 (1988).
Takebayashi, et al., "Role of tachykinins in airway responses to ozone in rats" J Appl Physiol 85:442-450 (1998).
International Search Report dated Sep. 17, 2014 from corresponding PCT Application No. PCT/US2014/025660.
A.D.A.M Healthcare Center, Ulcerative Colitis: Inflammatory Bowel Disease (n.d.) Retrieved from the Internet: http://adam.about.com/reports/000069_1htm (2006).
Buck, "Defensis' Offensive Play: Exploiting a Viral Achilles' Heel," Cell Host & Microbe, vol. 3, No. 1, pp. 3-4, Jan. 17, 2008.
Everaerts, et al., "The Vanilloid Transient Receptor Potential Channel TRPV4: From Structure to Disease," Progress in Biophysics and Molecular Biology, 103:2-17, (2010).
Finlay, The Mechanics of Inhaled Pharmaceutical Aerosols, Academic Press, 143-149 (2001).
Gu, et al., "2-Aminoethoxydiphenyl Borate Stimulates Pulmonary C Neurons Via the Activation of TRPV Channels," American J. of Physiology—Lung Cellular and Molecular Physiology, 288:L932-L941 (2005).
European Search Report from Euro. Appl. No. EP10014830, Feb. 11, 2011.
European Search Report from Euro. Appl. No. 11177874, Nov. 21, 2011.
Intl Prelim. Report on Patentability, Nov. 6, 2007, Intl Application No. PCT/US2006/017248.
International Preliminary Report on Patentability, dated Nov. 18, 2007, from PCT Appl. No. PCT/US2006/019443.
International Search Report, dated Sep. 29, 2010, from PCT Appl. No. PCT/US2010/028900.
International Search Report, dated Sep. 24, 2010, from PCT Appl. No. PCT/US2010/028901.
International Search Report, dated Sep. 6, 2010, from PCT Appl. No. PCT/US2010/028906.
International Search Report, dated Sep. 15, 2010, from PCT Appl. No. PCT/US2010/028914.
Intl Search Report, dated Dec. 17, 2010, from PCT Application No. PCT/US2010/028961.
Intl Search Report, dated Dec. 1, 2011, from PCT Application No. PCT/US2011/049342.
Intl Search Report, dated Apr. 17, 2012, from PCT Application No. PCT/US2011/044628.
Intl Search Report, dated Nov. 22, 2011, from PCT Application No. PCT/US2011/049333.
Intl Search Report, dated Mar. 8 2012, from PCT Application No. PCT/US2011/049435.
Intl Search Report, dated Feb. 9, 2012, from PCT Application No. PCT/US2011/053833.
Intl Search Report, dated May 18, 2012, from PCT Application No. PCT/US2011/059330.
Intl Search Report, dated Mar. 12, 2013, from PCT Application No. PCT/US2012/059022.
Intl Search Report dated Sep. 6, 2013 from PCT Application No. PCT/US2013/028261.
Kulkarni, et al., "Formulation and Characterization of Nasal Sprays," Inhalation Magazine, 6(3):10-15 (2012).
Liedtke, et al., "A Possible Role for TRP4 Receptors in Asthma," American J. of Physiolog—Lung Cellular and Molecular Physiology,287:L269-L271 (2004).
Link, et al., "TRPV2 Has a Pivotal Role in Macrophage Particle Binding and phagocytosis," Nature Immunology, 11:232-239 (2010).
Lorenzo, et al., "TRPV4 Channel participates in Receptor-Operated Calcium Entry and Ciliary Beat Frequency Rgulation in Mouse Airway Epithelial Cells, Proceedings of the Natl Academy of Sciences of the United States of America," 12611 (2008).
Nilius, et al., "Transient Receptor Potential Cation Channels in Disease," Physiological Reviews, 87:165-217 (2007).
Rodwell, et al., "The effect of inhaled frusemide on airway sensitivity to inhaled 4.5% sodium chloride aerosol in asthmatic subject," Thorax (1993) 48:208-213.
Smith, et al., "Mechanism of Adenovirus neutralization by Human Alpha-defensins," Cell Host & Microbe, vol. 3., No. 1, pp. 11-19, Jan. 17, 2008.
Vincent, et al., Identification and Characterization of Novel TRPV4 Mudulators, Biochemical and Biophysical Research Communicaton, 389:490-494 (2009).
Yanire, Andrade, et al., "TRPV4 Channel is Involved in the Coupling of Fluid Viscosity Changes to Epithelial Ciliary Activity," J. Cell Biology, 168:869-874 (2005).
Tuberkuleza, Problemy 58(1): 40-41 (1980).

* cited by examiner

- Formulation II
- SPIRIVA (tiotropium bromide) HANDIHALER (dry powder inhaler)

Mass of Tiotropium (µg) vs Component (Capsule, Device, MA + IP + PS)

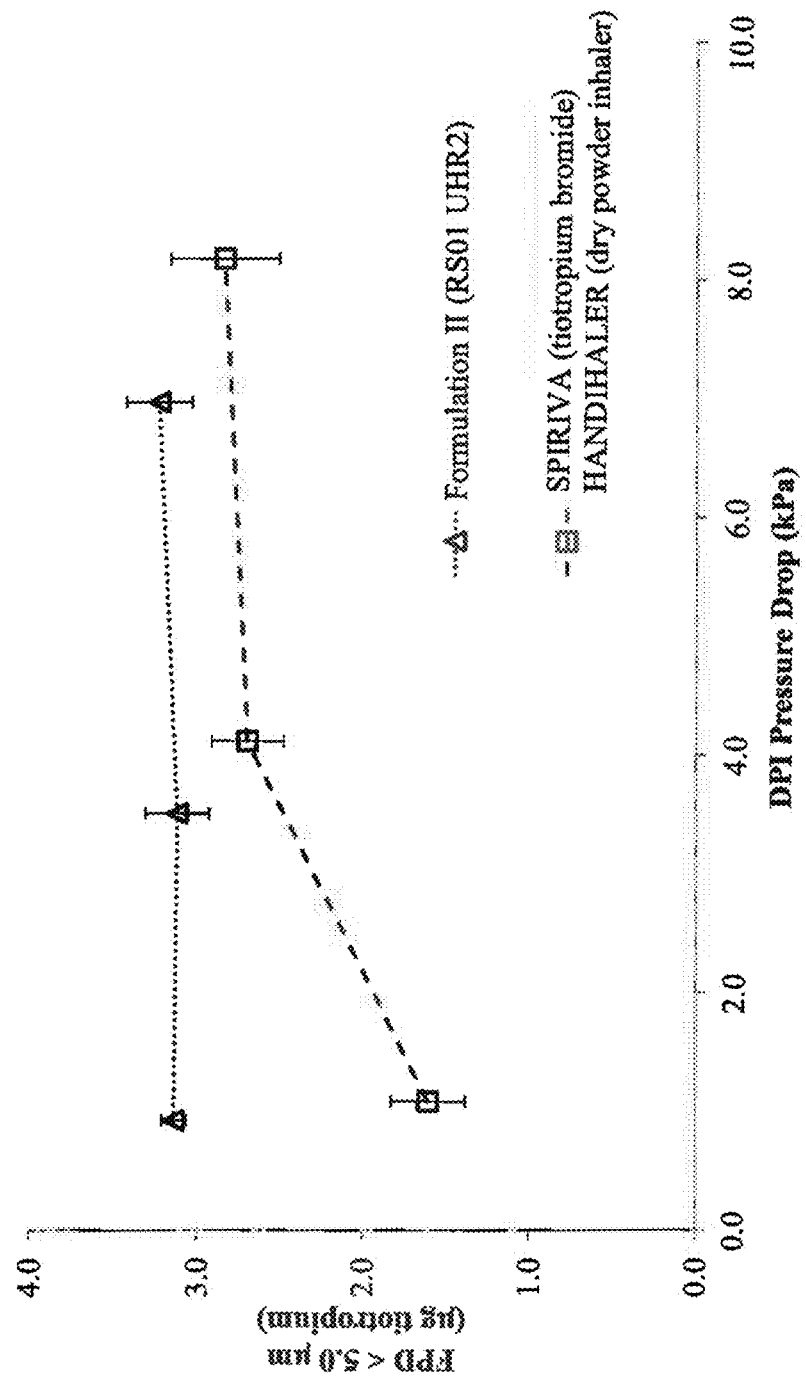

TIOTROPIUM DRY POWDERS

RELATED APPLICATIONS

This application is a continuation of International Application No. PCT/US2014/025660, filed Mar. 13, 2014, published in English, which claims the benefit of U.S. Patent Application No. 61/925,400, filed on Jan. 9, 2014, U.S. Patent Application No. 61/874,146, filed on Sep. 5, 2013, and U.S. Patent Application No. 61/807,063, filed on Apr. 1, 2013; the entire teachings of these applications are incorporated herein by reference.

BACKGROUND

The chemical structure of tiotropium was first described in U.S. Pat. No. 5,610,163 and RE39,820. Tiotropium salts include salts containing cationic tiotropium with one of the following anions: bromide, fluoride, chloride, iodine, C1-C4-alkylsulphate, sulphate, hydrogen sulphate, phosphate, hydrogen phosphate, di-hydrogen phosphate, nitrate, maleate, acetate, trifluoroacetate, citrate, fumarate, tartrate, oxalate, succinate and benzoate, C1-C4-alkylsulphonate, which may optionally be mono-, di- or tri-substituted by fluorine at the alkyl group, or phenylsulphonate, which may optionally be mono- or poly-substituted by C1-C4-alkyl at the phenyl ring. Tiotropium bromide is an anticholinergic providing therapeutic benefits, e.g. in the treatment of COPD and asthma, and is the active ingredient in SPIRIVA (tiotropium bromide) HANDIHALER (dry powder inhaler) (Boehringer Ingelheim, Germany). Tiotropium bromide is known to crystallize in various forms, such as crystalline anhydrous (described e.g. in U.S. Pat. Nos. 6,608,055; 7,968,717; and 8,163,913 (Form 11)), crystalline monohydrate (described e.g. in U.S. Pat. Nos. 6,777,423 and 6,908,928) and crystalline solvates (described e.g. in U.S. Pat. No. 7,879,871). The various crystalline forms of tiotropium can be distinguished by a number of different assays, including X-ray Powder Diffraction (XRPD), Differential scanning calorimetry (DSC), crystal structure, and infrared (IR) spectrum analysis. Tiotropium can be synthesized using a variety of methods which are well known in the art (including, e.g. methods described in U.S. Pat. Nos. 6,486,321; 7,491,824; 7,662,963; and 8,344,143).

SUMMARY OF THE INVENTION

The invention relates to a respirable dry powder comprising respirable dry particles that comprise sodium chloride, leucine, and tiotropium bromide, wherein the sodium chloride is about 60% to about 90%, the leucine is about 10% to about 40%, the tiotropium bromide is about 0.01% to about 0.5%, and optionally one or more additional therapeutic agents up to about 20%; preferably, the sodium chloride is about 67% to about 84%, the leucine is about 12% to about 28%, the tiotropium bromide is about 0.01% to about 0.5%, and optionally one or more additional therapeutic agents up to about 20%; more preferably, the sodium chloride is about 75% to about 82% and the leucine is about 15% to about 25%; and most preferably, the sodium chloride is about 79.5% to about 80.5% and the leucine is about 19.5% to about 20.5%, where all the percentages are weight percentages on a dry basis and all the components of the respirable dry particles amount to 100%. The invention also relates to a respirable dry powder comprising respirable dry particles that comprise sodium chloride, leucine, and tiotropium bromide, wherein the sodium chloride is about 65% to about 86%, the leucine is about 10% to about 35%, the tiotropium bromide is about 0.01% to about 0.5%, and optionally one or more additional therapeutic agents, wherein the one or more additional therapeutic agents is about 1% to about 10%, more preferably the one or more additional therapeutic agents is about 3% to about 7%, and most preferably the one or more additional therapeutic agents is about 4% to about 5%, wherein all the percentages are weight percentages on a dry basis and all the components of the respirable dry particles amount to 100%.

The invention also relates to a respirable dry powder comprising respirable dry particles consist of sodium chloride, leucine, and tiotropium bromide, wherein the ratio of sodium chloride to leucine is 2.5:1 to 8:1 (w/w), the tiotropium bromide is about 0.01% to about 0.5%, and optionally one or more additional therapeutic agent up to about 20%; preferably, the ratio of sodium chloride to leucine is 3:1 to 6:1 (w/w); and most preferably, the ratio of sodium chloride to leucine is about 4:1 (w/w), where all percentages are weight percentages on a dry basis and all the components of the respirable dry particles amount to 100%. The invention also relates to a respirable dry powder comprising respirable dry particles consist of sodium chloride, leucine, and tiotropium bromide, wherein the ratio of sodium chloride to leucine is 1.5:1 to 9:1 (w/w), the tiotropium bromide is about 0.01% to about 0.5%, and optionally one or more additional therapeutic agent up to about 20%; preferably, the ratio of sodium chloride to leucine is 1.9:1 to 8.5:1 (w/w), where all percentages are weight percentages on a dry basis and all the components of the respirable dry particles amount to 100%.

The respirable dry powder comprising respirable dry particles sometimes do not contain an additional therapeutic agent.

The respirable dry powder comprising respirable dry particles, at other times, do contain an additional therapeutic agent of 20% or less of the formulation, by dry weight. The one or more additional therapeutic agent may be present in an amount of about 0.01% to about 10%, specifically, the one or more additional therapeutic agent may be present in an amount of about 0.01% to 0.5%, an amount greater than 0.5% to 3%, or an amount greater than 3% to about 10%. The one or more additional therapeutic agent is independently selected from the group consisting of one or more corticosteroid, one or more long-acting beta agonist, one or more short-acting beta agonist, one or more anti-inflammatory agent, one or more bronchodilator, and any combination thereof.

The respirable dry powder comprising respirable dry particles contains about 0.01% to about 0.5% tiotropium bromide, or contains about 0.02% to about 0.25% tiotropium bromide, where the percentages are weight percentages on a dry basis.

The respirable dry powder comprising respirable dry particles have one or more of the following characteristics and/or properties: a volume median geometric diameter (VMGD) about 10 micrometers or less, or about 1 micrometer to about 4 micrometers; a tap density of at least about 0.45 g/cc, about 0.45 g/cc to about 1.2 g/cc, at least about 0.5 g/cc, at least about 0.55 g/cc, or at least about 0.55 g/cc to about 1.0 g/cc; a mass median aerodynamic diameter of between about 1 micron and about 5 microns, between about 2 microns and about 5 microns, or preferably, between about 2.5 microns and about 4.5 microns; a fine particle dose less than 4.4 microns of between about 1 microgram and about 5 micrograms of tiotropium, or about 2.0 micrograms and about 5.0 micrograms of tiotropium; a ratio of the fine particle dose less than 2.0 microns to the fine particle dose less than 4.4 microns of less than about 0.50, or preferably, less than about 0.35, or less than about 0.25; a 1/4 bar dispersibility ratio of less than about 1.5, or less than about 1.4, a 0.5/4 bar dispersibility ratio of about 1.5 or less, all dispersibility ratios were measured by laser diffraction; an FPF of the total dose less than 3.4 microns of about 25% or more, between about 25% and about 60%, about 40% or more, or between about 40% to about 60%; an FPF of the total dose less than 5.6 microns of about 45% or more, about 45% to about 80%, about 60% or more, or about 60% to about 80%.

Also, they may have a tap density of at least about 0.4 g/cm$^3$, a tap density of greater than 0.4 g/cm$^3$, or greater than 0.4 g/cm$^3$ to about 1.2 g/cm$^3$; an mass median aerodynamic diameter (MMAD) of preferably between about 3 micron and about 5 microns, or about 4 microns; or between about 3 microns and about 6 microns, or, preferably, between about 4 microns and about 6 microns, preferably, about 5 microns; a fine particle dose less than 4.4 microns of between about 1 microgram and about 4 micrograms of tiotropium, or, preferably, between about 1.5 micrograms and 3.5 micrograms, about 2.0 micrograms, about 2.5 micrograms, or about 3.0 micrograms; a ratio of the fine particle dose less than 2.0 microns to the fine particle dose less than 5.0 microns of less than about 0.50, or preferably, less than about 0.35, or preferably less than 0.25, less than 0.20, or less than 0.18.

The respirable dry powder comprising respirable dry particles has a capsule emitted powder mass of at least 80% when emitted from a passive dry powder inhaler that has a resistance of about 0.036 sqrt(kPa)/liters per minute under the following conditions; an inhalation energy of 2.3 Joules at a flow rate of 30 LPM using a size 3 capsule that contains a total mass of 10 mg, said total mass consisting of the respirable dry particles, and wherein the volume median geometric diameter of the respirable dry particles emitted from the inhaler as measured by laser diffraction is 5 microns or less.

The invention also relates to a method of treating a respiratory disease and/or to a method of treating or reducing the incidence or severity of an acute exacerbation of a respiratory disease by administering to the respiratory tract of a patient in need thereof the respiratory powder comprising respiratory particles.

Additionally, the invention also relates to a method of relieving the symptoms of a respiratory disease and/or a method of improving the lung function of a patient with a respiratory disease by administering to the respiratory tract of a patient in need thereof the respiratory powder comprising respiratory particles. Without wishing to be bound by theory, it is believed that improving a patient's lung function over a period of time is a long-term way to treat respiratory disease and/or to prevent acute exacerbations.

The respirable dry powder comprising respirable dry particles may be used 1) in treating a respiratory disease in an individual, the use comprising administering to the respiratory tract of the individual an effective amount of the respirable dry powder, resulting in the treatment of a respiratory disease, and/or, 2) in treating or reducing the incidence or severity of an acute exacerbation of a respiratory disease in an individual, the use comprising administering to the respiratory tract of the individual an effective amount of the respirable dry powder, resulting in the treatment or reduction in the incidence or severity of an acute exacerbation of a respiratory disease.

Additionally, the respiratory dry powder comprising respiratory dry particles may be used 1) in relieving the symptoms of a respiratory disease, the use comprising administering to the respiratory tract of the individual an effective amount of the respirable dry powder, resulting in the relief of the symptoms of a respiratory disease, and/or, 2) in improving the lung function of a patient with a respiratory disease, the use comprising administering to the respiratory tract of the individual an effective amount of the respirable dry powder, resulting in an improvement of the lung function of a patient with a respiratory disease.

In some embodiments, the respiratory disease is COPD, chronic bronchitis, emphysema, asthma, cystic fibrosis, or non-cystic fibrosis bronchiectasis. The respiratory disease is preferably COPD, chronic bronchitis, and/or emphysema.

The respirable dry powder comprising respirable dry particles may be contained in a dry powder inhaler. The dry powder inhaler may be a capsule-based dry powder inhaler, a blister-based dry powder inhaler, or a reservoir-based dry powder inhaler. The respirable dry powder comprising respirable dry particles may be contained in a receptacle. The receptacle may be a capsule or a blister, where the receptacle is suitable for any of the dry powder inhalers listed above. The receptacle contains the respirable dry powder of a mass of about 15 mg or less, about 11 mg or less, about 8.5 mg or less, about 6 mg or less, or about 4 mg or less. The receptacle may contain the respirable dry powder of a mass of about 15 mg, 10 mg, 7.5 mg, 5 mg, 2.5 mg, or 1 mg. The receptacle may contain a nominal dose of tiotropium between about 1.5 to about 12 micrograms, between about 3 to about 12 micrograms, between about 3 to about 9 micrograms, or between about 3 to about 6 micrograms. The receptacle may contain a nominal dose of tiotropium of about 1.5 micrograms, about 3 micrograms, about 6 micrograms, about 9 micrograms, or about 12 micrograms. The receptacle can be contained in a dry powder inhaler or can be packaged and/or sold separately.

The respirable dry powder comprising respirable dry particles may be contained in a dry powder inhaler. The dry powder inhaler is preferably a capsule-based dry powder inhaler. More preferably, the dry powder inhaler is selected from the RS01 family of dry powder inhalers (Plastiape S.p.A., Italy). More preferably, the dry powder inhaler is selected from the RS01 HR or the RS01 UHR2. In one aspect, the dry powder inhaler is not the RS01 HR. Most preferably, the dry powder inhaler is the RS01 UHR2. The respirable dry powder comprising respirable dry particles may be contained in a receptacle. The receptacle is preferably a capsule. Preferably, the capsule material is selected from gelatin and HPMC (Hydroxypropyl methylcellulose). More preferably, the capsule material is HPMC. In one aspect, the capsule material is not gelatin. Preferably, the receptacle is a size 3 capsule. More preferably the receptacle is a size 3, HPMC capsule. Most preferably, the respirable dry powder comprising respirable dry particles is contained in a size 3 HPMC capsule for use in the RS01 UHR2 dry powder inhaler. In one aspect, the respirable dry powder consists of respirable dry particles.

BRIEF DESCRIPTION OF THE DRAWINGS

FIG. 3 is a graph of the aerodynamic size distributions at 4 kPA pressure drop for Formulation II at a 5.8 μg nominal dose and SPIRIVA (tiotropium bromide) HANDIHALER (dry powder inhaler) at a 18 μg nominal dose, illustrating a similar fine particle dose (FPD) for Formulation II with a reduced nominal drug loading.

FIG. 4 is a graph showing that Formulation II has minimal oral deposition versus the SPIRIVA (tiotropium bromide) HANDIHALER (dry powder inhaler), reducing potential side effects.

FIG. 10 is a graph depicting reduced flow rate dependence of Formulation II delivered from the RS01 UHR2 versus the SPIRIVA (tiotropium bromide) HANDIHALER (dry powder inhaler) across a range of patient relevant inhalation pressure drops.

DETAILED DESCRIPTION OF THE INVENTION

Figure 1A:
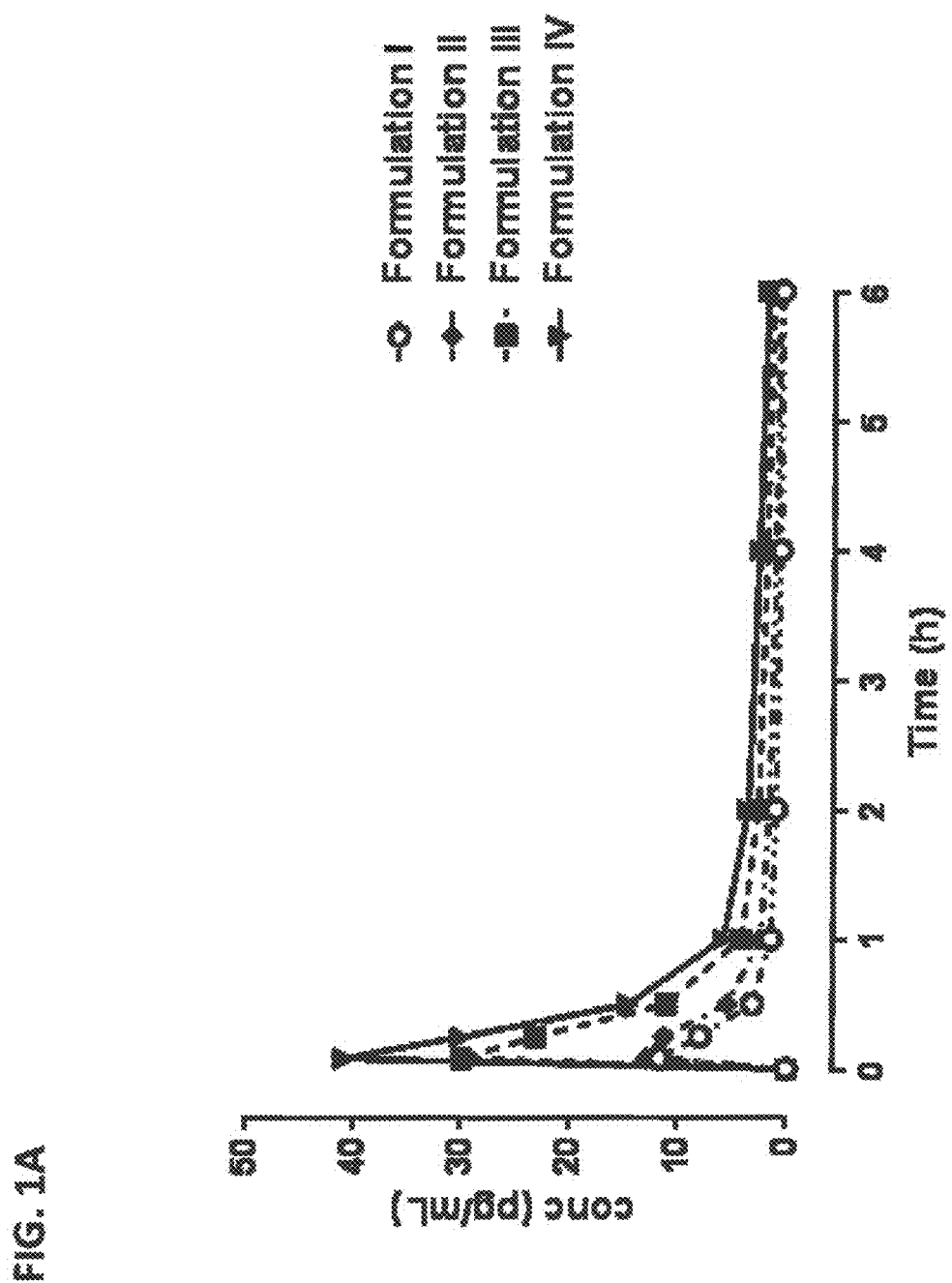
FIG. 1A is a graph depicting the geometric mean of plasma levels of tiotropium in pg/ml over time for exemplary Formulations I, II, III, and IV, respectively.

The invention relates to respirable dry powders containing respirable dry particles that comprise sodium chloride, leucine, and tiotropium bromide, wherein the sodium chloride is about 60% to about 90%, the leucine is about 10% to about 40%, the tiotropium bromide is about 0.01% to about 0.5%, and optionally one or more additional therapeutic agents up to about 20%; preferably, the sodium chloride is about 67% to about 84%, the leucine is about 12% to about 28%, the tiotropium bromide is about 0.01% to about 0.5%, and optionally one or more additional therapeutic agents up to about 20%; preferably, the sodium chloride is about 75% to about 82% and the leucine is about 15% to about 25%; and most preferably, the sodium chloride is about 79.5% to about 80.5% and the leucine is about 19.5% to about 20.5%, where all the percentages are weight percentages on a dry basis and all the components of the respirable dry particles amount to 100%. The invention also relates to a respirable dry powder comprising respirable dry particles that comprise sodium chloride, leucine, and tiotropium bromide, wherein the sodium chloride is about 65% to about 86%, the leucine is about 10% to about 35%, the tiotropium bromide is about 0.01% to about 0.5%, and optionally one or more additional therapeutic agents, wherein the one or more additional therapeutic agents is about 1% to about 10%, more preferably the one or more additional therapeutic agents is about 3% to about 7%, and most preferably the one or more additional therapeutic agents is about 4% to about 5%, wherein all the percentages are weight percentages on a dry basis and all the components of the respirable dry particles amount to 100%.

The invention also relates to a respirable dry powder comprising respirable dry particles consist of sodium chloride, leucine, and tiotropium bromide, wherein the ratio of sodium chloride to leucine is 2.5:1 to 8:1 (w/w), the tiotropium bromide is about 0.01% to about 0.5%, and optionally one or more additional therapeutic agent up to about 20%; preferably, the ratio of sodium chloride to leucine is 3:1 to 6:1 (w/w); and most preferably, the ratio of sodium chloride to leucine is about 4:1, where all percentages are weight percentages on a dry basis and all the components of the respirable dry particles amount to 100%. The invention also relates to a respirable dry powder comprising respirable dry particles consist of sodium chloride, leucine, and tiotropium bromide, wherein the ratio of sodium chloride to leucine is 1.5:1 to 9:1 (w/w), the tiotropium bromide is about 0.01% to about 0.5%, and optionally one or more additional therapeutic agent up to about 20%; preferably, the ratio of sodium chloride to leucine is 1.9:1 to 8.5:1 (w/w), where all percentages are weight percentages on a dry basis and all the components of the respirable dry particles amount to 100%.

These respirable dry powders comprising respirable dry particles may be manufactured from their components, in solutions or suspensions that are aqueous and/or contain another solvent, by spray drying or other comparable processes. The respirable dry powders comprising respirable dry particles are relatively dry in water and solvent content, small in geometric diameter, dense in mass density, and dispersible in that they deagglomerate from each other with a relatively low amount of energy. They have superior aerosol properties such as a relatively small aerodynamic diameter, a relatively high fine particle fraction and fine particle dose below sizes that are relevant to lung deposition. These properties are illustrated for two exemplary formulations in Example 1. Three additional preferred respirable dry powders comprising respirable dry particles that comprise sodium chloride, leucine and tiotropium are described in Example 3. Despite the processing that takes place to make the respirable dry powders comprising respirable dry particles, the tiotropium bromide maintains its activity as is demonstrated in the in vivo experiment described in Examples 2 and 4.

Definitions

As used herein, the term "about" refers to a relative range of plus or minus 5% of a stated value, e.g., "about 20 mg" would be "20 mg plus or minus 1 mg".

As used herein, the terms "administration" or "administering" of respirable dry particles refers to introducing respirable dry particles to the respiratory tract of a subject.

The term "capsule emitted powder mass" or "CEPM" as used herein refers to the amount of dry powder formulation emitted from a capsule or dose unit container during an inhalation maneuver. CEPM is measured gravimetrically, typically by weighing a capsule before and after the inhalation maneuver to determine the mass of powder formulation removed. CEPM can be expressed either as the mass of powder removed, in milligrams, or as a percentage of the initial filled powder mass in the capsule prior to the inhalation maneuver.

The term "dispersible" is a term of art that describes the characteristic of a dry powder or dry particles to be dispelled into a respirable aerosol. Dispersibility of a dry powder or dry particles is expressed herein as the quotient of the volumetric median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by laser diffraction, such as with a HELOS/RODOS. These quotients are referred to herein as "1 bar/4 bar dispersibility ratio", and "0.5 bar/4 bar dispersibility ratio", respectively, and dispersibility correlates with a low quotient. For example, 1 bar/4 bar dispersibility ratio refers to the VMGD of respirable dry particles or powders emitted from the orifice of a RODOS dry powder disperser (or equivalent technique) at about 1 bar, as measured by a HELOS or other laser diffraction system, divided by the VMGD of the same respirable dry particles or powders measured at 4 bar by HELOS/RODOS. Thus, a highly dispersible dry powder or respirable dry particles will have a 1 bar/4 bar dispersibility ratio or 0.5 bar/4 bar dispersibility ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by a subject. Dispersibility can also be assessed by measuring the size emitted from an inhaler as a function of flowrate. As the flow rate through the inhaler decreases, the amount of energy in the airflow available to be transferred to the powder to disperse it decreases. A highly dispersible powder will have its size distribution as characterized aerodynamically by its mass median aerodynamic diameter (MMAD) or geometrically by its VMGD, not substantially increase over a range of flow rates typical of inhalation by humans, such as about 15 to 60 LPM, or about 20 to 60 LPM. VMGD may also be called the volume median diameter (VMD), x50, or Dv50.

The term "dry particles" as used herein refers to respirable particles that may contain up to about 15% water or other solvent. Preferably the dry powders contain water or other solvent up to about 10%, up to about 5%, up to about 1%, or between 0.01% and 1%, by weight of the dry particles, or can be substantially free of water or other solvent, or be anhydrous.

The term "dry powders" as used herein refers to compositions that comprise respirable dry particles. Preferably the respirable dry powders contain water or other solvent up to about 10%, up to about 5%, up to about 1%, or between 0.01% and 1%, by weight of the respirable dry particles, or can be substantially free of water or other solvent, or be anhydrous.

The term "effective amount," as used herein, refers to the amount of agent needed to achieve the desired effect; improve or prevent deterioration of respiratory function (e.g., improve forced expiratory volume in 1 second ($FEV_1$) and/or forced expiratory volume in 1 second ($FEV_1$) as a proportion of forced vital capacity ($FEV_1$/FVC)), reduce the occurrence of an acute exacerbation of a respiratory disease, e.g., Chronic Obstructive Pulmonary Disease (COPD), asthma, Cystic Fibrosis (CF), and non-CF Bronchiectasis.

The actual effective amount for a particular use can vary according to the particular dry powder or dry particle, the mode of administration, and the age, weight, general health of the subject, and severity of the symptoms or condition being treated. Suitable amounts of dry powders and dry particles to be administered, and dosage schedules for a particular patient can be determined by a clinician of ordinary skill based on these and other considerations.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia convention, Rockville, Md., $13^{th}$ Revision, 222-225, 2007. This method utilizes an in vitro device set up to mimic patient dosing.

The terms "FPF (<5.6)," "FPF (<5.6 microns)," and "fine particle fraction of less than 5.6 microns" as used herein, refer to the fraction of a sample of dry particles that have an aerodynamic diameter of less than 5.6 microns. For example, FPF (<5.6) can be determined by dividing the mass of respirable dry particles deposited on the stage two and on the final collection filter of a two-stage collapsed Andersen Cascade Impactor (ACI) by the mass of respirable dry particles weighed into a capsule for delivery to the instrument. This parameter may also be identified as "FPF_TD (<5.6)," where TD means total dose. A similar measurement can be conducted using an eight-stage ACI. The eight-stage ACI cutoffs are different at the standard 60 L/min flowrate, but the FPF_TD(<5.6) can be extrapolated from the eight-stage complete data set. The eight-stage ACI result can also be calculated by the USP method of using the dose collected in the ACI instead of what was in the capsule to determine FPF.

The terms "FPD (<4.4)", 'FPD<4.4 μm", FPD(<4.4 microns)" and "fine particle dose of less than 4.4 microns" as used herein, refer to the mass of respirable dry powder particles that have an aerodynamic diameter of less than 4.4 micrometers. For example, FPD<4.4 μm can be determined by using an eight-stage ACI at the standard 60 L/min flowrate and summing the mass deposited on the final collection filter, and stages 6, 5, 4, 3, and 2 for a single dose of powder actuated into the ACI.

The terms "FPF (<5.0)", "FPF<5 μm", "FPF (<5.0 microns)," and "fine particle fraction of less than 5.0 microns" as used herein, refer to the fraction of a mass of respirable dry particles that have an aerodynamic diameter of less than 5.0 micrometers. For example, FPF (<5.0) can be determined by using an eight-stage ACI at the standard 60 L/min flow rate by extrapolating from the eight-stage complete data set. This parameter may also be identified as "FPF_TD(<5.0)," where TD means total dose. When used in conjunction with a geometric size distribution such as those given by a Malvern Spraytec, Malvern Mastersizer or Sympatec HELOS particle sizer, "FPF (<5.0)" refers to the fraction of a mass of respirable dry particles that have a geometric diameter of less than 5.0 micrometers.

The terms "FPF (<3.4)," "FPF (<3.4 microns)," and "fine particle fraction of less than 3.4 microns" as used herein, refer to the fraction of a mass of respirable dry particles that have an aerodynamic diameter of less than 3.4 microns. For example, FPF (<3.4) can be determined by dividing the mass of respirable dry particles deposited on the final collection filter of a two-stage collapsed ACI by the total mass of respirable dry particles weighed into a capsule for delivery to the instrument. This parameter may also be identified as "FPF_TD(<3.4)," where TD means total dose. A similar measurement can be conducted using an eight-stage ACI. The eight-stage ACI result can also be calculated by the USP method of using the dose collected in the ACI instead of what was in the capsule to determine FPF.

"Hausner ratio" is a term of art that refers to the tap density divided by the bulk density and typically correlates with bulk powder flowability (i.e., an increase in the Hausner ratio typically corresponds to a decrease in powder flowability The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

As used herein, the term "respiratory tract" includes the upper respiratory tract (e.g., nasal passages, nasal cavity, throat, and pharynx), respiratory airways (e.g., larynx, trachea, bronchi, and bronchioles) and lungs (e.g., respiratory bronchioles, alveolar ducts, alveolar sacs, and alveoli).

The term "small" as used herein to describe respirable dry particles refers to particles that have a volume median geometric diameter (VMGD) of about 10 microns or less, preferably about 5 microns or less.

Dry Powders and Dry Particles

The invention relates to respirable dry powders and respirable dry particles that contain tiotropium as an active ingredient. The chemical structure of tiotropium was first described in U.S. Pat. No. 5,610,163 and RE39,820. Tiotropium salts include salts containing cationic tiotropium with one of the following anions: bromide, fluoride, chloride, iodine, C1-C4-alkylsulphate, sulphate, hydrogen sulphate, phosphate, hydrogen phosphate, di-hydrogen phosphate, nitrate, maleate, acetate, trifluoroacetate, citrate, fumarate, tartrate, oxalate, succinate and benzoate, C1-C4-alkylsulphonate, which may optionally be mono-, di- or tri-substituted by fluorine at the alkyl group, or phenylsulphonate, which may optionally be mono- or poly-substituted by C1-C4-alkyl at the phenyl ring. Tiotropium bromide is an anticholinergic providing therapeutic benefits, e.g. in the treatment of COPD and asthma, and is the active ingredient in SPIRIVA (tiotropium bromide) HANDIHALER (dry powder inhaler) (Boehringer Ingelheim, Germany). Tiotropium bromide is known to crystallize in various forms, such as crystalline anhydrous (described e.g. in U.S. Pat. Nos. 6,608,055; 7,968,717; and 8,163,913 (Form 11)), crystalline monohydrate (described e.g. in U.S. Pat. Nos. 6,777,423 and 6,908,928) and crystalline solvates (described e.g. in U.S. Pat. No. 7,879,871). The various crystalline forms of tiotropium can be distinguished by a number of different assays, including X-ray Powder Diffraction (XRPD), Differential scanning calorimetry (DSC), crystal structure, and infrared (IR) spectrum analysis. Tiotropium can be synthesized using a variety of methods which are well known in the art (including, e.g. methods described in U.S. Pat. Nos. 6,486,321; 7,491,824; 7,662,963; and 8,344,143).

The tiotropium is generally present in the respirable dry powders and respirable dry particles in the form of tiotropium bromide. In particular, the respirable dry powders comprise respirable dry particles that contain, on a dry basis: about 79.5% (w/w) to about 80.5% (w/w) sodium chloride, about 19.5% (w/w) to about 20.5% (w/w) leucine, and about 0.01% (w/w) to about 0.5% (w/w) tiotropium bromide, and/or sodium chloride to leucine in a weight ratio of about 4:1, and about 0.01% (w/w) to about 0.5% (w/w) tiotropium bromide. For example, the invention provides respirable dry powders referred to as Formulations I-V, listed in Table 1.

TABLE 1

Tiotropium formulations

| Formulation | Composition (wt %, dry basis) | | |
|---|---|---|---|
| | Tiotropium Bromide | Leucine | Sodium Chloride |
| I | 0.04 | 19.99 | 79.97 |
| II | 0.07 | 19.99 | 79.94 |
| III | 0.11 | 19.98 | 79.91 |
| IV | 0.14 | 19.97 | 79.89 |
| V | 0.22 | 19.96 | 79.82 |

Additionally, the tiotropium formulations may be adjusted to allow for an additional therapeutic agent. In one embodiment, the respirable dry powders comprise respirable dry particles that contain, on a dry basis: about 60% to about 90% sodium chloride, about 10% to about 40% leucine, about 0.01% to about 0.5% tiotropium bromide, and optionally one or more additional therapeutic agents up to about 20%. In another embodiment, the respirable dry powders comprise respirable dry particles that contain, on a dry basis: about 67% to about 84% sodium chloride, about 12% to about 28% leucine, about 0.01 to about 0.5% tiotropium bromide, and optionally one or more additional therapeutic agent up to about 20%. Optionally, the sodium chloride content is about 75% to about 82% and/or the leucine content is about 15% to about 25%. The tiotropium bromide is preferably present in an amount between about 0.02% and 0.25%, by weight on a dry basis. The one or more additional therapeutic agent is preferably present in an amount between about 0.01% to about 10%, more preferably between about 0.01% to 0.5%, greater than 0.5% to 3%, or greater than 3% to about 10%. In another embodiment, the respirable dry powder comprising respirable dry particles that contain, on a dry basis, about 65% to about 86% sodium chloride, about 10% to about 35% leucine, about 0.01% to about 0.5% tiotropium bromide, and optionally one or more additional therapeutic agents, wherein the one or more additional therapeutic agents is about 1% to about 10%, more preferably the one or more additional therapeutic agents is about 3% to about 7%, and most preferably the one or more additional therapeutic agents is about 4% to about 5%. The tiotropium bromide formulations described in this paragraph are collectively referred to as "Expanded Tiotropium Formulations".

Additional preferred therapeutic combinations with tiotroprium include corticosteroids, such as inhaled corticosteroids (ICS), long-acting beta agonists (LABA), short-acting beta agonists (SABA), anti-inflammatory agents, and any combination thereof. A bifunctional muscarinic antagonist-beta2 agonist (MABA) is optionally included among these additional therapeutic combinations. In a most preferred embodiment, the tiotropium is combined with one or more ICS. Particularly preferred therapeutic combinations with tiotroprium include: a) tiotropium and corticosteroids, such as inhaled corticosteroids (ICS); b) tiotropium and long-acting beta agonists (LABA); c) tiotropium and short-acting beta agonists (SABA); d) tiotropium and anti-inflammatory agents; e) tiotropium and MABA, f) tiotropium and a bronchodilator, and any combination thereof. Combinations thereof include, but are not limited to, tiotropium and ICS and LABA.

Suitable corticosteroids, such as inhaled corticosteroids (ICS), include budesonide, fluticasone, flunisolide, triamcinolone, beclomethasone, mometasone, ciclesonide, dexamethasone, and the like.

Tiotropium can be delivered once per day (QD) to patients, so inhaled corticosteroids whose pharmacological data and dosing regimen support administration once per day are preferred. Preferred inhaled corticosteroids are fluticasone, e.g., fluticasone furoate, mometasone, e.g., mometasone furoate, ciclesonide, and the like.

Suitable LABAs include salmeterol, formoterol and isomers (e.g., arformoterol), clenbuterol, tulobuterol, vilanterol (Revolair™), indacaterol, carmoterol, isoproterenol, procaterol, bambuterol, milveterol, olodaterol, and the like.

Suitable SABAs include albuterol, epinephrine, pirbuterol, levalbuterol, metaproterenol, maxair, and the like.

Suitable MABAs include AZD 2115 (AstraZeneca), GSK961081 (GlaxoSmithKline), LAS 190792 (Almirall), PF4348235 (Pfizer) and PF3429281 (Pfizer).

Combinations of corticosteroids and LABAs include salmeterol with fluticasone, formoterol with budesonide, formoterol with fluticasone, formoterol with mometasone, indacaterol with mometasone, and the like.

Suitable anti-inflammatory agents include leukotriene inhibitors, phosphodiesterase 4 (PDE4) inhibitors, other anti-inflammatory agents, and the like.

Other suitable anti-inflammatory agents are kinase inhibitors.

Other anti-inflammatory agents include omalizumab (anti-IgE immunoglobulin Daiichi Sankyo Company, Limited), Zolair (anti-IgE immunoglobulin, Genentech Inc, Novartis AG, Roche Holding Ltd), Solfa (LTD4 antagonist and phosphodiesterase inhibitor, Takeda Pharmaceutical Company Limited), IL-13 and IL-13 receptor inhibitors (such as AMG-317, MILR1444A, CAT-354, QAX576, IMA-638, Anrukinzumab, IMA-026, MK-6105, DOM-0910, and the like), IL-4 and IL-4 receptor inhibitors (such as Pitrakinra, AER-003, AIR-645, APG-201, DOM-0919, and the like), IL-1 inhibitors such as canakinumab, CRTh2 receptor antagonists such as AZD1981 (CRTh2 receptor antagonist, AstraZeneca), neutrophil elastase inhibitor such as AZD9668 (neutrophil elastase inhibitor, from AstraZeneca), P38 mitogen-activated protein kinases inhibitor, e.g., GW856553X Losmapimod, GSK681323, GSK 856553, and GSK610677 (all P38 kinase inhibitors, GlaxoSmithKline PLC), and PH-797804 (p38 kinase inhibitor; Pfizer), Arofylline LAB ALMIRALL (PDE-4 inhibitor, Laboratorios Almirall, S.A.), ABT761 (5-LO inhibitor, Abbott Laboratories), Zyflo® (5-LO inhibitor, Abbott Laboratories), BT061 (anti-CD4 mAb, Boehringer Ingelheim GmbH), BIBW 2948 BS (map kinase inhibitor), Corus (inhaled lidocaine to decrease eosinophils, Gilead Sciences Inc.), Prograf® (IL-2-mediated T-cell activation inhibitor, Astellas Pharma), Bimosiamose PFIZER INC (selectin inhibitor, Pfizer Inc), R411 (alpha4beta1/alpha4beta7 integrin antagonist, Roche Holdings Ltd), Tilade® (inflammatory mediator inhibitor, Sanofi-Aventis), Orenica® (T-cell co-stimulation inhibitor, Bristol-Myers Squibb Company), Soliris® (anti-05, Alexion Pharmaceuticals Inc), Entorken® (Farmacija d.o.o.), Excellair® (Syk kinase siRNA, ZaBeCor Pharmaceuticals, Baxter International Inc), KB003 (anti-GMCSF mAb, KaloBios Pharmaceuticals), Cromolyn sodiums (inhibit release of mast cell mediators): Cromolyn sodium BOEHRINGER (Boehringer Ingelheim GmbH), Cromolyn sodium TEVA (Teva Pharmaceutical Industries Ltd), Intal (Sanofi-Aventis), BI1744CL (oldaterol (beta-2-adrenoceptor antagonist) and tiotropium, Boehringer Ingelheim GmbH), NFkappa-B inhibitors, CXR2 antagaonists, HLE inhibitors, HMG-CoA reductase inhibitors and the like.

Anti-inflammatory agents also include compounds that inhibit/decrease cell signaling by inflammatory molecules like cytokines (e.g., IL-1, IL-4, IL-5, IL-6, IL-9, IL-13, IL-18 IL-25, IFN-α, IFN-β, and others), CC chemokines CCL-1-CCL28 (some of which are also known as, for example, MCP-1, CCL2, RANTES), CXC chemokines CXCL1-CXCL17 (some of which are also know as, for example, IL-8, MIP-2), CXCR2, growth factors (e.g., GM-CSF, NGF, SCF, TGF-β, EGF, VEGF and others) and/or their respective receptors.

Some examples of the aforementioned anti-inflammatory antagonists/inhibitors include ABN912 (MCP-1/CCL2, Novartis AG), AMG761 (CCR4, Amgen Inc), Enbrel® (TNF, Amgen Inc, Wyeth), huMAb OX40L GENENTECH (TNF superfamily, Genentech Inc, AstraZeneca PLC), R4930 (TNF superfamily, Roche Holding Ltd), SB683699/Firategrast (VLA4, GlaxoSmithKline PLC), CNT0148 (TNFalpha, Centocor, Inc, Johnson & Johnson, Schering-Plough Corp); Canakinumab (IL-beta, Novartis); Israpafant MITSUBISHI (PAF/IL-5, Mitsubishi Tanabe Pharma Corporation); IL-4 and IL-4 receptor antagonists/inhibitors: AMG317 (Amgen Inc), BAY169996 (Bayer AG), AER-003 (Aerovance), APG-201 (Apogenix); IL-5 and IL-5 receptor antagonists/inhibitors: MEDI563 (AstraZeneca PLC, MedImmune, Inc), Bosatria® (GlaxoSmithKline PLC), Cinquil® (Ception Therapeutic), TMC120B (Mitsubishi Tanabe Pharma Corporation), Bosatria (GlaxoSmithKline PLC), Reslizumab SCHERING (Schering-Plough Corp); MEDI528 (IL-9, AstraZeneca, MedImmune, Inc); IL-13 and IL-13 receptor antagonists/inhibitors: TNX650 GENENTECH (Genentech), CAT-354 (AstraZeneca PLC, MedImmune), AMG-317 (Takeda Pharmaceutical Company Limited), MK6105 (Merck & Co Inc), IMA-026 (Wyeth), IMA-638 Anrukinzumab (Wyeth), MILR1444A/Lebrikizumab (Genentech), QAX576 (Novartis), CNTO-607 (Centocor), MK-6105 (Merck, CSL); Dual IL-4 and IL-13 inhibitors: AIR645/ISIS369645 (ISIS Altair), DOM-0910 (GlaxoSmithKline, Domantis), Pitrakinra/AER001/Aerovant™ (Aerovance Inc), AMG-317 (Amgen), and the like. CXCR2 antagonists include, for example, Reparixin (Dompe S.P.A.), DF2162 (Dompe, S.P.A.), AZ-10397767 (AstraZeneca), SB656933 (GlaxoSmithKline PLC), SB332235 (GlaxoSmithKline PLC), SB468477 (GlaxoSmithKline PLC), and SCH527123 (Schering-Plough Corp).

In Formulations I to V and/or in the Expanded Tiotropium Formulations, the respirable dry powders and/or respirable dry particles are preferably small, mass dense, and dispersible. To measure volumetric median geometric diameter (VMGD), a laser diffraction system may be used, e.g., a Spraytec system (particle size analysis instrument, Malvern Instruments) and a HELOS/RODOS system (laser diffraction sensor with dry dispensing unit, Sympatec GmbH). The respirable dry particles of Formulations I to V have a VMGD as measured by laser diffraction at the dispersion pressure setting of 1.0 bar using a HELOS/RODOS system of about 10 microns or less (e.g., about 0.5 µm to about 10 µm), about 5 microns or less (e.g., about 0.5 µm to about 5 µm), about 4 µm or less (e.g., about 0.5 µm to about 4 µm), about 3 µm or less (e.g., about 0.5 µm to about 3 µm), about 1 µm to about 5 µm, about 1 µm to about 4 µm, about 1.5 µm to about 3.5 µm, about 2 µm to about 5 µm, about 2 µm to about 4 µm, or about 2 µm to about 3 µm. Preferably the VMGD is about 5 microns or less (e.g., about 1 µm to about 5 µm), or about 4 µm or less (e.g., about 1 µm to about 4 µm).

The respirable dry powders and/or respirable dry particles of Formulations I to V and/or the Expanded Tiotropium Formulations are dispersible, and have 1 bar/4 bar and/or 0.5 bar/4 bar ratio of less than about 2.0 (e.g., about 0.9 to less than about 2), about 1.7 or less (e.g., about 0.9 to about 1.7) about 1.5 or less (e.g., about 0.9 to about 1.5), about 1.4 or less (e.g., about 0.9 to about 1.4), or about 1.3 or less (e.g., about 0.9 to about 1.3), and preferably have a 1 bar/4 bar and/or a 0.5 bar/4 bar of about 1.5 or less (e.g., about 1.0 to about 1.5), and/or about 1.4 or less (e.g., about 1.0 to about 1.4).

The respirable dry powders and/or respirable dry particles of Formulations I to V and/or the Expanded Tiotropium Formulations preferably have a tap density of at least about 0.45 g/cm$^3$ (e.g., about 0.45 g/cm$^3$ to about 1.2 g/cm$^3$), at least about 0.5 g/cm$^3$ (e.g., about 0.5 g/cm$^3$ to about 1.2 g/cm$^3$), at least about 0.55 g/cm$^3$ (e.g., about 0.55 g/cm$^3$ to about 1.2 g/cm$^3$), at least about 0.6 g/cm$^3$ (e.g., about 0.6 g/cm$^3$ to about 1.2 g/cm$^3$), or at least about 0.6 g/cm$^3$ to about 1.0 g/cm$^3$.

Also, the respirable dry powders and/or respirable dry particles of Formulations I to V and/or the Expanded Tiotropium Formulations may have a tap density of at least about 0.4 g/cm$^3$, a tap density of greater than 0.4 g/cm$^3$, or a tap density greater than 0.4 g/cm$^3$ to about 1.2 g/cm$^3$.

The respirable dry powders and/or respirable dry particles of Formulations I to V and/or the Expanded Tiotropium Formulations have an MMAD of less than 10 microns (e.g., about 0.5 microns to less than 10 microns), preferably an MMAD of about 5 microns or less (e.g., about 1 micron to about 5 microns), about 2 microns to about 5 microns, or about 2.5 microns to about 4.5 microns. In a preferred embodiment, the MMAD is measured using a capsule based passive dry powder inhaler (RS01 Model 7, High resistance Plastiape S.p.A.), which had specific resistance of 0.036 sqrt(kPa)/liters per minute, and as measured at 60 LPM, the preferred MMAD range is about 2.9 microns to about 4.0 microns, and the most preferred MMAD range is about 2.9 microns to about 3.5 microns.

In another preferred embodiment, the MMAD is measured using a capsule based passive dry powder inhaler RS01 UHR2 (RS01 Model 7, Ultrahigh resistance 2 (UHR2) Plastiape S.p.A.), which had specific resistance of 0.048 sqrt(kPa)/liters per minute, and as measured at 39 LPM, the preferred MMAD range is about 3.0 microns to about 5.0 microns, and the most preferred MMAD range is about 3.8 microns to about 4.3 microns.

The respirable dry powders and/or respirable dry particles of Formulations I to V and/or the Expanded Tiotropium Formulations have an FPF of less than about 5.6 microns (FPF<5.6 µm) of the total dose of at least about 35%, preferably at least about 45%, at least about 60%, between about 45% to about 80%, or between about 60% and about 80%.

In addition, the respirable dry powders and/or respirable dry particles of Formulations I to V and/or the Expanded Tiotropium Formulations preferably have a FPF of less than about 3.4 microns (FPF<3.4 µm) of the total dose of at least about 20%, preferably at least about 25%, at least about 30%, at least about 40%, between about 25% and about 60%, or between about 40% and about 60%.

The respirable dry powders and/or respirable dry particles of Formulations I to V and/or the Expanded Tiotropium Formulations have a FPD of less than about 4.4 microns (FPD<4.4 µm) of between about 1 microgram and about 5 micrograms, or about 2.0 micrograms and about 5.0 micrograms.

The respirable dry powders and/or respirable dry particles of Formulations I to V and/or the Expanded Tiotropium Formulations have a FPD of less than about 4.4 microns (FPD<4.4 µm) as a percentage of the total dose of at least 30%, at least 35%, at least 40%, at least 45%, at least 50%, at least 55%, or at least 60%.

In some aspects, the invention provides a method of efficiently delivering a dose of tiotropium as a dry powder. The efficiency of delivering a dose of tiotropium can be characterized based on delivering an effective amount of tiotropium to the lungs with a lower nominal dose filled into the capsule than from a standard dry powder formulation such as SPIRIVA (tiotropium bromide) HANDIHALER (dry powder inhaler) which has a nominal dose of 18 micrograms of tiotropium. The efficiency of delivering a dose of tiotropium can further be characterized by delivering a fine particle dose similar to that of a capsule of SPIRIVA (tiotropium bromide) HANDIHALER (dry powder inhaler) with a lower nominal dose filled into the capsule. The efficiency of delivering a dose of tiotropium can further be characterized by delivering a fine particle dose less than about 4.4 microns (FPD<4.4 µm) similar to that of a capsule of SPIRIVA (tiotropium bromide) HANDIHALER (dry powder inhaler) with a lower nominal dose filled into the capsule.

The efficiency of delivering a dose of tiotropium can be further characterized in an aspect of the current invention based on delivering an effective amount of tiotropium to the lungs to achieve a similar improvement in lung function, preferably, a similar change in forced expiratory volume in one second ($FEV_1$), or, more preferably, a similar change in trough $FEV_1$ response at steady state as SPIRIVA (tiotropium bromide) HANDIHALER (dry powder inhaler), but with a lower nominal dose than SPIRIVA (tiotropium bromide) HANDIHALER (dry powder inhaler). In one aspect, when measured in patients being administered the respirable dry powders and/or respirable dry particles of Formulations I to V and/or the Expanded Tiotropium Formulations in the current invention; when the nominal dose of tiotropium in the respirable dry powders and/or respirable dry particles of Formulations I to V and/or the Expanded Tiotropium Formulations is 70% or less, 50% or less, or preferably 35% or less, 25% or less, or 20% or less, 15% or less, 10% or less, or 5% or less of the nominal dose of SPIRIVA (tiotropium bromide) HANDIHALER (dry powder inhaler), which is 18 micrograms of tiotropium; the change in $FEV_1$ is about 80% or greater of the change in $FEV_1$ observed in patients taking SPIRIVA (tiotropium bromide) HANDIHALER (dry powder inhaler), preferably, about 85% or greater of the change in $FEV_1$ observed in patients taking SPIRIVA (tiotropium bromide) HANDIHALER (dry powder inhaler), more preferably, 90% or greater of the change in $FEV_1$ observed for patients taking SPIRIVA (tiotropium bromide) HANDIHALER (dry powder inhaler), or most preferably, about 95% or greater of the change in $FEV_1$ observed in patients taking SPIRIVA (tiotropium bromide) HANDIHALER (dry powder inhaler).

In another aspect, when measured in patients being administered the respirable dry powders and/or respirable dry particles of Formulations I to V and/or the Expanded Tiotropium Formulations in the current invention; when the nominal dose of tiotropium in the respirable dry powders and/or respirable dry particles of Formulations I to V and/or the Expanded Tiotropium Formulations is 70% or less, 50% or less, or preferably 35% or less, 25% or less; or 20% or less, 15% or less, 10% or less, or 5% or less of the nominal dose of SPIRIVA (tiotropium bromide) HANDIHALER (dry powder inhaler), which is 18 micrograms of tiotropium; the change in trough $FEV_1$ response at steady state is about 80% or greater of the change in trough $FEV_1$ response at steady state observed in patients taking SPIRIVA (tiotropium bromide) HANDIHALER (dry powder inhaler), preferably, about 85% or greater of the change in trough $FEV_1$ response at steady state observed in patients taking SPIRIVA (tiotropium bromide) HANDIHALER (dry powder inhaler), more preferably, 90% or greater of the change in trough $FEV_1$ response at steady state observed for patients taking SPIRIVA (tiotropium bromide) HANDIHALER (dry powder inhaler), or most preferably, about 95% or greater of the change in trough $FEV_1$ response at steady state observed in patients taking SPIRIVA (tiotropium bromide) HANDIHALER (dry powder inhaler).

In another aspect, when measured in patients being administered the respirable dry powders and/or respirable dry particles of Formulations I to V and/or the Expanded Tiotropium Formulations in the current invention; when the nominal dose of tiotropium in the respirable dry powders and/or respirable dry particles of Formulations I to V and/or the Expanded Tiotropium Formulations is 70% or less, 50% or less, or preferably 35% or less, 25% or less; or, 20% or less, 15% or less, 10% or less, or 5% or less of the nominal dose of SPIRIVA (tiotropium bromide) HANDIHALER (dry powder inhaler), which is 18 micrograms of tiotropium; the change in trough $FEV_1$ response at steady state is about 80 mL or greater, about 90 mL or greater, preferably about 100 mL or greater, about 110 mL or greater, about 120 mL or greater.

The respirable dry powders and/or respirable dry particles of Formulations I to V and/or the Expanded Tiotropium Formulations can be contained in a receptacle that may contain about 15 mg, 10 mg, 7.5 mg, 5 mg, 2.5 mg, or 1 mg of mass of the respirable dry powder. Such receptacles may contain a nominal dose of tiotropium that ranges between about 3 to about 12 micrograms, between about 3 to about 9 micrograms, or between about 3 to about 6 micrograms. In certain embodiments, the receptacle may contain a nominal dose of tiotropium of about 3 micrograms, about 6 micrograms, about 9 micrograms, or about 12 micrograms. The receptacle can be contained in a dry powder inhaler or can be packaged and/or sold separately.

Furthermore, the receptacles may contain a nominal dose of tiotropium that ranges between about 1.5 micrograms and 12 micrograms. In a certain embodiment, the receptacle may contain a nominal dose of tiotropium of about 2 micrograms.

Furthermore, the receptacles may contain a nominal dose of tiotropium that ranges from about 0.5 micrograms to about 6 micrograms, or from about 0.5 micrograms to about 3 micrograms, or from about 1 microgram to about 3 micrograms. In a certain embodiment, the receptacle may contain a nominal dose of tiotropium of about 0.5 micrograms, about 1 microgram, about 1.5 micrograms, or about 2.5 micrograms.

The respirable dry powders and/or respirable dry particles of Formulations I to V and/or the Expanded Tiotropium Formulations can have a water or solvent content of up to about 15% by weight of the respirable dry powder or particle. For example, the water or solvent content is up to about 10%, up to about 5%, or preferably between about 0.1% and about 3%, between about 0.01% and 1%, or be substantially free of water or other solvent, or be anhydrous.

The respirable dry powders and/or respirable dry particles of Formulations I to V and/or the Expanded Tiotropium Formulations can be administered with low inhalation energy. In order to relate the dispersion of powder at different inhalation flow rates, volumes, and from inhalers of different resistances, the energy required to perform the inhalation maneuver can be calculated. Inhalation energy can be calculated from the equation $E=R^2Q^2V$ where E is the inhalation energy in Joules, R is the inhaler resistance in $kPa^{1/2}$/LPM, Q is the steady flow rate in L/min and V is the inhaled air volume in L.

The respirable dry powders and/or respirable dry particles of Formulations I to V and/or the Expanded Tiotropium Formulations are characterized by a high emitted dose (e.g., CEPM of at least 75%, at least 80%, at least 85%, at least 90%, at least 95%) from a dry powder inhaler when a total inhalation energy of less than about 5 Joules, less than about 3.5 Joules, less than about 2.4 Joules, less than about 2 Joules, less than about 1 Joule, less than about 0.8 Joule, less than about 0.5 Joule, or less than about 0.3 Joule is applied to the dry powder inhaler. For example, an emitted dose of at least 75%, at least 80%, at least 85%, at least 90%, at least 95% CEPM of any one of Formulations I to V contained in a unit dose container, containing about 4 mg or more, about 6 mg or more, about 11 mg or more, about 15 mg or more, about 20 mg or more, about 30 mg or more, or about 4 mg to about 6 mg, about 6 mg to about 11 mg, about 11 mg to about 15 mg, or about 15 mg to about 20 mg of the appropriate formulation, in a dry powder inhaler can be achieved when a total inhalation energy of less than about 5 Joules, less than about 3.5 Joules, less than about 2 Joules, less than about 1 Joule, less than about 0.8 Joule, less than about 0.5 Joule, or less than about 0.3 Joule is applied to the dry powder inhaler.

In one aspect, The respirable dry powders and/or respirable dry particles of Formulations I to V and/or the Expanded Tiotropium Formulations are characterized by a capsule emitted powder mass of at least 80% when emitted from a passive dry powder inhaler that has a resistance of about 0.036 sqrt(kPa)/liters per minute under the following conditions: an inhalation energy of 2.3 Joules at a flow rate of 30 LPM using a size 3 capsule that contains a total mass of 10 mg, said total mass consisting of the respirable dry particles of any one of Formulations I to V, and wherein the volume median geometric diameter of the respirable dry particles emitted from the inhaler is 5 microns or less.

The dry powder can fill the unit dose container, or the unit dose container can be at least 2% full, at least 5% full, at least 10% full, at least 20% full, at least 30% full, least 40% full, at least 50% full, at least 60% full, at least 70% full, at least 80% full, or at least 90% full. The unit dose container can be a capsule (e.g., size 000, 00, 0E, 0, 1, 2, 3, and 4, with respective volumetric capacities of 1.37 ml, 950 μl, 770 μl, 680 μl, 480 μl, 360 μl, 270 μl, and 200 μl). The capsule is preferably between about 2% full and about 10% full, between about 10% full and about 20% full. The unit dose container can be a blister. The blister can be packaged as a single blister, or as part of a set of blisters, for example, 7 blisters, 14 blisters, 28 blisters, or 30 blisters. The one or more blister is preferably at least 30% full, at least 50% full, or at least 70% full.

Healthy adult populations are predicted to be able to achieve inhalation energies ranging from 2.9 Joules for comfortable inhalations to 22 Joules for maximum inhalations by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa$^{1/2}$/LPM, with an inhalation volume of 2 L based on both FDA guidance documents for dry powder inhalers and on the work of Tiddens et al. (Journal of Aerosol Med, 19(4), p. 456-465, 2006) who found adults averaging 2.2 L inhaled volume through a variety of DPIs.

Mild, moderate and severe adult COPD patients are predicted to be able to achieve maximum inhalation energies of 5.1 to 21 Joules, 5.2 to 19 Joules, and 2.3 to 18 Joules respectively. This is again based on using measured PIFR values for the flow rate Q in the equation for inhalation energy. The PIFR achievable for each group is a function of the inhaler resistance that is being inhaled through. The work of Broeders et al. (Eur Respir J, 18, p. 780-783, 2001) was used to predict maximum and minimum achievable PIFR through 2 dry powder inhalers of resistances 0.021 and 0.032 kPa$^{1/2}$/LPM for each.

Similarly, adult asthmatic patients are predicted to be able to achieve maximum inhalation energies of 7.4 to 21 Joules based on the same assumptions as the COPD population and PIFR data from Broeders et al.

Healthy adults and children, COPD patients, asthmatic patients ages 5 and above, and CF patients, for example, are capable of providing sufficient inhalation energy to empty and disperse the dry powder formulations of the invention.

An advantage of the invention is the production of powders that disperse well across a wide range of flow rates and are relatively flowrate independent. The respirable dry particles and respirable dry powders of the invention enable the use of a simple, passive DPI for a wide patient population.

In particular aspects, the invention is a respirable dry powder containing respirable dry particles of any one of Formulations I to V. In a further particular aspect, the respirable dry powder containing respirable dry particles comprise i) about 79.5% to about 80.5% sodium chloride, ii) about 19.5% to about 20.5% leucine, and iii) about 0.01% to about 0.5% tiotropium bromide, with all values are weight percentages. In an additional particular aspect, the invention is a respirable dry powder containing respirable dry particles that contain Expanded Tiotropium Formulations.

The respirable dry powder containing respirable dry particles of any one of formulations in the previous paragraph or falling in any one of the formulation ranges in the previous paragraph are characterized by:

1. VMGD at 1 bar as measured using a HELOS/RODOS system is about 10 microns or less, preferably between about 1 micron and about 5 microns, between about 1 micron and about 4.0 microns, or between about 1.5 microns and about 3.5 microns;
2. 1 bar/4 bar of about 1.5 or less, about 1.4 or less, or between about 1 and about 1.5, or between about 1 and about 1.4;
3. 0.5 bar/4 bar of about 1.5 or less, about 1.4 or less, or between about 1 and about 1.5, or between about 1 and about 1.4;
4. tap density of about 0.45 g/cm$^3$ or greater, between about 0.45 g/cm$^3$ and about 1.2 g/cm$^3$, between 0.5 g/cm$^3$ and about 1.2 g/cm$^3$, between 0.55 g/cm$^3$ and about 1.1 g/cm$^3$, or between 0.6 g/cm$^3$ and about 1 g/cm$^3$;
5. MMAD of about 10 microns or less, preferably between about 1 micron and about 5 microns, or between about 2.5 microns to about 4.5 microns;
6. FPF<5.6 of at least about 45%, at least about 60%, or between about 60% and about 80%;
7. FPF<4.4 of at least about 35%, at least about 50%, or between about 50% and about 70%;
8. FPF<3.4 of at least about 25%, at least about 40%, or between about 40% and about 60%;
9. FPD<4.4 of between about 1 microgram and about 5 micrograms of tiotropium, or between about 2.0 micrograms and about 5.0 micrograms of tiotropium; and/or
10. Ratio of the fine particle dose less than 2.0 microns to the fine particle dose less than 4.4 microns of less than about 0.50, less than about 0.35, or less than about 0.25.

The respirable dry powder or respirable dry particles described above can be further characterized by a water content of less than 15% by weight, preferably less than 10%, less than 5%, or most preferably less than 1%, all by weight. In addition, the respirable dry powder or respirable dry particles of any one of Formulations I to V are characterized by a capsule emitted powder mass of at least 80% when emitted from a passive dry powder inhaler that has a resistance of about 0.036 sqrt(kPa)/liters per minute under the following conditions: an inhalation energy of 2.3 Joules at a flow rate of 30 LPM using a size 3 capsule that contains a total mass of 10 mg, said total mass consisting of the respirable dry particles of any one of Formulations I to V, and wherein the volume median geometric diameter of the respirable dry particles emitted from the inhaler is 5 microns or less.

In another particular aspect, the invention is a respirable dry powder containing respirable dry particles of a formulation falling within one of the following ranges or specifically identified formulation:

about 60% to about 90% sodium chloride, about 10% to about 40% leucine, about 0.01% to about 0.5% tiotropium, and optionally one or more additional therapeutic agents up to about 20%;

about 65% to about 86% sodium chloride, about 10% to about 35% leucine, about 0.01% to about 0.5% tiotropium, and optionally one or more additional therapeutic agents up to about 20%;

preferably, about 67% to about 84% sodium chloride, about 12% to about 28% leucine, about 0.01 to about 0.5% tiotropium, and optionally one or more additional therapeutic agent up to about 20%;

more preferably, about 75% to about 82% sodium chloride, about 15% to about 25% leucine, about 0.01 to about 0.5% tiotropium, and optionally one or more additional therapeutic agent up to about 20%; or most preferably, about 79.5% to about 80.5% sodium chloride, about 19.5% to about 20.5% leucine, about 0.01 to about 0.5% tiotropium; or Formulation I-V, where the weight percent of each component is listed below in Table 1A:

TABLE 1A

Tiotropium formulations

Composition (wt %, dry basis)

| Formulation | Tiotropium | Leucine | Sodium Chloride |
|---|---|---|---|
| I | 0.04 | 19.99 | 79.97 |
| II | 0.07 | 19.99 | 79.94 |
| III | 0.11 | 19.98 | 79.91 |
| IV | 0.14 | 19.97 | 79.89 |
| V | 0.22 | 19.96 | 79.82 | where all values are weight percent, and all of the components of any particular formulation adds up to 100%; where the tiotropium is preferably present in an amount between about 0.02 and 0.25%, by weight on a dry basis, and where the one or more additional therapeutic agent is preferably present in an amount between about 0.01% to about 10%. Preferably, the additional therapeutic agent is an inhaled corticosteroid (ICS). More preferably, the ICS is chosen to match the dosing regimen of tiotropium, which is administered once per day (QD), for example, as indicated in the SPIRIVA (tiotropium bromide) HANDIHALER (dry powder inhaler) package insert. The preferred inhaled corticosteroids are fluticasone, such as fluticasone furoate, mometasone, such as mometasone furoate, ciclesonide, and the like; and the more preferred inhaled corticosteroids are fluticasone furoate, mometasone furoate, or ciclesonide. The preferred weight percentages on a dry basis of these inhaled corticosteroids are from about 0.2% to about 4% for fluticasone furoate, from about 0.4% to about 10% for mometasone furoate, and from about 0.2% to about 5% for ciclesonide. In a preferred aspect, only one ICS is used in the formulation.

In one aspect, the weight ratio between sodium chloride and leucine is about 4:1. In one aspect, the respirable dry powder consists of respirable dry particles. In another aspect, the formulation does not contain another therapeutic agent besides tiotropium.

The respirable dry powder comprising respirable dry particles described by any of the ranges or specifically disclosed formulations in the previous paragraph are characterized by:

1. VMGD at 1 bar as measured using a HELOS/RODOS system is about 10 microns or less, preferably between about 1 micron and about 5 microns, between about 1.0 micron and about 4.0 microns, or between about 1.5 microns and about 3.5 microns, or between 2 microns and 5 microns, or between 2.5 microns and 4.5 microns;
2. 1 bar/4 bar of about 1.5 or less, about 1.4 or less, about 1.3 or less, or between about 1 and about 1.5, or between about 1 and about 1.4, or between about 1 and about 1.3;
3. 0.5 bar/4 bar of about 1.5 or less, about 1.4 or less, about 1.3 or less, or between about 1 and about 1.5, or between about 1 and about 1.4, or between about 1 and about 1.3;
4. tap density of greater than 0.4 g/cm$^3$, greater than 0.4 g/cm$^3$ to about 1.2 g/cm$^3$, about 0.45 g/cm$^3$ or greater, between about 0.45 g/cm$^3$ and about 1.2 g/cm$^3$, between 0.5 g/cm$^3$ and about 1.2 g/cm$^3$, between 0.55 g/cm$^3$ and about 1.1 g/cm$^3$, or between 0.6 g/cm$^3$ and about 1 g/cm$^3$;
5. MMAD of about 10 microns or less, preferably between about 1 micron and about 5 microns, between about 2.5 microns to about 4.5 microns, or between 3.0 microns and 5.0 microns;
6. FPF<5.0 of at least about 45%, at least about 60%, or between about 60% and about 80%;
7. FPF<4.4 of at least about 35%, at least about 50%, or between about 50% and about 70%;
8. FPF<3.4 of at least about 25%, at least about 40%, or between about 40% and about 60%;
9. FPD<4.4 of between about 1 microgram and about 5 micrograms of tiotropium, between about 2.0 micrograms and about 5.0 micrograms of tiotropium, or, preferably, between about 2.0 micrograms and about 4.0 micrograms;
10. FPD<5.0 of between about 1 microgram and about 5 micrograms of tiotropium, between about 2.0 micrograms and about 5.0 micrograms of tiotropium, or, preferably, between about 2.0 micrograms and about 4.0 micrograms;
11. Ratio of the fine particle dose less than 2.0 microns to the fine particle dose less than 4.4 microns of less than about 0.50, less than about 0.35, less than about 0.30; preferably, less than about 0.25, less than about 0.20, less than about 0.18, or about 0.15 or less;
12. Ratio of the fine particle dose less than 2.0 microns to the fine particle dose less than 5.0 microns of less than about 0.50, less than about 0.35, less than about 0.30; preferably, less than about 0.25, less than about 0.20, less than about 0.18, or about 0.15 or less;
13. A water content, on a weight basis, of less than 15%, less than 10%, preferably less than 5%, or most preferably less than 1%;
14. A CEPM of at least 80% when emitted from a passive dry powder inhaler that has a resistance of about 0.036 sqrt(kPa)/liters per minute under the following conditions: an inhalation energy of 2.3 Joules at a flow rate of 30 LPM using a size 3 capsule that contains a total mass of 10 mg of the respirable dry powder comprising respirable dry particles described by any of the ranges or specifically disclosed formulations in the previous paragraph, and wherein the VMGD of the respirable dry particles emitted from the inhaler is 5 microns or less;
15. A emitted dose of at least 70%, at least 75%, at least 80%, or at least 85% when emitted from a passive dry powder inhaler that has a resistance of about 0.036 sqrt(kPa)/liters per minute under the following conditions: an inhalation energy of 2.3 Joules at a flow rate of 30 LPM using a size 3 capsule that contains a total mass of 10 mg of the respirable dry powder comprising respirable dry particles described by any of the ranges or specifically disclosed formulations in the previous paragraph, and wherein the VMGD of the respirable dry particles emitted from the inhaler is 5 microns or less;
16. A CEPM of at least 80% when emitted from a passive dry powder inhaler that has a resistance of about 0.048 sqrt(kPa)/liters per minute under the following conditions: an inhalation energy of 1.8 Joules at a flow rate of 20 LPM using a size 3 capsule that contains a total mass of 5 mg of the respirable dry powder comprising respirable dry particles described by any of the ranges or specifically disclosed formulations in the previous paragraph, and wherein the VMGD of the respirable dry particles emitted from the inhaler is 5 microns or less; and/or
17. A emitted dose of at least 65%, at least 70%, at least 75%, at least 80%, or at least 85% when emitted from a passive dry powder inhaler that has a resistance of about 0.048 sqrt(kPa)/liters per minute under the following conditions: an inhalation energy of 1.8 Joules at a flow rate of 20 LPM using a size 3 capsule that contains a total mass of 5 mg of the respirable dry powder comprising respirable dry particles described by any of the ranges or specifically disclosed formulations in the previous paragraph, and wherein the VMGD of the respirable dry particles emitted from the inhaler is 5 microns or less.

The respirable dry powder comprising respirable dry particles described by any of the ranges or specifically disclosed formulations, characterized in the previous paragraph, may be filled into a receptacle, for example a capsule or a blister. When the receptacle is a capsule, the capsule is, for example, a size 2 or a size 3 capsule, and is preferably a size 3 capsule. The capsule material may be, for example, gelatin or HPMC (Hydroxypropyl methylcellulose), and is preferably HPMC.

The respirable dry powder comprising respirable dry particles described and characterized above may be contained in a dry powder inhaler (DPI). The DPI may be a capsule-based DPI or a blister-based DPI, and is preferably a capsule-based DPI. More preferably, the dry powder inhaler is selected from the RS01 family of dry powder inhalers (Plastiape S.p.A., Italy). More preferably, the dry powder inhaler is selected from the RS01 HR or the RS01 UHR2. Most preferably, the dry powder inhaler is the RS01 UHR2. In one aspect, the dry powder inhaler is not the RS01 HR.

When the respirable dry powder comprising respirable dry particles described and characterized above is contained in a receptacle, the receptacle may contain a mass of the respirable dry powder comprising respirable dry particles between about 8 mg and about 12 mg, between about 5.5 mg and about 9.5 mg, between about 3.5 mg and about 6.5 mg, between about 1.5 mg and 4.5 mg, or between 0.5 mg and 2.5 mg; and, preferably, between about 3.5 mg and about 6.5 mg; or about 15 milligrams, about 10 milligrams, about 7.5 milligrams, about 5 milligrams, about 2.5 milligrams, or about 1 milligrams; preferably, a mass of about 5 milligrams. Alternatively or additionally, when the respirable dry powder comprising respirable dry particles is contained in a receptacle, the receptacle may contain a nominal dose of tiotropium between about 1.5 micrograms to about 12 micrograms, between about 3 to about 12 micrograms, between about 3 to about 6 micrograms; preferably, from about 0.5 micrograms to about 6 micrograms, or from about 0.5 micrograms to about 3 micrograms, or about 1 microgram to about 3 micrograms; or a nominal dose of tiotropium of about 12 micrograms, about 9 micrograms, preferably, about 6 micrograms, about 4 micrograms; or, more preferably about 3 micrograms, about 2 micrograms or about 1 microgram.

When the respirable dry powder comprising respirable dry particles described and characterized above is administered to a patient; when the nominal dose of tiotropium is 70% or less, 50% or less, or preferably 35% or less, 25% or less; or 20% or less, 15% or less, 10% or less, or 5% or less of the nominal dose of SPIRIVA (tiotropium bromide) HANDIHALER (dry powder inhaler), which is 18 micrograms of tiotropium; the change in trough $FEV_1$ response at steady state is about 80% or greater of the change in trough $FEV_1$ response at steady state observed in patients taking SPIRIVA (tiotropium bromide) HANDIHALER (dry powder inhaler), preferably, about 85% or greater of the change in trough $FEV_1$ response at steady state observed in patients taking SPIRIVA (tiotropium bromide) HANDIHALER (dry powder inhaler), more preferably, 90% or greater of the change in trough $FEV_1$ response at steady state observed for patients taking SPIRIVA (tiotropium bromide) HANDIHALER (dry powder inhaler), or most preferably, about 95% or greater of the change in trough $FEV_1$ response at steady state observed in patients taking SPIRIVA (tiotropium bromide) HANDIHALER (dry powder inhaler). Alternatively or in addition, when the respirable dry powder comprising respirable dry particles described and characterized above is administered to a patient; when the nominal dose of tiotropium is 70% or less, 50% or less, or preferably 35% or less, 25% or less; or, 20% or less, 15% or less, 10% or less, or 5% or less of the nominal dose of SPIRIVA (tiotropium bromide) HANDIHALER (dry powder inhaler), which is 18 micrograms of tiotropium; the change in trough $FEV_1$ response at steady state is about 80 mL or greater, about 90 mL or greater, preferably about 100 mL or greater, about 110 mL or greater, about 120 mL or greater. The patient described above may be a patient with a respiratory disease, such as COPD, chronic bronchitis, emphysema, asthma, cystic fibrosis, or non-cystic fibrosis bronchiectasis. Preferably, the respiratory disease is COPD, chronic bronchitis, and/or emphysema. The respirable dry powder comprising respirable dry particles described and characterized above may be administered to a patient to reduce the incidence or severity of an acute exacerbation of a respiratory disease, to relieve the symptoms of a respiratory disease, and/or to improve the lung function of a patient with a respiratory disease.

Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, spray-freeze drying, milling (e.g., jet milling), blending, solvent extraction, solvent evaporation, phase separation, simple and complex coacervation, interfacial polymerization, suitable methods that involve the use of supercritical carbon dioxide ($CO_2$), sonocrystalliztion, nanoparticle aggregate formation and other suitable methods, including combinations thereof. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

Suitable methods for selecting respirable dry particles with desired properties, such as size and density, include wet sieving, dry sieving, and aerodynamic classifiers (such as cyclones).

The respirable dry particles are preferably spray dried. Suitable spray-drying techniques are described, for example, by K. Masters in "Spray Drying Handbook", John Wiley & Sons, New York (1984). Generally, during spray-drying, heat from a hot gas such as heated air or nitrogen is used to evaporate a solvent from droplets formed by atomizing a continuous liquid feed. When hot air is used, the moisture in the air is at least partially removed before its use. When nitrogen is used, the nitrogen gas can be run "dry", meaning that no additional water vapor is combined with the gas. If desired the moisture level of the nitrogen or air can be set before the beginning of spray dry run at a fixed value above "dry" nitrogen. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. The nozzle can be a two-fluid nozzle, which is in an internal mixing setup or an external mixing setup. Alternatively, a rotary atomizer having a 4- or 24-vaned wheel may be used. Examples of suitable spray dryers that can be outfitted with either a rotary atomizer or a nozzle, include, a Mobile Minor Spray Dryer or the Model PSD-1, both manufactured by GEA Niro, Inc. (Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C., and preferably is about 220° C. to about 285° C. Another preferable range is between 130° C. to about 200° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. Another preferable range is between 65° C. to about 110° C., preferably about 75° C. to about 100° C. If desired, the respirable dry particles that are produced can be fractionated by volumetric size, for example, using a sieve, or fractioned by aerodynamic size, for example, using a cyclone, and/or further separated according to density using techniques known to those of skill in the art.

Additional examples of spray dryers include the ProCepT Formatrix R&D spray dryer (ProCepT nv, Zelzate, Belgium). BüCHI B-290 MINI SPRAY DRYER (BüCHI Labortechnik AG, Flawil, Switzerland). An additional preferred range for the inlet temperature to the spray dryer is about 180° C. to about 285° C. An additional preferred range for the outlet temperature from the spray dryer is about 40° C. to about 110° C., more preferably about 50° C. to about 90° C.

To prepare the respirable dry particles of the invention, generally, a solution, emulsion or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feed stock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer. Alternatively, the atomizing step is performed on a bulk mixed solution.

The feed stock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions.

The feed stock or components of the feed stock can have any desired pH, viscosity or other properties. If desired, a pH buffer can be added to the solvent or co-solvent or to the formed mixture. Generally, the pH of the mixture ranges from about 3 to about 8.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD.

The invention also relates to respirable dry powders or respirable dry particles produced by preparing a feedstock solution, emulsion or suspension and spray drying the feedstock according to the methods described herein. The feedstock can be prepared using (a) sodium chloride in an amount of about 79.5% to about 80.5% by weight (e.g., of total solutes used for preparing the feedstock) and (b) leucine in an amount of at least about 19.5% to about 20.5% by weight (e.g., of total solutes used for preparing the feedstock) and tiotropium bromide in an amount of about 0.01% to about 0.5% by weight (e.g., of total solutes used for preparing the feedstock). All weight percentages are given on a dry (anhydrous) basis.

In an embodiment, the respirable dry powders or respirable dry particles of the invention can be obtained by (1) preparing a feedstock comprising (a) a dry solute containing in percent by weight of the total dry solute about 79.5% to about 80.5% sodium chloride, about 19.5% to about 20.5% leucine, and about 0.01% to about 0.5% tiotropium bromide, and (b) one or more suitable solvents for dissolution of the solute and formation of the feedstock, and (2) spray drying the feedstock. Various methods (e.g., static mixing, bulk mixing) can be used for mixing the solutes and solvents to prepare feedstocks, which are known in the art. If desired, other suitable methods of mixing may be used. For example, additional components that cause or facilitate the mixing can be included in the feedstock. For example, carbon dioxide produces fizzing or effervescence and thus can serve to promote physical mixing of the solute and solvents.

The diameter of the respirable dry particles, for example, their VMGD, can be measured using an electrical zone sensing instrument such as a Multisizer IIe (Coulter Electronic, Luton, Beds, England), or a laser diffraction instrument such as a HELOS system (Sympatec, Princeton, N.J.) or a Mastersizer system (Malvern, Worcestershire, UK). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Aerosol Particle Sizer (APS) Spectrometer (TSI Inc., Shoreview, Minn.) can be used to measure aerodynamic diameter. The APS measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor (ACI), next generation impactor (NGI), and the multi-stage liquid impinger (MSLI) methods. The methods and instruments for measuring particle aerodynamic diameter are well known in the art.

Tap density is a measure of the envelope mass density characterizing a particle. Tap density is accepted in the field as an approximation of the envelope mass density of a particle. The envelope mass density of a particle of a statistically isotropic shape is defined as the mass of the particle divided by the minimum sphere envelope volume within which it can be enclosed. Features which can contribute to low tap density include irregular surface texture, high particle cohesiveness and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopeia convention, Rockville, Md., $10^{th}$ Supplement, 4950-4951, 1999.

Fine particle fraction can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cut-offs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage. Specifically, an eight-stage ACI is calibrated so that the fraction of powder that is collected on stage 2 and all lower stages including the final collection filter is composed of respirable dry particles that have an aerodynamic diameter of less than 4.4 microns. The airflow at such a calibration is approximately 60 L/min.

If desired, a two-stage collapsed ACI can also be used to measure fine particle fraction. The two-stage collapsed ACI consists of only stages 0 and 2 of the eight-stage ACI, as well as the final collection filter, and allows for the collection of two separate powder fractions. Specifically, a two-stage collapsed ACI is calibrated so that the fraction of powder that is collected on stage two is composed of respirable dry particles that have an aerodynamic diameter of less than 5.6 microns and greater than 3.4 microns. The fraction of powder passing stage two and depositing on the final collection filter is thus composed of respirable dry particles having an aerodynamic diameter of less than 3.4 microns. The airflow at such a calibration is approximately 60 L/min.

The FPF(<5.6) has been demonstrated to correlate to the fraction of the powder that is able to make it into the lungs of the patient, while the FPF(<3.4) has been demonstrated to correlate to the fraction of the powder that reaches the deep lung of a patient. These correlations provide a quantitative indicator that can be used for particle optimization.

Emitted dose can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia convention, Rockville, Md., $13^{th}$ Revision, 222-225, 2007. This method utilizes an in vitro device set up to mimic patient dosing.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose.

Another way to approximate emitted dose is to determine how much powder leaves its container, e.g. capsule or blister, upon actuation of a dry powder inhaler (DPI). This takes into account the percentage leaving the capsule, but does not take into account any powder depositing on the DPI. The emitted powder mass is the difference in the weight of the capsule with the dose before inhaler actuation and the weight of the capsule after inhaler actuation. This measurement can be called the capsule emitted powder mass (CEPM) or sometimes termed "shot-weight".

A Multi-Stage Liquid Impinger (MSLI) is another device that can be used to measure fine particle fraction. The Multi-Stage Liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

The Next Generation Pharmaceutical Impactor (NGI) is a particle-classifying cascade impactor for testing metered-dose, dry-powder, and similar inhaler devices.

The geometric particle size distribution can be measured for the respirable dry powder after being emitted from a dry powder inhaler (DPI) by use of a laser diffraction instrument such as the Malvern Spraytec. With the inhaler mounted in the open-bench configuration, an airtight seal is made to the air inlet side of the DPI, causing the outlet aerosol to pass perpendicularly through the laser beam as an external flow. In this way, known flow rates can be blown through the DPI by positive pressure to empty the DPI. The resulting geometric particle size distribution of the aerosol is measured by the photodetectors with samples typically taken at 1000 Hz for the duration of the inhalation and the Dv50, GSD, FPF<5.0 μm measured and averaged over the duration of the inhalation.

Water content of the respirable dry powder or respirable dry particles can be measured by a Karl Fisher titration machine, or by a Thermogravimetric Analysis or Thermal Gravimetric Analysis (TGA). Karl Fischer titration uses coulometric or volumetric titration to determine trace amounts of water in a sample. TGA is a method of thermal analysis in which changes in weight of materials are measured as a function of temperature (with constant heating rate), or as a function of time (with constant temperature and/or constant mass loss). TGA may be used to determine the water content or residual solvent content of the material being tested.

The invention also relates to a respirable dry powder or respirable dry particles produced using any of the methods described herein.

The respirable dry particles of the invention can also be characterized by the chemical, physical, aerosol, and solid-state stability of the therapeutic agents and excipients that the respirable dry particles comprise. The chemical stability of the constituent salts can affect important characteristics of the respirable particles including shelf-life, proper storage conditions, and acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC).

Therapeutic Use and Methods

The respirable dry powders and respirable dry particles of the present invention are suited for administration to the respiratory tract. The dry powders and dry particles of the invention can be administered to a subject in need thereof for the treatment of respiratory (e.g., pulmonary) diseases, such as chronic bronchitis, emphysema, chronic obstructive pulmonary disease, asthma, airway hyper responsiveness, seasonal allergic allergy, bronchiectasis, cystic fibrosis, pulmonary parenchymal inflammatory conditions and the like, and for the treatment, reduction in incidence or severity, and/or prevention of acute exacerbations of these chronic diseases, such as exacerbations caused by viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Burkholderis* ssp., *Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, including pollen and cat dander, airborne particulates, and the like). In a preferred embodiment, the pulmonary disease is chronic bronchitis, emphysema, or chronic obstructive pulmonary disease. If desired, the respirable dry powders and respirable dry particles can be administered orally.

In another preferred embodiment, the pulmonary disease is asthma.

In some aspects, the invention is a method for treating pulmonary diseases, such as chronic bronchitis, emphysema, chronic obstructive pulmonary disease, asthma, airway hyper responsiveness, seasonal allergic allergy, bronchiectasis, cystic fibrosis and the like, comprising administering to the respiratory tract of a subject in need thereof an effective amount of respirable dry particles or dry powder, as described herein. In a preferred embodiment, the pulmonary disease is chronic bronchitis, emphysema, or chronic obstructive pulmonary disease.

In another preferred embodiment, the pulmonary disease is asthma.

In other aspects, the invention is a method for the treatment, reduction in incidence or severity, or prevention of acute exacerbations of a chronic pulmonary disease, such as chronic bronchitis, emphysema, chronic obstructive pulmonary disease, asthma, airway hyper responsiveness, seasonal allergic allergy, bronchiectasis, cystic fibrosis and the like, comprising administering to the respiratory tract of a subject in need thereof an effective amount of respirable dry particles or dry powder, as described herein. In a preferred embodiment, the pulmonary disease is chronic bronchitis, emphysema, or chronic obstructive pulmonary disease.

In another preferred embodiment, the pulmonary disease is asthma.

In other aspects, the invention is a method for reducing inflammation comprising administering to the respiratory tract of a subject in need thereof an effective amount of respirable dry particles or dry powders as described herein. Thus, the respirable dry particles and dry powders can be used to broadly prevent or treat acute and/or chronic inflammation and, in particular, inflammation that characterizes a number of pulmonary diseases and conditions including, chronic bronchitis, emphysema, chronic obstructive pulmonary disease (COPD), asthma, airway hyper responsiveness, seasonal allergic allergy, bronchiectasis, cystic fibrosis (CF), pulmonary parenchymal inflammatory diseases/conditions, and the like. In a preferred embodiment, the pulmonary disease is chronic bronchitis, emphysema, or chronic obstructive pulmonary disease. The dry particles and dry powders can be administered to prevent or treat both the inflammation inherent to diseases like COPD, asthma, and CF and the increased inflammation caused by acute exacerbations of the diseases, both of which play a primary role in the pathogenesis of those diseases.

In a preferred embodiment, the pulmonary disease is chronic bronchitis, emphysema, or chronic obstructive pulmonary disease. In another preferred embodiment, the pulmonary disease is asthma.

In other aspects, the invention is a method for relieving the symptoms of a respiratory disease and/or a chronic pulmonary disease, such as chronic bronchitis, emphysema, chronic obstructive pulmonary disease, asthma, airway hyper responsiveness, seasonal allergic allergy, bronchiectasis, cystic fibrosis and the like, comprising administering to the respiratory tract of a subject in need thereof an effective amount of respirable dry particles or dry powder, as described herein. In a preferred embodiment, the pulmonary disease is chronic bronchitis, emphysema, or chronic obstructive pulmonary disease. In another preferred embodiment, the pulmonary disease is asthma.

In other aspects, the invention is a method for improving lung function of a patient with a respiratory disease and/or a chronic pulmonary disease, such as chronic bronchitis, emphysema, chronic obstructive pulmonary disease, asthma, airway hyper responsiveness, seasonal allergic allergy, bronchiectasis, cystic fibrosis and the like, comprising administering to the respiratory tract of a subject in need thereof an effective amount of respirable dry particles or dry powder, as described herein. Without wishing to be bound by theory, improving a patient's lung function over a period of time is a long-term way to treat a respiratory disease and to prevent acute exacerbations. In a preferred embodiment, the pulmonary disease is chronic bronchitis, emphysema, or chronic obstructive pulmonary disease. In another preferred embodiment, the pulmonary disease is asthma.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, North Carolina), FlowCaps® (Hovione, Loures, Portugal), Inhalators® (Boehringer-Ingelheim, Germany), Aerolizer® (Novartis, Switzerland), high-resistance and low-resistance RS-01 (Plastiape, Italy) and others known to those skilled in the art.

The following scientific journal articles are incorporated by reference for their thorough overview of the following dry powder inhaler (DPI) configurations: 1) Single-dose Capsule DPI, 2) Multi-dose Blister DPI, and 3) Multi-dose Reservoir DPI. N. Islam, E. Gladki, "Dry powder inhalers (DPIs)—A review of device reliability and innovation", International Journal of Pharmaceuticals, 360(2008):1-11. H. Chystyn, "Diskus Review", International Journal of Clinical Practice, June 2007, 61, 6, 1022-1036. H. Steckel, B. Muller, "In vitro evaluation of dry powder inhalers I: drug deposition of commonly used devices", International Journal of Pharmaceuticals, 154(1997):19-29. Some representative capsule-based DPI units are RS-01 (Plastiape, Italy), Turbospin® (PH&T, Italy), Brezhaler® (Novartis, Switzerland), Aerolizer (Novartis, Switzerland), Podhaler® (Novartis, Switzerland), HandiHaler® (Boehringer Ingelheim, Germany), AIR® (Civitas, Mass.), Dose One® (Dose One, Me.), and Eclipse® (Rhone Poulenc Rorer). Some representative unit dose DPIs are Conix® (3M, Minnesota), Cricket® (Mannkind, Calif.), Dreamboat® (Mannkind, Calif.), Occoris® (Team Consulting, Cambridge, UK), Solis® (Sandoz), Trivair® (Trimel Biopharma, Canada), Twincaps® (Hovione, Loures, Portugal). Some representative blister-based DPI units are Diskus® (GlaxoSmithKline (GSK), UK), Diskhaler® (GSK), Taper Dry® (3M, Minnisota), Gemini® (GSK), Twincer® (University of Groningen, Netherlands), Aspirair® (Vectura, UK), AcuBreathe® (Respirics, Minnisota, USA), Exubra® (Novartis, Switzerland), Gyrohaler® (Vectura, UK), Omnihaler® (Vectura, UK), Microdose® (Microdose Therapeutix, USA), Multihaler® (Cipla, India) Prohaler® (Aptar), Technohaler® (Vectura, UK), and Xcelovair® (Mylan, Pa.). Some representative reservoir-based DPI units are Clickhaler® (Vectura), Next DPI® (Chiesi), Easyhaler® (Orion), Novolizer® (Meda), Pulmojet® (sanofi-aventis), Pulvinal® (Chiesi), Skyehaler® (Skyepharma), Duohaler® (Vectura), Taifun® (Akela), Flexhaler® (AstraZeneca, Sweden), Turbuhaler® (AstraZeneca, Sweden), and Twisthaler® (Merck), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 µl, 770 µl, 680 µl, 480 µl, 360 µl, 270 µl, and 200 µl) or other means that contain the dry particles or dry powders within the inhaler. Preferably, the blister has a volume of about 360 microliters or less, about 270 microliters or less, or more preferably, about 200 microliters or less, about 150 microliters or less, or about 100 microliters or less. Preferably, the capsule is a size 2 capsule, or a size 4 capsule. More preferably, the capsule is a size 3 capsule. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders are preferably administered in a single, breath-activated step using a passive DPI. When this type of device is used, the energy of the subject's inhalation both disperses the respirable dry particles and draws them into the respiratory tract.

The respirable dry particles or dry powders can be preferably delivered by inhalation to a desired area within the respiratory tract, as desired. It is well-known that particles with an aerodynamic diameter (MMAD) of about 1 micron to about 3 microns, can be delivered to the deep lung. Larger MMAD, for example, from about 3 microns to about 5 microns can be delivered to the central and upper airways. Therefore, without wished to be bound by theory, the invention has a MMAD of about 1 micron to about 5 microns, and preferentially, about 2.5 microns to about 4.5 microns, which preferentially deposits more of the therapeutic dose in the central airways than in the upper airways or in the deep lung.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors which contribute to oral deposition of a powder include the size distribution of the individual particles and the dispersibility of the powder. If the MMAD of the individual particles is too large, e.g. above 5 µm, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of 5 microns or less), the size distribution of the inhaled powder may have an MMAD of greater than 5 μm, leading to enhanced oral cavity deposition.

Therefore, it is desirable to have a powder in which the particles are small, dense, and dispersible such that the powders consistently deposit in the desired region of the respiratory tract. For example, the respirable dry powders comprising respirable dry particles have a MMAD of about 5 microns or less, between about 1 micron and about 5 microns, preferably between about 2.5 microns and about 4.5 microns; are dense particles, for example have a high tap density and/or envelope density are desired, such as about 0.45 g/cc or more, about 0.45 g/cc to about 1.2 g/cc, about 0.5 g/cc or more, about 0.55 g/cc or more, about 0.55 g/cc to about 1.0 g/cc, or about 0.6 g/cc to about 1.0 g/cc; and are highly dispersible (e.g. 1/4 bar or alternatively, 0.5/4 bar of less than about 2.0, and preferably about 1.5 or less, or about 1.4 or less). The tap density and/or envelop density and MMAD are related theoretically to the VMGD by means of the following formula: MMAD=VMGD*sqrt(envelope density or tap density). If it is desired to deliver a high mass of therapeutic using a fixed volume dosing container, then, particles of higher tap density and/or envelope density are desired.

The respirable dry powders comprising respirable dry particles may also have a tap density of at least about 0.4 g/cm$^3$, a tap density of greater than 0.4 g/cm$^3$, or a tap density of greater than 0.4 g/cm$^3$ to about 1.2 g/cm$^3$.

The respirable dry powders and respirable dry particles of the invention can be employed in compositions suitable for drug delivery via the respiratory system. For example, such compositions can include blends of the respirable dry particles of the invention and one or more other dry particles or powders, such as dry particles or powders that contain another active agent, or that consist of or consist essentially of one or more pharmaceutically acceptable excipients. The respirable dry powder can include blends of the dry particles with lactose, such as large lactose carrier particles that are greater than 10 microns, 20 microns to 500 microns, and preferably between 25 microns and 250 microns.

Respirable dry powders and respirable dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry powders or particles deposit in the deep lung. In another embodiment of the invention, delivery is primarily to the central airways. In another embodiment, delivery is to the upper airways. In a preferred embodiment, most of the mass of the respirable dry powders or particles deposit in the conducting airways.

Suitable intervals between doses that provide the desired therapeutic effect can be determined based on the severity of the condition, overall well being of the subject and the subject's tolerance to respirable dry particles and dry powders and other considerations. Based on these and other considerations, a clinician can determine appropriate intervals between doses. Generally, respirable dry particles and respirable dry powders are administered once, twice or three times a day, as needed.

If desired or indicated, the respirable dry particles and respirable dry powders described herein can be administered with one or more other therapeutic agents. The other therapeutic agents can be administered by any suitable route, such as orally, parenterally (e.g., intravenous, intra-arterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

EXEMPLIFICATION

Materials used in the following Examples and their sources are listed below. Sodium chloride, and L-leucine were obtained from Sigma-Aldrich Co. (St. Louis, Mo.), Spectrum Chemicals (Gardena, Calif.), or Merck (Darmstadt, Germany). Tiotropium bromide was obtained from RIA International (East Hanover, N.J.). Ultrapure (Type II ASTM) water was from a water purification system (Millipore Corp., Billerica, Mass.), or equivalent.

Methods:
Geometric or Volume Diameter.

Volume median diameter (x50 or Dv50), which may also be referred to as volume median geometric diameter (VMGD), was determined using a laser diffraction technique. The equipment consisted of a HELOS diffractometer and a RODOS dry powder disperser (Sympatec, Inc., Princeton, N.J.). The RODOS disperser applies a shear force to a sample of particles, controlled by the regulator pressure (typically set at 1.0 bar with maximum orifice ring pressure) of the incoming compressed dry air. The pressure settings may be varied to vary the amount of energy used to disperse the powder. For example, the dispersion energy may be modulated by changing the regulator pressure from 0.2 bar to 4.0 bar. Powder sample is dispensed from a microspatula into the RODOS funnel. The dispersed particles travel through a laser beam where the resulting diffracted light pattern produced is collected, typically using an R1 lens, by a series of detectors. The ensemble diffraction pattern is then translated into a volume-based particle size distribution using the Fraunhofer diffraction model, on the basis that smaller particles diffract light at larger angles. Using this method, geometric standard deviation (GSD) for the volume diameter was also determined.

Volume median diameter can also be measured using a method where the powder is emitted from a dry powder inhaler device. The equipment consisted of a Spraytec laser diffraction particle size system (Malvern, Worcestershire, UK), "Spraytec". Powder formulations were filled into size 3 HPMC capsules (Capsugel V-Caps) by hand with the fill weight measured gravimetrically using an analytical balance (Mettler Tolerdo XS205). A capsule based passive dry powder inhaler (RS01 Model 7, High resistance Plastiape S.p.A.) was used which had a specific resistance of 0.036 kPa$^{1/2}$LPM$^{-1}$. Flow rate and inhaled volume were set using a timer controlled solenoid valve with flow control valve (TPK2000, Copley Scientific). Capsules were placed in the dry powder inhaler, punctured and the inhaler sealed inside a cylinder. The cylinder was connected to a positive pressure air source with steady air flow through the system measured with a mass flow meter and its duration controlled with a timer controlled solenoid valve. The exit of the dry powder inhaler was exposed to room pressure and the resulting aerosol jet passed through the laser of the diffraction particle sizer (Spraytec) in its open bench configuration before being captured by a vacuum extractor. The steady air flow rate through the system was initiated using the solenoid valve and the particle size distribution was measured via the Spraytec at 1 kHz for the duration of the single inhalation maneuver with a minimum of 2 seconds. Particle size distribution parameters calculated included the volume median diameter (Dv50) and the geometric standard deviation (GSD) and the fine particle fraction (FPF) of particles less than 5 micrometers in diameter. At the completion of the inhalation duration, the dry powder inhaler was opened, the capsule removed and re-weighed to calculate the mass of powder that had been emitted from the capsule during the inhalation duration (capsule emitted powder mass or CEPM).

Fine Particle Fraction. The aerodynamic properties of the powders dispersed from an inhaler device were assessed with an Mk-II 1 ACFM Andersen Cascade Impactor (Copley Scientific Limited, Nottingham, UK) (ACI) or a Next Generation Impactor (Copley Scientific Limited, Nottingham, UK) (NGI). The ACI instrument was run in controlled environmental conditions of 18 to 25° C. and relative humidity (RH) between 25 and 35%. The instrument consists of eight stages that separate aerosol particles based on inertial impaction. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain, called the "final collection filter". Gravimetric and/or chemical analyses can then be performed to determine the particle size distribution. A short stack cascade impactor, also referred to as a collapsed cascade impactor, is also utilized to allow for reduced labor time to evaluate two aerodynamic particle size cut-points. With this collapsed cascade impactor, stages are eliminated except those required to establish fine and coarse particle fractions.

The impaction techniques utilized allowed for the collection of two or eight separate powder fractions. The capsules (HPMC, Size 3; Capsugel Vcaps, Peapack, N.J.) were hand filled with powder to a specific weight and placed in a hand-held, breath-activated dry powder inhaler (DPI) device, the high resistance RS01 DPI (Plastiape, Osnago, Italy). The capsule was punctured and the powder was drawn through the cascade impactor operated at a flow rate of 60.0 L/min for 2.0 s. At this flowrate, the calibrated cut-off diameters for the eight stages are 8.6, 6.5, 4.4, 3.3, 2.0, 1.1, 0.5 and 0.3 microns and for the two stages used with the short stack cascade impactor, based on the Andersen Cascade Impactor, the cut-off diameters are 5.6 microns and 3.4 microns. The fractions were collected by placing filters in the apparatus and determining the amount of powder that impinged on them by gravimetric measurements or chemical measurements on an HPLC. The fine particle fraction of the total dose of powder ($FPF_{TD}$) less than or equal to an effective cut-off aerodynamic diameter was calculated by dividing the powder mass recovered from the desired stages of the impactor by the total particle mass in the capsule. Results are reported for the eight-stage normal stack cascade impactor as the fine particle fraction of less than 4.4 microns ($FPF_{TD}<4.4$ microns) and the fine particle fraction of less than 2.0 microns ($FPF_{TD}<2.0$ microns), and the two-stage short stack cascade impactor as the fine particle fraction of less than 5.6 microns ($FPF_{TD}<5.6$ microns) and the fine particle fraction of less than 3.4 microns ($FPF_{TD}<3.4$ microns). The fine particle fraction can alternatively be calculated relative to the recovered or emitted dose of powder by dividing the powder mass recovered from the desired stages of the impactor by the total powder mass recovered in the impactor.

Similarly, for FPF measurements utilizing the NGI, the NGI instrument was run in controlled environmental conditions of 18 to 25° C. and relative humidity (RH) between 25 and 35%. The instrument consists of seven stages that separate aerosol particles based on inertial impaction and can be operated at a variety of air flow rates. At each stage, the aerosol stream passes through a set of nozzles and impinges on a corresponding impaction surface. Particles having small enough inertia will continue with the aerosol stream to the next stage, while the remaining particles will impact upon the surface. At each successive stage, the aerosol passes through nozzles at a higher velocity and aerodynamically smaller particles are collected on the plate. After the aerosol passes through the final stage, a micro-orifice collector collects the smallest particles that remain. Chemical analyses can then be performed to determine the particle size distribution. The capsules (HPMC, Size 3; Capsugel Vcaps, Peapack, N.J.) were hand filled with powder to a specific weight and placed in a hand-held, breath-activated dry powder inhaler (DPI) device, the high resistance RS01 DPI (Plastiape, Osnago, Italy). The capsule was punctured and the powder was drawn through the cascade impactor operated at a specified flow rate for 2.0 Liters of inhaled air. At the specified flow rate, the cut-off diameters for the stages were calculated. The fractions were collected by placing wetted filters in the apparatus and determining the amount of powder that impinged on them by chemical measurements on an HPLC. The fine particle fraction of the total dose of powder ($FPF_{TD}$) less than or equal to an effective cut-off aerodynamic diameter was calculated by dividing the powder mass recovered from the desired stages of the impactor by the total particle mass in the capsule. Results are reported for the NGI as the fine particle fraction of less than 5.0 microns ($FPF_{TD}<5.0$ microns)

Aerodynamic Diameter. Mass median aerodynamic diameter (MMAD) was determined using the information obtained by the Andersen Cascade Impactor (ACI). The cumulative mass under the stage cut-off diameter is calculated for each stage and normalized by the recovered dose of powder. The MMAD of the powder is then calculated by linear interpolation of the stage cut-off diameters that bracket the 50th percentile. An alternative method of measuring the MMAD is with the Next Generation Pharmaceutical Impactor (NGI). Like the ACI, the MMAD is calculated with the cumulative mass under the stage cut-off diameter is calculated for each stage and normalized by the recovered dose of powder. The MMAD of the powder is then calculated by linear interpolation of the stage cut-off diameters that bracket the 50th percentile.

Fine Particle Dose. The fine particle dose (FPD) is determined using the information obtained from the ACI. Alternatively, the FPD is determined using the information obtained from the NGI. The fine particle dose indicates the mass of one or more therapeutics in a specific size range and can be used to predict the mass which will reach a certain region in the respiratory tract. The fine particle dose can be measured gravimetrically or chemically. If measured gravimetrically, since the dry particles are assumed to be homogenous, the mass of the powder on each stage and collection filter can be multiplied by the fraction of therapeutic agent in the formulation to determine the mass of therapeutic. If measured chemically, the powder from each stage or filter is collected, separated, and assayed for example on an HPLC to determine the content of the therapeutic. The cumulative mass deposited on the final collection filter, and stages 6, 5, 4, 3, and 2 for a single dose of powder, contained in one or more capsules, actuated into the ACI is equal to the fine particle dose less than 4.4 microns (FPD<4.4 microns). The cumulative mass deposited on the final collection filter, and stages 6, 5 and 4 for a single dose of powder, contained in one or more capsules, actuated into the ACI is equal to the fine particle dose less than 2.0 microns (FPD<2.0 microns). The quotient of these two values is expressed as FPD<2.0 µm/FPD<4.4 µm. The higher the ratio, the higher the percentage of therapeutic that enters the lungs which is expected to penetrate to the alveolar regions of the lung. The lower the ratio, the lower the percentage of therapeutic that enters the lungs, which is expected to penetrate to the alveolar regions of the lung. For some therapies that target the central or conducting airways, a lower ratio such as less than 40%, less than 30%, or less than 20% is desired. For other therapies that target the deep lung, a higher ratio such as 40% or greater, 50% or greater, or 60% or greater is desired. Similarly, for FPD measurements utilizing the NGI, the NGI instrument was run as described in the Fine Particle Fraction description in the Exemplification section. The cumulative mass deposited on each of the stages at the specified flow rate is calculated and the cumulative mass corresponding to a 5.0 micrometer diameter particle is interpolated. This cumulative mass for a single dose of powder, contained in one or more capsules, actuated into the NGI is equal to the fine particle dose less than 5.0 microns (FPD<5.0 microns).

Emitted Geometric or Volume Diameter. The volume median diameter (Dv50) of the powder after it is emitted from a dry powder inhaler, which may also be referred to as volume median geometric diameter (VMGD), was determined using a laser diffraction technique via the Spraytec diffractometer (Malvern, Inc.). Powder was filled into size 3 capsules (V-Caps, Capsugel) and placed in a capsule based dry powder inhaler (RS01 Model 7 High resistance, Plastiape, Italy), or DPI, and the DPI sealed inside a cylinder. The cylinder was connected to a positive pressure air source with steady air flow through the system measured with a mass flow meter and its duration controlled with a timer controlled solenoid valve. The exit of the dry powder inhaler was exposed to room pressure and the resulting aerosol jet passed through the laser of the diffraction particle sizer (Spraytec) in its open bench configuration before being captured by a vacuum extractor. The steady air flow rate through the system was initiated using the solenoid valve. A steady air flow rate was drawn through the DPI typically at 60 L/min for a set duration, typically of 2 seconds. Alternatively, the air flow rate drawn through the DPI was sometimes run at 15 L/min, 20 L/min, or 30 L/min. The resulting geometric particle size distribution of the aerosol was calculated from the software based on the measured scatter pattern on the photodetectors with samples typically taken at 1000 Hz for the duration of the inhalation. The Dv50, GSD, FPF<5.0 µm measured were then averaged over the duration of the inhalation.

The Emitted Dose (ED) refers to the mass of therapeutic which exits a suitable inhaler device after a firing or dispersion event. The ED is determined using a method based on USP Section 601 Aerosols, Metered-Dose Inhalers and Dry Powder Inhalers, Delivered-Dose Uniformity, Sampling the Delivered Dose from Dry Powder Inhalers, United States Pharmacopeia convention, Rockville, Md., 13th Revision, 222-225, 2007. Contents of capsules are dispersed using the RS01 HR inhaler at a pressure drop of 4 kPa and a typical flow rate of 60 LPM and the emitted powder is collected on a filter in a filter holder sampling apparatus. The sampling apparatus is rinsed with a suitable solvent such as water and analyzed using an HPLC method. For gravimetric analysis a shorter length filter holder sampling apparatus is used to reduce deposition in the apparatus and the filter is weighed before and after to determine the mass of powder delivered from the DPI to the filter. The emitted dose of therapeutic is then calculated based on the content of therapeutic in the delivered powder. Emitted dose can be reported as the mass of therapeutic delivered from the DPI or as a percentage of the filled dose.

Capsule Emitted Powder Mass. A measure of the emission properties of the powders was determined by using the information obtained from the Andersen Cascade Impactor tests or emitted geometric diameter by Spraytec. The filled capsule weight was recorded at the beginning of the run and the final capsule weight was recorded after the completion of the run. The difference in weight represented the amount of powder emitted from the capsule (CEPM or capsule emitted powder mass). The CEPM was reported as a mass of powder or as a percent by dividing the amount of powder emitted from the capsule by the total initial particle mass in the capsule. While the standard CEPM was measured at 60 L/min, it was also measured at 15 L/min, 20 L/min, or 30 L/min.

Tap Density. Tap density was measured using a modified method requiring smaller powder quantities, following USP <616> with the substitution of a 1.5 cc microcentrifuge tube (Eppendorf AG, Hamburg, Germany) or a 0.3 cc section of a disposable serological polystyrene micropipette (Grenier Bio-One, Monroe, N.C.) with polyethylene caps (Kimble Chase, Vineland, N.J.) to cap both ends and hold the powder. Instruments for measuring tap density, known to those skilled in the art, include but are not limited to the Dual Platform Microprocessor Controlled Tap Density Tester (Vankel, Cary, N.C.) or a SOTAX Tap Density Tester model TD2 (Horsham, Pa.). Tap density is a standard, approximated measure of the envelope mass density. The envelope mass density of an isotropic particle is defined as the mass of the particle divided by the minimum spherical envelope volume within which it can be enclosed.

Bulk Density. Bulk density was estimated prior to tap density measurement procedure by dividing the weight of the powder by the volume of the powder, as estimated using the volumetric measuring device.

Thermogravimetric Analysis. Thermogravimetric analysis (TGA) was performed using a Thermogravimetric Analyzer Q500 (TA Instruments, New Castle, Del.). The samples were placed into an open aluminum DSC pan with the tare weight previously recorded by the instrument. The following method was employed: Ramp 10.00° C./min from ambient (~35° C.) to 200° C. The weight loss was reported as a function of temperature up to 150° C. TGA allows for the calculation of the water content of the dry powder.

Tiotropium Content using HPLC. Tiotropium content was measured using a high-performance liquid chromatography (HPLC) system with an ultraviolet (UV) detector. The HPLC method was performed using an HPLC system with UV detection (HPLC-UV; Waters, Milford, Mass.) with Waters Xterra MS C18 column (5 µm, 3×100 mm; Waters, Milford, Mass.) to identify and quantify tiotropium in a range of 0.03 µg/mL to 1.27 µg/mL. The HPLC-UV system was set up with 100 µL injection volume, 40° C. column temperature, 240 nm detection wavelength, and isocratic elution with a mobile phase of 0.1% trifluoroacetic acid (Fisher Scientific, Pittsburgh, Pa.) and acetonitrile (Fisher Scientific, Pittsburgh, Pa.) (85:15) to determine tiotropium content in a 10 minute run time. Results are reported as both tiotropium and tiotropium bromide content.

Liquid Feedstock Preparation for Spray Drying. Spray drying homogenous particles requires that the ingredients of interest be solubilized in solution or suspended in a uniform and stable suspension. Sodium chloride, leucine and tiotropium bromide are sufficiently water-soluble to prepare suitable spray drying solutions. Alternatively, ethanol or another organic solvent can be used Spray Drying Using Niro Spray Dryer. Dry powders were produced by spray drying utilizing a Niro Mobile Minor spray dryer (GEA Process Engineering Inc., Columbia, Md.) with powder collection from a cyclone, a product filter or both. Atomization of the liquid feed was performed using a co-current two-fluid nozzle either from Niro (GEA Process Engineering Inc., Columbia, Md.) or a Spraying Systems (Carol Stream, Ill.) two-fluid nozzle with gas cap 67147 and fluid cap 2850SS, although other two-fluid nozzle setups are also possible. In some embodiments, the two-fluid nozzle can be in an internal mixing setup or an external mixing setup. Additional atomization techniques include rotary atomization or a pressure nozzle. The liquid feed was fed using gear pumps (Cole-Parmer Instrument Company, Vernon Hills, Ill.) directly into the two-fluid nozzle or into a static mixer (Charles Ross & Son Company, Hauppauge, N.Y.) immediately before introduction into the two-fluid nozzle. An additional liquid feed technique includes feeding from a pressurized vessel. Nitrogen or air may be used as the drying gas, provided that moisture in the air is at least partially removed before its use. Pressurized nitrogen or air can be used as the atomization gas feed to the two-fluid nozzle. The process gas inlet temperature can range from 70° C. to 300° C. and outlet temperature from 30° C. to 120° C. with a liquid feedstock rate of 10 mL/min to 100 mL/min. The gas supplying the two-fluid atomizer can vary depending on nozzle selection and for the Niro co-current two-fluid nozzle can range from 5 kg/hr to 50 kg/hr or for the Spraying Systems two-fluid nozzle with gas cap 67147 and fluid cap 2850SS can range from 30 g/min to 150 g/min. The atomization gas rate can be set to achieve a certain gas to liquid mass ratio, which directly affects the droplet size created. The pressure inside the drying drum can range from +3 "WC to −6 "WC. Spray dried powders can be collected in a container at the outlet of the cyclone, onto a cartridge or baghouse filter, or from both a cyclone and a cartridge or baghouse filter.

Process gas as used in these descriptions refers to the drying gas. The two-fluid Spraying Systems nozzles were a 1/4J series of nozzles.

Spray Drying Using Büchi Spray Dryer. Dry powders were prepared by spray drying on a Büchi B-290 Mini Spray Dryer (BÜCHI Labortechnik AG, Flawil, Switzerland) with powder collection from either a standard or High Performance cyclone. The system was run either with air or nitrogen as the drying and atomization gas in open-loop (single pass) mode. When run using air, the system used the Büchi B-296 dehumidifier to ensure stable temperature and humidity of the air used to spray dry. Furthermore, when the relative humidity in the room exceeded 30% RH, an external LG dehumidifier (model 49007903, LG Electronics, Englewood Cliffs, N.J.) was run constantly. When run using nitrogen, a pressurized source of nitrogen was used. Furthermore, the aspirator of the system was adjusted to maintain the system pressure at −2.0" water column. Atomization of the liquid feed utilized a Büchi two-fluid nozzle with a 1.5 mm diameter or a Schlick 970-0 atomizer with a 0.5 mm liquid insert (Düsen-Schlick GmbH, Coburg, Germany). Inlet temperature of the process gas can range from 100° C. to 220° C. and outlet temperature from 30° C. to 120° C. with a liquid feedstock flowrate of 3 mL/min to 10 mL/min. The two-fluid atomizing gas ranges from 25 mm to 45 mm (300 LPH to 530 LPH) for the Büchi two-fluid nozzle and for the Schlick atomizer an atomizing air pressure of upwards of 0.3 bar. The aspirator rate ranges from 50% to 100%.

Spray Drying Using ProCepT Formatrix. Dry powders were prepared by spray drying on a ProCepT Formatrix R&D spray dryer (ProCepT nv, Zelzate, Belgium). The system was run in open loop configuration using room air in a manufacturing suite controlled to <60% RH. The drying gas flow rate can range from 0.2 to 0.5 m³/min. The bi-fluid nozzle was equipped for atomization with liquid tips from 0.15-1.2 mm. The atomization gas pressure could vary from about 0.5 bar to 6 bar. The system was equipped with either the small or medium cyclone. The inlet temperature of the spray dryer can range from about 100° C. to 190° C., with an outlet temperature from about 40° C. to about 95° C. The liquid feedstock flowrate can range from about 0.1 to 15 mL/min. Process parameters were controlled via the ProCepT human-machine interface (HMI) and all parameters were recorded electronically.

Clinical Measurements. Clinical measurements reported below include the maximal concentration for tiotropium in the bloodstream ($C_{max}$), the area under the curve for tiotropium in the bloodstream (AUC), and forced expiratory volume in one second of a patient ($FEV_1$). $C_{max}$ is the maximum concentration of a therapeutic agent, such as tiotropium, in the bloodstream. It provides pharmacokinetic (PK) information. It is measured as picograms per milliliter (pg/mL). AUC indicates the total systemic exposure of an individual to a therapeutic agent, such as tiotropium, over the stated timeframe. Herein, AUC was measured over the following timeframes, 0-2 hours, 0-6 hours, and 0-24 hours. AUC is measure in picogram-hours per milliliter (pg*hr/mL). $FEV_1$ is the forced expiratory volume in one second of a person, and can be used to determine the effect of administration of a therapeutic, such as tiotropium, to a patient. It provides pharmacodynamic (PD) information. $FEV_1$ is measured in liters (L).

Example 1. Tiotropium and Salt-containing Dry Powder Formulations

A. Powder Preparation.

Feedstock solutions were prepared and used to manufacture dry powders comprised of neat, dry particles containing tiotropium bromide, sodium chloride, and leucine. Powders were prepared in triplicate. Table 2 lists the components of the feedstock formulations used in preparation of the dry powders comprised of dry particles. Weight percentages are given on a dry basis.

TABLE 2

Feedstock compositions

| Formulation | Feedstock Composition (w/w), dry basis |
|---|---|
| I | 0.04% tiotropium bromide (TioB), 79.97% sodium chloride, 19.99% leucine |
| V | 0.22% tiotropium bromide (TioB), 79.82% sodium chloride, 19.96% leucine |

The feedstock solutions that were used to spray dry particles were made as follows. For Formulation I, the liquid feedstock was batch mixed, the total solids concentration was 30 g/L, the amount of tiotropium bromide in solution was 0.012 g/L, the amount of sodium chloride in the solution was 23.990 g/L, the amount of leucine in the solution was 5.998 g/L, and the final aqueous feedstock was clear. For Formulation V, the liquid feedstock was batch mixed, the total solids concentration was 30 g/L, the amount of tiotropium bromide in solution was 0.066 g/L, the amount of sodium chloride in the solution was 23.947 g/L, the amount of leucine in the solution was 5.989 g/L, and the final feedstock was clear. Feedstock volumes ranged from 0.720 to 1.800 L, which supported manufacturing campaigns from 2 to 5 hours.

Dry powders of Formulations I and V were manufactured from these feedstocks by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Schlick 970-0 atomizer with a 0.5 mm liquid insert. The aspirator of the system was adjusted to maintain the system pressure at −2.0" water column.

The following spray drying conditions were followed to manufacture the dry powders. For Formulations I and V, the liquid feedstock solids concentration was 30 g/L, the process gas inlet temperature was 178° C. to 182° C., the process gas outlet temperature was 77° C., the drying gas flowrate was 18.0 kg/hr, the atomization gas flowrate was 1.824 kg/hr, the atomization gas backpressure at the atomizer inlet was 34 psig to 37 psig and the liquid feedstock flowrate was 6.0 mL/min. The resulting dry powder formulations are reported in Table 3.

TABLE 3

Dry Powder compositions, dry basis

| Formulation | Dry Powder Composition (w/w), dry basis |
|---|---|
| I | 0.04% tiotropium bromide (TioB), 79.97% sodium chloride, 19.99% leucine |
| V | 0.22% tiotropium bromide (TioB), 79.82% sodium chloride, 19.96% leucine |

B. Powder Characterization.

The size and density characteristics are found in Table 4. The VMGD of Formulations I and V using the RODOS at a dispersion energy of 1 bar were both 2.30 micrometers, with a standard deviation of 0.04 and 0.03, respectively, indicating the process was reproducible over the triplicate spray drying productions. The span at 1 bar of 1.45 and 1.47 for Formulations I and V, respectively, indicates a relatively narrow size distribution. The 1 bar/4 bar dispersibility ratio of 1.21 and 1.22 for Formulations I and V, respectively, and the 0.5 bar/4 bar dispersibility ratio of 1.29 for both formulations indicate that they are relatively independent of dispersion energy, a desirable characteristic which allows the relatively similar therapeutic dose to be administered to a varying patient population.

The geometric particle size and capsule emitted powder mass (CEPM) measured and/or calculated at 60 liters per minute (LPM) and 20 LPM simulated patient flow rates were measured for the two formulations and reported in Table 4. Formulations I and V both had a CEPM of 100% at 60 LPM and 97% at 20 LPM. Formulation I had a Dv50 of 2.43 microns at 60 LPM and 2.63 microns at 20 LPM, and Formulation V had a Dv50 of 2.39 microns at 60 LPM and 2.62 microns at 20 LPM. The small change in CEPM and geometric size from 60 LPM to 20 LPM indicates that the dry powder formulations are relatively independent of patient inspiratory flowrate, indicating that patients breathing in at varying flow rates would receive a relatively similar therapeutic dose.

The aerodynamic particle size, fine particle fractions and fine particle doses measured and/or calculated with a two-stage and/or eight-stage Anderson Cascade Impactor (ACI-2 and ACI-8) are reported in Table 4. The fine particle fraction of the total dose less than 2.0, 3.4, 4.4, and 5.6 microns for Formulation I were 14%, 44%, 56.7%, and 72%, respectively, and for Formulation V were 14%, 45%, 58.8%, and 73%, respectively. It should be noted that the ACI-2 was run with just 1 capsule containing about 10 mg of dry powder while the ACI-8 was run with 2 capsules, totaling 20 mg of dry powder. The fine particle dose less than 4.4 micrometers (FPD<4.4) for Formulation I and V were 3.77 micrograms of tiotropium and 21.65 micrograms of tiotropium delivered from 2 capsules of 10 mg of powder each or 1.89 micrograms and 10.82 micrograms per capsule respectively.

The fine particle dose for Formulation I and V both indicate a high percentage of the nominal dose which is filled into the capsule reaches the impactor stages (57% and 59%) and so would be predicted to be delivered to the lungs. This reflects a significant improvement in efficiency of the inventive formulations over the commercially available lactose blend-based dry powder SPIRIVA (tiotropium bromide) HANDIHALER (dry powder inhaler) product. The SPIRIVA (tiotropium bromide) HANDIHALER (dry powder inhaler) product has a nominal dose of 18 micrograms of tiotropium filled into each capsule dose but delivers a fine particle dose (FPD<4.4) of between 2.5 and 3.7 micrograms for each filled capsule, as calculated from Shur et al., AAPS Journal, 2012 and Chodosh et al., Journal of Aerosol Medicine, 2001

The MMAD of Formulation I and V were 3.20 microns and 3.17 microns, respectively, indicating deposition in the central and conducting airways. The "FPD<2.0 micron/FPD<4.4 micron" ratios for Formulation I and V were 25% and 24%, respectively, indicating that 75% and 76%, respectively, of the FPD less than 4.4 microns has an FPD of 2.0 microns or greater, another indication that the majority of the dry powder should deposit in the central and conducting airways.

Properties relating to the bulk and tap densities of the formulations are reported in Table 4. The bulk density of both formulations was 0.26 g/cc and the tap density of Formulation I was 0.68 g/cc and of Formulation V was 0.69 g/cc. For Formulations I and V, the Hausner ratios were 2.58 and 2.70, respectively, and the Can Index was 61.22 and 62.57, respectively.

The water contents of Formulations I and V were measured with TGA and are reported in Table 4. They are 0.07% and 0.08%, respectively.

The tiotropium bromide contents of Formulations I and V were measured with HPLC-UV and are reported in Table 4. They are 0.040% and 0.221%, respectively.

TABLE 4

Formulations I and V Size and Density Characteristics

| Test Method | Parameter | Unit | Formulation I n = 3 Lots mean | ± | SD | Formulation V n = 3 Lots mean | ± | SD |
|---|---|---|---|---|---|---|---|---|
| Geometric Particle Size using a RODOS/HELOS | x50/dg @ 0.5 bar | (μm) | 2.30 | ± | 0.04 | 2.30 | ± | 0.03 |
| | GSD @ 0.5 bar | — | 1.66 | ± | 0.04 | 1.66 | ± | 0.02 |
| | Span @ 0.5 bar | — | 1.45 | ± | 0.03 | 1.47 | ± | 0.06 |

TABLE 4-continued

Formulations I and V Size and Density Characteristics

| Test Method | Parameter | Unit | Formulation I n = 3 Lots mean | ± | SD | Formulation V n = 3 Lots mean | ± | SD |
|---|---|---|---|---|---|---|---|---|
| | x50/dg @ 1 bar | (µm) | 2.17 | ± | 0.04 | 2.17 | ± | 0.03 |
| | GSD @ 1 bar | — | 1.66 | ± | 0.02 | 1.67 | ± | 0.03 |
| | Span @ 1 bar | — | 1.45 | ± | 0.03 | 1.48 | ± | 0.04 |
| | x50/dg @ 4 bar | (µm) | 1.79 | ± | 0.02 | 1.78 | ± | 0.01 |
| | GSD @ 4 bar | — | 1.76 | ± | 0.02 | 1.93 | ± | 0.16 |
| | Span @ 4 bar | — | 1.51 | ± | 0.04 | 1.58 | ± | 0.09 |
| | 1/4 bar | — | 1.21 | ± | 0.02 | 1.22 | ± | 0.02 |
| | 0.5/4 bar | — | 1.29 | ± | 0.02 | 1.29 | ± | 0.01 |
| Geometric Particle Size using a Spraytec | CEPM @ 60LPM | (%) | 100 | ± | 0 | 100 | ± | 0 |
| | Dv50 @ 60LPM | (µm) | 2.43 | ± | 0.07 | 2.39 | ± | 0.06 |
| | GSD @ 60 LPM | — | 1.89 | ± | 0.06 | 1.86 | ± | 0.05 |
| | Span @ 60 LPM | — | 1.99 | ± | 0.09 | 1.91 | ± | 0.11 |
| | CEPM @ 20LPM | (%) | 97 | ± | 1 | 97 | ± | 1 |
| | Dv50 @ 20LPM | (µm) | 2.63 | ± | 0.11 | 2.62 | ± | 0.06 |
| | GSD @ 20 LPM | — | 1.75 | ± | 0.04 | 1.76 | ± | 0.03 |
| | Span @ 20 LPM | — | 1.73 | ± | 0.10 | 1.78 | ± | 0.07 |
| Aerodynamic Particle Size using an ACI-2 | Powder weight | (mg) | 10.02 | ± | 0.08 | 10.03 | ± | 0.08 |
| | CEPM | (%) | 98 | ± | 0 | 98 | ± | 1 |
| | FPF_TD <3.4 µm | (%) | 44 | ± | 2 | 45 | ± | 4 |
| | FPF_TD <5.6 µm | (%) | 72 | ± | 2 | 73 | ± | 2 |
| | Mass collected | (%) | 77 | ± | 2 | 79 | ± | 1 |
| Aerodynamic Particle Size using an ACI-8 | Powder weight (two approx. 10 mg capsules) | (mg) | 20.04 | ± | 0.11 | 20.13 | ± | 0.13 |
| | −1 | (mg) | 0.20 | ± | 0.02 | 0.21 | ± | 0.02 |
| | 0 | (mg) | 0.77 | ± | 0.08 | 0.69 | ± | 0.10 |
| | 1 | (mg) | 2.71 | ± | 0.15 | 2.66 | ± | 0.28 |
| | 2 | (mg) | 3.41 | ± | 0.18 | 3.59 | ± | 0.16 |
| | 3 | (mg) | 5.15 | ± | 0.33 | 5.38 | ± | 0.20 |
| | 4 | (mg) | 1.54 | ± | 0.21 | 1.55 | ± | 0.17 |
| | 5 | (mg) | 0.40 | ± | 0.09 | 0.47 | ± | 0.08 |
| | 6 | (mg) | 0.32 | ± | 0.10 | 0.35 | ± | 0.04 |
| | F | (mg) | 0.53 | ± | 0.15 | 0.50 | ± | 0.15 |
| | MMAD | (µm) | 3.20 | ± | 0.10 | 3.17 | ± | 0.08 |
| | GSD | — | 1.75 | ± | 0.08 | 1.73 | ± | 0.03 |
| | FPD < 2.0 µm | (mg) | 2.79 | ± | 0.33 | 2.87 | ± | 0.18 |
| | FPF_TD < 2.0 µm | (%) | 14 | ± | 2 | 14 | ± | 1 |
| | FPD < 4.4 µm | (mg) | 11.35 | ± | 0.37 | 11.84 | ± | 0.23 |
| | FPD < 4.4 µm | (µg Tio) | 3.77 | ± | 0.12 | 21.65 | ± | 0.43 |
| | FPF_TD < 4.4 µm | (%) | 57 | ± | 2 | 59 | ± | 1 |
| | FPD < 2.0 µm/ FPD < 4.4 µm | — | 0.25 | ± | 0.02 | 0.24 | ± | 0.01 |
| Densities | Bulk density | (g/cc) | 0.26 | ± | 0.02 | 0.26 | ± | 0.02 |
| | Tapped density | (g/cc) | 0.68 | ± | 0.08 | 0.69 | ± | 0.06 |
| | Hausner ratio | — | 2.58 | ± | 0.12 | 2.70 | ± | 0.34 |
| | Carr Index | — | 61.22 | ± | 1.81 | 62.57 | ± | 4.99 |

TABLE 4-continued

Formulations I and V Size and Density Characteristics

| Test Method | Parameter | Unit | Formulation I n = 3 Lots | | | Formulation V n = 3 Lots | | |
|---|---|---|---|---|---|---|---|---|
| | | | mean | ± | SD | mean | ± | SD |
| TGA (Water content) | Water Content | (%) | 0.07 | ± | 0.02 | 0.08 | ± | 0.03 |
| Tiotropium Bromide Content using HPLC | Tiotropium Bromide Content | (%) | 0.040 | ± | 0 | 0.221 | ± | 0 |

Example 2. Formulation V Reduces Specific Airway Resistance Following Methylcholine Challenge in Healthy Mice In order to determine efficacy of tiotropium bromide present in Formulation V, pulmonary function testing was conducted in healthy mice one hour following treatment with Formulation V. Treatments were made in a whole body exposure chamber using a capsule based dry powder inhaler system. Dose was varied by changing the number of capsules used for each exposure, in this case 2 or 3, 90 mg capsules for an estimated expected dose of 4.4 µg or 6.6 µg tiotropium bromide, respectively. Pulmonary function testing was conducted by measuring the specific airway resistance (sRaw) in mice through dual chamber plethysmography. Baseline sRaw measurements were taken for 5 minutes, followed by 5 minutes of measurement after nebulization of 0 mg/ml and 100 mg/ml methylcholine chloride (MCh) dissolved in 0.9% sodium chloride into the head chamber.

The results are shown in Table 5. Treatment with both 4.4 µg and 6.6 µg tiotropium bromide resulted in a more that 40% reduction in sRaw in comparison with untreated mice, p=0.035 and p=0.032, respectively, following challenge with 100 mg/ml MCh. There were no significant changes in sRaw at baseline or following challenge with 0 mg/ml MCh. It is known from the literature, e.g., "Effect of tiotropium bromide on airway inflammation and remodeling in a mouse model of asthma", Clinical and Experimental Allergy 40:1266-1275), that tiotropium bromide results in enhanced pulmonary function during MCh challenge by antagonizing the M3 muscarinic receptor, the same receptor that recognizes MCh, ultimately leading to bronchoconstriction. Additionally, it has been demonstrated that tiotropium bromide enhanced pulmonary function, resulting in lower sRaw values, for animals and humans challenged with inhaled MCh in 0.9% sodium chloride. The results reported in Table 5, specifically unchanged sRaw values at baseline and 0 mg/ml in conjunction with a significant reduction of sRaw after 100 mg/ml MCh challenge. Formulation V reduced sRaw following MCh challenge in healthy mice.

TABLE 5

MCh challenge following Formulation V treatment in healthy mice.

| | sRaw (cmH$_2$O · s) | | |
|---|---|---|---|
| Challenge | Untreated | 4.4 micrograms tiotropium bromide | 6.6 micrograms tiotropium bromide |
| Baseline | 5.33 ± 1.20 | 4.68 ± 0.29 | 4.62 ± 0.49 |
| 0 mg/ml MCh | 5.43 ± 1.34 | 4.16 ± 0.55 | 5.60 ± 2.06 |
| 100 mg/ml MCh | 13.75 ± 3.13 | 8.23 ± 3.75* | 8.26 ± 3.55* |

Data are represented as Mean ± SD;
*p < 0.05

Example 3. Dry Powder Formulations Containing Tiotropium in Combination with Additional Pharmaceutically Active Agents A. Powder Preparation.

Feedstock solutions were prepared in order to manufacture dry powders comprised of dry particles containing a sodium salt, a non-salt excipient, tiotropium and optionally additional pharmaceutical active agents. Table 6 lists the components of the feedstock formulations used in preparation of the dry powders comprised of dry particles. Weight percentages are given on a dry basis.

TABLE 6

Feedstock compositions of sodium-salt with tiotropium and in combination with other pharmaceutically active agents.

| Formulation | Salt | % Salt load (w/w) | Excipient | % Excipient load (w/w) | Drug | % Drug load (w/w) |
|---|---|---|---|---|---|---|
| VI | Sodium Chloride | 65.42 | Leucine | 34.47 | Tiotropium Bromide (TioB) | 0.113 |
| VII | Sodium Chloride | 85.31 | Leucine | 10.0 | FP/SX/TioB | 4.0/0.58/ 0.113 |
| VIII | Sodium Chloride | 65.42 | Leucine | 29.89 | FP/SX/TioB | 4.0/0.58/ 0.113 |

The feedstock solutions were made according to the parameters in Tables 7 and 8.

TABLE 7

Formulation Conditions

| Formulation: | VI | VII |
|---|---|---|
| Total solids (g) | 3 | 10 |
| Total volume water (L) | 0.3 | 0.4 |
| Total solids concentration (g/L) | 10 | 10 |
| Amount of NaCl in 1 L (g) | 6.542 | 8.531 |
| Amount leucine in 1 L (g) | 3.447 | 1.0 |
| Amount FP in 1 L (g) | 0 | 0.4 |
| Amount SX in 1 L (g) | 0 | 0.058 |
| Amount TioB in 1 L (g) | 0.0113 | 0.0113 |

TABLE 8

Formulation Conditions

| Formulation: | VIII |
|---|---|
| Total solids (g) | 4 |
| Total volume water (L) | 0.4 |
| Total solids concentration (g/L) | 10 |
| Amount of NaCl in 1 L (g) | 6.542 |
| Amount of NaSulf in 1 L (g) | 0 |
| Amount of NaCit in 1 L (g) | 0 |
| Amount leucine in 1 L (g) | 2.989 |
| Amount mannitol in 1 L (g) | 0 |
| Amount FP in 1 L (g) | 0.4 |
| Amount SX in 1 L (g) | 0.058 |
| Amount TioB in 1 L (g) | 0.0113 |
| Amount Insulin in 1 L (g) | 0 |
| Amount IgG in 1 L (g) | 0 |

For all formulations, the liquid feedstock was batch mixed Formulation VI through VIII dry powders were produced by spray drying on the Büchi B-290 Mini Spray Dryer (BÜCHI Labortechnik AG, Flawil, Switzerland) with powder collection from a High Performance cyclone in a 60 mL glass vessel. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm (667 LPH). The aspirator rate was set to 80% (32 m³/h) for Formulation VI; 70% for Formulations VII, and VIII. Air was used as the drying gas and the atomization gas. Table 9 below includes details about the spray drying conditions.

TABLE 9

Spray Drying Process Conditions

| | Formulation | | |
|---|---|---|---|
| Process Parameters | VI | VII | VIII |
| Liquid feedstock solids concentration (g/L) | 10 | 10 | 10 |
| Process gas inlet temperature (° C.) | 115 | 180 | 180 |
| Process gas outlet temperature (° C.) | 67-68 | 74-75 | 71-74 |
| Process gas flowrate (liter/hr, LPH) | 667 | 667 | 667 |
| Atomization gas flowrate (meters³/hr) | 32 | 29 | 29 |
| Liquid feedstock flowrate (mL/min) | 2.5 | 10 | 12.1 |

B. Powder Characterization.

Powder physical and aerosol properties are summarized in Tables 10 to 14 below. Values with ±indicate standard deviation of the value reported. Two-stage ACI-2 results are reported in Table 10 for $FPF_{TD}$<3.4 μm and $FPF_{TD}$<5.6 μm. Formulations VI through VIII had a $FPF_{TD}$<3.4 μm greater than 20% and a $FPF_{TD}$<3.4 μm greater than 30%. Formulation VI had a $FPF_{TD}$<3.4 μm greater than 45%. Formulations VI through VIII had a $FPF_{TD}$<5.6 μm greater than 40% and a $FPF_{TD}$<5.6 μm of greater than 60%.

TABLE 10

Aerodynamic properties

| | ACI-2 | | | | | |
|---|---|---|---|---|---|---|
| | $FPF_{TD}$ < 3.4 μm | | | $FPF_{TD}$ < 5.6 μm | | |
| Formulation | % | | | % | | |
| VI | 53.96% | ± | 1.44% | 73.00% | ± | 1.80% |
| VII | 40.29% | ± | 0.28% | 65.33% | ± | 0.41% |
| VIII | 37.80% | ± | 2.97% | 62.74% | ± | 2.47% |

Formulations VI through VIII had a tapped density greater than 0.35 g/cc, and Formulations VI and VII had a tapped density greater than 0.40 g/cc. Formulations VI and VII had a tapped density greater than 0.50 g/cc. Formulations VI through VIII had a Hausner Ratio greater than or equal to 1.5. Formulations VII and VIII had a Hausner Ratios greater than 2.0. Formulation VII had a Hausner Ratio of 3.07 (see Table 11).

TABLE 11

Density properties

| | Density | | | | | | |
|---|---|---|---|---|---|---|---|
| | Bulk | | | Tapped | | | Hausner |
| Formulation | g/cc | | | g/cc | | | Ratio |
| VI | 0.34 | ± | 0.01 | 0.52 | ± | 0.05 | 1.54 |
| VII | 0.17 | ± | 0 | 0.52 | ± | 0.04 | 3.07 |
| VIII | 0.18 | ± | 0.01 | 0.37 | ± | 0.06 | 2.09 |

Table 12 shows that Formulations VI through VIII had Dv50 of less than 2.0 microns at 60 LPM. Formulations VI through VIII had a Dv50 of less than 6.0 μm at 15 LPM. Formulations VII had a Dv50 of less than 5.0 μm at 15 LPM.

TABLE 12

Geometric Diameters

| | Dispersibility - Spraytec | | | |
|---|---|---|---|---|
| | @ 60 LPM | | @ 15 LPM | |
| Formulation | Dv50 (μm) | GSD | Dv50 (μm) | GSD |
| VI | 1.28 ± 0.08 | 5.59 ± 0.18 | 5.85 ± 0.18 | 4.04 ± 0.10 |
| VII | 1.55 ± 0.07 | 5.02 ± 0.34 | 4.23 ± 0.10 | 3.20 ± 0.25 |
| VIII | 1.70 ± 0.07 | 4.47 ± 0.25 | 5.09 ± 0.20 | 3.27 ± 0.11 |

Table 13 shows that Formulations VI through VIII had a capsule emitted particle mass (CEPM) of greater than 96% at 60 LPM. Formulations VI through VIII had a CEPM of greater than 90% at 15 LPM.

TABLE 13

Dispersibility properties

| Formulation | Dispersibility - CEPM | | | | | |
|---|---|---|---|---|---|---|
| | @ 60 LPM CEPM | | | @ 15 LPM CEPM | | |
| VI | 99.33% | ± | 0.40% | 96.92% | ± | 0.81% |
| VII | 97.46% | ± | 0.14% | 95.94% | ± | 0.55% |
| VIII | 99.47% | ± | 0.14% | 97.92% | ± | 0.41% |

Table 14 shows that Formulations VI through VIII had a Dv50 of less than 2.0 µm when using the RODOS at a 1.0 bar setting. Formulations VI through VIII had a RODOS Ratio for 0.5 bar/4 bar of less than 1.4, and Formulations VI and VIII had a RODOS Ratio for 0.5 bar/4 bar of less than 1.3. Formulations VI through VIII had a RODOS Ratio for 1 bar/4 bar of less than or equal to about 1.1.

TABLE 14

Dispersibility properties (Geometric diameter using RODOS)

| | RODOS | | | | | | | |
|---|---|---|---|---|---|---|---|---|
| | 0.5 bar | | 1.0 bar | | 4.0 bar | | | |
| Form. | Dv50 (µm) | GSD | Dv50 (µm) | GSD | Dv50 (µm) | GSD | 0.5/4 bar | 1/4 bar |
| VI | 1.66 | 2.16 | 1.46 | 2.06 | 1.36 | 1.92 | 1.22 | 1.07 |
| VII | 1.87 | 1.95 | 1.48 | 1.78 | 1.37 | 1.78 | 1.36 | 1.08 |
| VIII | 1.95 | 1.96 | 1.74 | 1.93 | 1.6 | 1.91 | 1.22 | 1.09 |

Example 4. Effect of a Monovalent Cation-Based Dry Powder of Tiotropium Bromide (Formulation VI) on Airway Hyperreactivity in an Ovalbumin Mouse Model of Allergic Asthma An ovalbumin mouse model of allergic asthma, protocols for sensitization and subsequent challenging with OVA, and pulmonary function testing are described in Examples 6 to 8 of PCT Publication No. WO 2012/044736 "Monovalent Cation Dry Powders" and are incorporated by reference herein in their entirety.

It was known from the literature that tiotropium bromide (TioB) enhances pulmonary function, resulting in lower sRaw values, for animals and human beings challenged with methacholine chloride (MCh) in 0.9% sodium chloride for inhalation. (Ohta, S. et al. (2010), "Effect of tiotropium bromide on airway inflammation and remodeling in a mouse model of asthma", Clinical and Experimental Allergy 40:1266-1275).

While the effects of TioB on sRaw were known from the literature, the effect of co-formulating the TioB formulation with a sodium salt was unknown. Formulation VI (34.47% leucine, 65.42% NaCl and 0.113% tiotropium bromide, w/w on a dry basis) was tested, and compared to Placebo-B dry powder (98% leucine, 2% NaCl, w/w on a dry basis). Results from pulmonary function testing are shown in Table 15.

TABLE 15

Effect on specific airway resistance of Formulation VI.

| Condition | Placebo-B Specific Airway Resistance [cm H$_2$O × s] (Standard Deviation) | Formulation VI |
|---|---|---|
| Baseline | 2.6 (1.5) | 4.7 (1.0) |
| PBS | 2.9 (1.5) | 5.2 (0.8) |
| 50 mg/ml MCh | 21.0 (12.0) | 5.4 (1.0) |
| 100 mg/ml MCh | 18.0 (12.8) | 6.3 (2.0) |

These data show that Formulation VI significantly reduced sRaw during MCh challenge compared to Placebo-B (p<0.00001).

Example 5. Pharmacokinetic (PK) and Pharmacodynamics (PD) Effects of Monovalent Cation-Based Dry Powders of Tiotropium Bromide (Formulations I-IV)

Figure 1B:
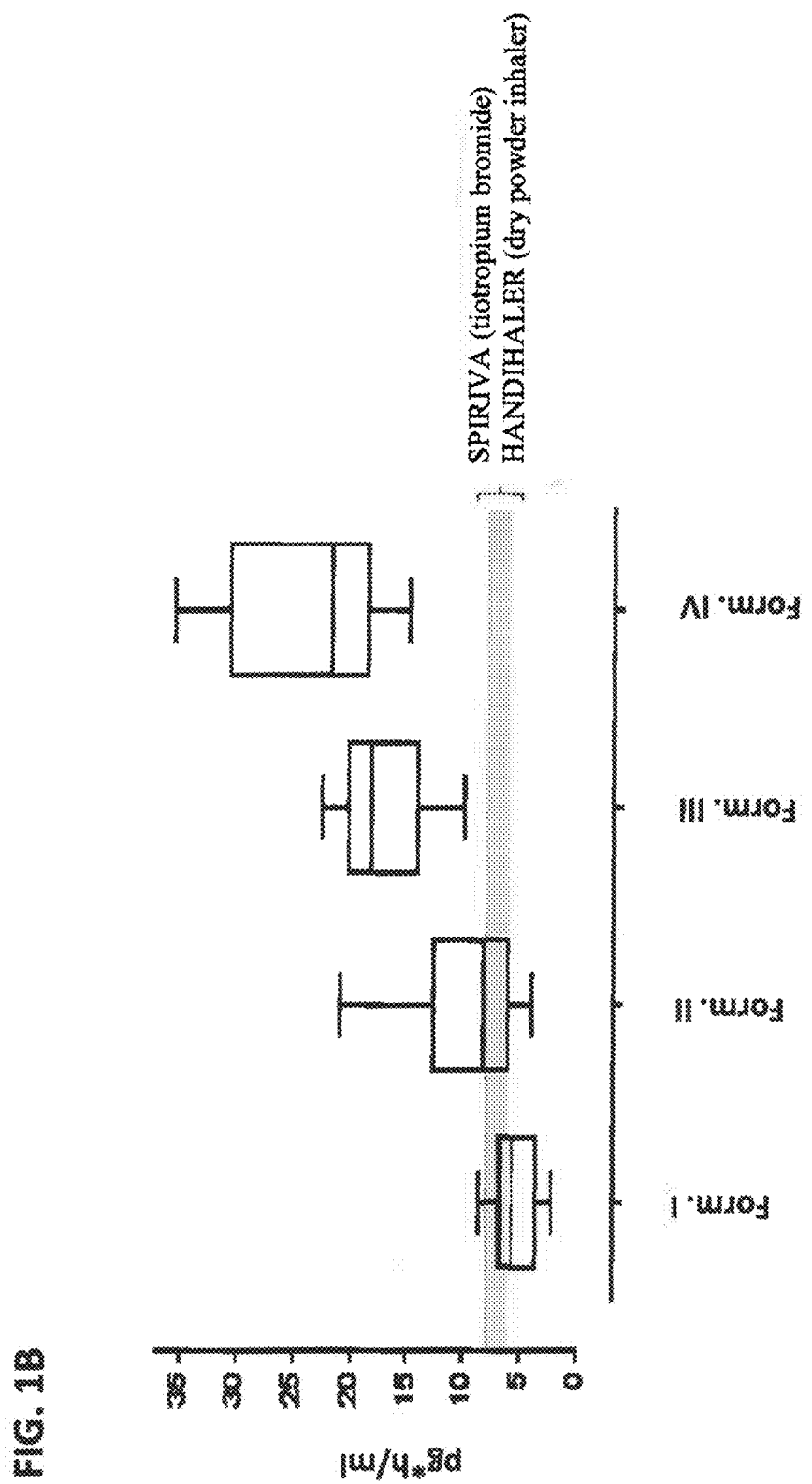
FIG. 1B is a plot depicting the area under the curve (AUC) for hours 0-2 after administration of Formulations I, II, III, and IV, respectively, as ($pg_{tiotropium}$ per hour)/$ml_{serum}$.
Figure 2:
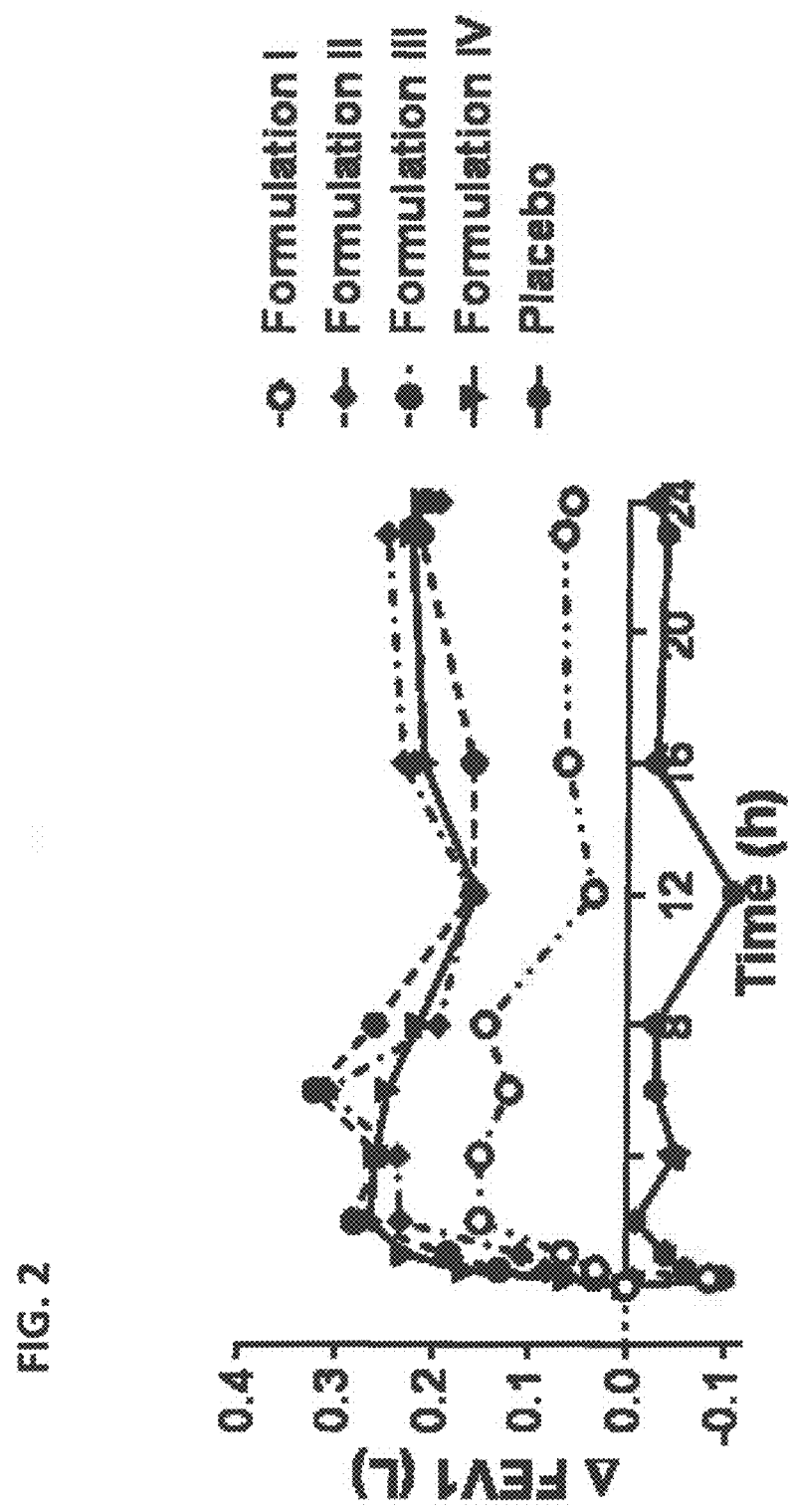
FIG. 2 is a graph depicting mean change in $FEV_1$ (forced expiratory volume in one second) from baseline over time for exemplary Formulations I, II, III, IV, and placebo, respectively.

In a pilot study, four doses (two per cohort) of a monovalent cation-based dry powder of tiotropium bromide, Formulations I-IV, were evaluated. Plasma levels of tiotropium bromide were measured over time (FIG. 1) and the bronchodilatory effect was measured (FIG. 2). Subjects were moderate to severe COPD patients. Single-doses of Formulations I-IV and matching placebo were administered in a double-blind inter-leaving cross-over design. The study was designed to enroll a total of 24 COPD subjects randomised to 2 cohorts of 12 each taking part in a 2 way dosing regimen. Within each cohort up to 10 subjects were to receive the active agent (Formulations I-IV comprising tiotropium bromide) and 2 were to receive placebo. Formulation I provides a nominal dose of 3 µg, Formulation II provides a nominal dose of 6 µg, Formulation III provides a nominal dose of 9 µg, and Formulation IV provides a nominal dose of 12 µg, as indicated in Table 16.

Data used in this example, including the tables and figures, represent unaudited data from a clinical trial. Formulations used in this example were manufactured with a ProCepT Formatrix R&D spray dryer.

TABLE 16

Formulations I-IV and Placebo.

| Formulation | Composition (wt %) | | | Nominal Dose in 10 mg |
|---|---|---|---|---|
| | Tiotropium Bromide | Leucine | Sodium Chloride | Fill Weight (µg tiotropium) |
| I | 0.04 | 19.99 | 79.97 | 3 |
| II | 0.07 | 19.99 | 79.94 | 6 |
| III | 0.11 | 19.98 | 79.91 | 9 |
| IV | 0.14 | 19.97 | 79.89 | 12 |
| Placebo | 0.00 | 20.00 | 80.00 | 0 |

Cohort 1 received Formulation I or placebo during the first treatment period (12 subjects: 2 placebo, 10 Formulation I), followed by a wash out period of a minimum of seven days. After a safety review, Cohort 2 received Formulation II or placebo during the first treatment period (12 subjects: 2 placebo, 10 Formulation II), followed by a wash out period of a minimum of seven days. After a safety review and the washout period, Cohort 1 returned to receive Formulation III or placebo for the second treatment period (11 subjects: 2 placebo, 9 Formulation III). After a final safety review and a washout period, Cohort 2 returned to receive Formulation IV or placebo for the second treatment period (10 subjects: 2 placebo, 8 Formulation IV).

Serum levels of tiotropium bromide were determined using LC-MS/MS (Liquid chromatography-tandem mass spectrometry) methods well known in the art, e.g. as described in Nilsson et al. PLoS One, 5(7):e11411 (2010). The following analytes were detected:

TABLE 17

Tiotropium analytes.

| Analyte | Precursor ion (m/z) | Product ion (m/z) |
|---|---|---|
| Tiotropium | 392.1 | 152.1 |
| Tiotropium-D3 | 395.2 | 155.2 |

Pulmonary function tests were performed using a standard calibrated spirometer. As a measure of the bronchodilatory effects of Formulations I-IV in human subjects, $FEV_1$ (forced expiratory volume in one second) was used. The predicted $FEV_1$ was obtained using the normal prediction equations by the ERS (European Respiratory Society) adjusting for race, gender and age. Quanjer et al. "Lung volume and forced ventilatory flows." Eur Respir J. 6: Suppl. 16, 5-40 (1993). Spirometry measurements were conducted in accordance with ATS/ERS (American Thoracic Society/European Respiratory Society) 2005 guidelines. The single highest $FEV_1$ and the single highest FVC (forced vital capacity) values from acceptable and repeatable maneuvers were reported and the $FEV_1$/FVC ratio determined.

Unaudited data obtained from the pilot study suggest that tiotropium bromide, exemplified by Formulations I-IV, was effectively delivered to the lungs in monovalent cation-based dry powders, and tiotropium bromide could be measured in the blood. FIG. 1A depicts the geometric mean PK profile of each nominal dose level (Formulations I-IV, 3 µg, 6 µg, 9 µg, and 12 µg, respectively) over a period of 6 hours. The maximal concentration for tiotropium ($C_{max}$) was detected at about 5 minutes after administration. This profile is consistent with the PK profile of SPIRIVA (tiotropium bromide) HANDIHALER (dry powder inhaler). FIG. 1B depicts the mean area under the curve ($AUC_{0-2h}$) for each Formulation, I-IV. For comparison, the known profile of single doses of SPIRIVA (tiotropium bromide) HANDIHALER (dry powder inhaler) is indicated by a grey boxed area. The data for SPIRIVA (tiotropium bromide) HANDIHALER (dry powder inhaler) may be obtained from the FDA's website: www.accessdata.fda.gov/scripts/cder/drugsatfda/. The $AUC_{0-2h}$ for Formulations I-IV bracket the profile of SPIRIVA (tiotropium bromide) HANDIHALER (dry powder inhaler).

FIG. 2 depicts pharmacodynamic data that suggest that Formulations I-IV all improved pulmonary function, each exerting a measurable bronchodilatory effect as measured by increased peak $FEV_1$ over the first 6 h after dosing and increased trough $FEV_1$ 24 h after dosing. Formulation I (a nominal dose of 3 µg tiotropium) resulted in a measurable and sustained increase in $FEV_1$. Formulations II-IV (nominal doses of 6, 9, and 12 µg tiotropium, respectively) resulted in larger improvements in $FEV_1$ compared to Formulation I. The profiles obtained for Formulations II-IV were fairly similar. The single dose improvement in lung function of Formulations I-IV are comparable to single dose SPIRIVA (tiotropium bromide) HANDIHALER (dry powder inhaler) lung function improvement, as described, e.g. by Maesen et al., "Tiotropium bromide, a new long-acting antimuscarinic bronchodilator: a pharmacodynamics study in patients with chronic obstructive pulmonary disease (COPD)" Eur. Respir. J, 8:1506-13 (1995). However, the improvements can be obtained at significantly lower nominal doses when compared to the SPIRIVA (tiotropium bromide) HANDIHALER (dry powder inhaler) product.

Example 6. An In Vitro Testing Comparing the Aerodynamic Particle Sizes of Tiotropium Bromide Formulation II to the SPIRIVA (Tiotropium Bromide) HANDIHALER (Dry Powder Inhaler)

In vitro mass median aerodynamic diameter (MMAD) testing, also referred to as aerodynamic particle size distribution (aPSD) testing, was performed which compared Formulation II to the SPIRIVA (tiotropium bromide) HANDIHALER (dry powder inhaler). The goals of this study were i) to inform the development of a formulation that achieved similar fine particle dose delivery across a range of flow rates relevant for COPD patients and ii) to determine if Formulation II, representative of all the Formulations I-IV, was less dependent on a patient's inspiratory flow rate than the SPIRIVA (tiotropium bromide) HANDIHALER (dry powder inhaler). This MMAD testing was performed across a range of flow rates relevant to the intended COPD patient population.

Figure 3:
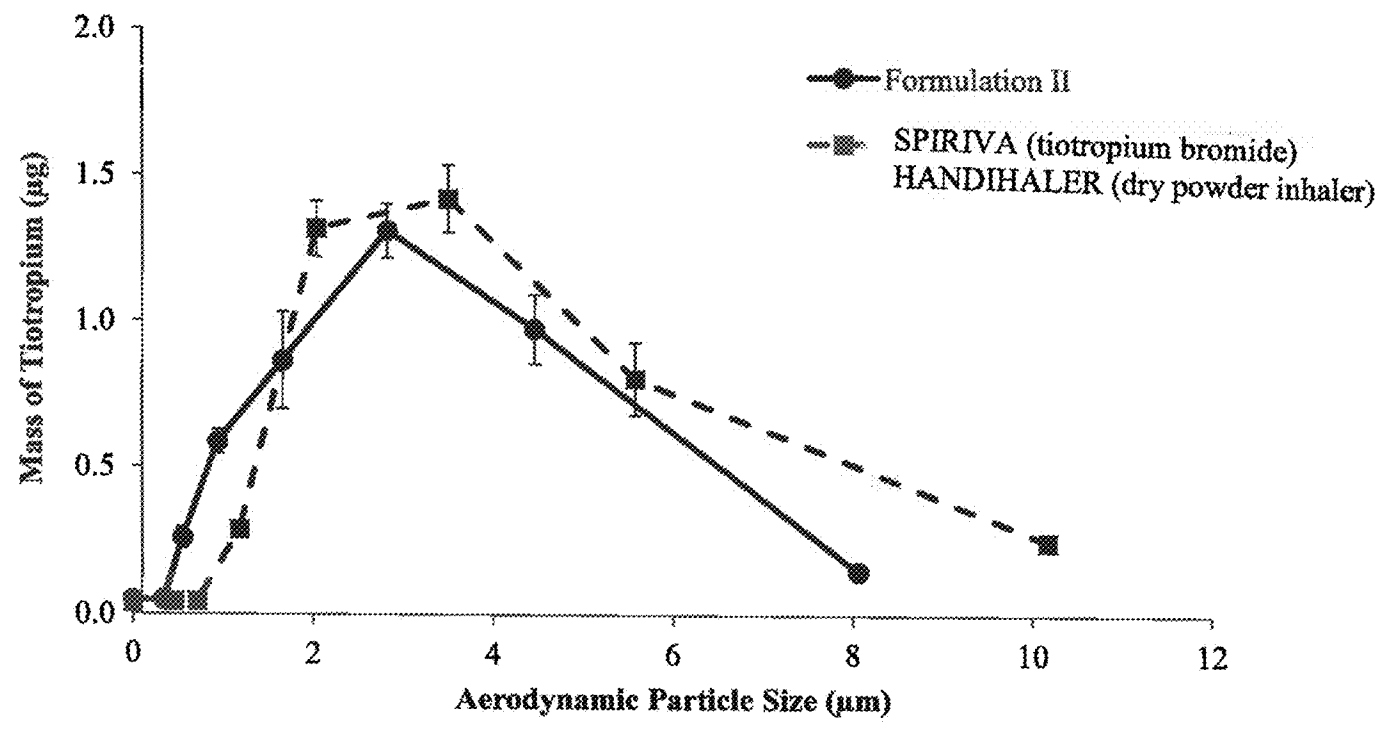

Formulation II was produced and filled into size 3 HPMC capsules for dispersion in the RS01 dry powder inhaler. SPIRIVA (tiotropium bromide) was procured and dispersed from the HANDIHALER (dry powder inhaler). A multistage next-generation impactor (NGI) was used to determine the mass distributed at various aerodynamic diameters, the fine particle fraction (FPF) less than 5 micrometers in diameter, and the fine particle dose (FPD) less than 5 micrometers in diameter. Due to the differing airflow resistance of the two dry powder inhalers, the formulations were compared at similar pressure drops across the inhaler rather than at the same air flow rate. The distributions are shown at a 4 kPa pressure drop across each dry powder inhaler. (See FIG. 3 and Table 18 below) For Formulation II using the RS01 HR device, this pressure drop correlated to an inspiratory flow rate of 60 LPM. For SPIRIVA (tiotropium bromide) HANDIHALER (dry powder inhaler), this pressure drop correlated to an inspiratory flow rate of 39 LPM. Testing was performed with replicates, n=5 for the Formulation II using the RS01 HR inhaler and n=3 for SPIRIVA (tiotropium bromide) HANDIHALER (dry powder inhaler). Similar aerodynamic particle size distributions are seen for the 2 products and the fine particle dose (FPD<5.0 µm) was found to be comparable for Formulation II using the RS01 inhaler and the SPIRIVA (tiotropium bromide) HANDIHALER (dry powder inhaler), even though the nominal dose of Formulation II was 5.8 micrograms and the nominal dose of SPIRIVA (tiotropium bromide) HANDIHALER (dry powder inhaler) was 18 micrograms. This means that the delivery efficiency for Formulation II using the RS01 inhaler was over three times more efficient that the SPIRIVA (tiotropium bromide) HANDIHALER (dry powder inhaler). This result is further illustrated by the difference in the fine particle fraction (FPF<5.0 μm) relative to the nominal dose, which was 54.8% for Formulation II in the RS01 HR, and 15.0% for SPIRIVA (tiotropium bromide) HANDIHALER (dry powder inhaler). (See Table 19 below.) The loss of drug product for the SPIRIVA (tiotropium bromide) HANDIHALER (dry powder inhaler) was attributed to the relatively higher amounts of the therapeutic left in the capsule, device, mouthpiece adapter, induction port and pre-separator. (See FIG. 4 and Table 20 below.) A pre-separator was not included in NGI testing with Formulation II with the RS01 inhaler because carrier particles were not present in the spray-dried formulation.

TABLE 18

Tiotropium mass distribution by stage of the NGI at 4 kPa for both Formulation II using the RS01 inhaler per 5.8 μg tiotropium nominal dose and the SPIRIVA (tiotropium bromide) HANDIHALER (dry powder inhaler) per 18 microgram (μg) nominal dose.

| Tiotropium mass distribution by stage of the NGI | Formulation II using the RS01 inhaler at 60 LPM and 5.8 μg nominal dose (μg tiotropium) | SPIRIVA (tiotropium bromide) HANDIHALER (dry powder inhaler) at 39 LPM and 18 μg nominal dose (μg tiotropium) |
|---|---|---|
| Stage 1 | 0.15 ± 0.03 | 0.25 ± 0.01 |
| Stage 2 | 0.97 ± 0.12 | 0.81 ± 0.13 |
| Stage 3 | 1.31 ± 0.09 | 1.42 ± 0.11 |
| Stage 4 | 0.87 ± 0.16 | 1.32 ± 0.10 |
| Stage 5 | 0.59 ± 0.04 | 0.29 ± 0.02 |
| Stage 6 | 0.26 ± 0.04 | 0.04 ± 0.01 |
| Stage 7 | 0.05 | 0.04 |
| Micro-Orifice Collector | 0.05 | 0.04 |
| After Filter | 0.00 | 0.02 |

TABLE 19

Tiotropium nominal dose and FPF less than 5.0 microns as a percentage of the nominal dose using the RS01 inhaler and the SPIRIVA (tiotropium bromide) HANDIHALER (dry powder inhaler).

|  | Formulation II using the RS01 inhaler | SPIRIVA (tiotropium bromide) HANDIHALER (dry powder inhaler) |
|---|---|---|
| Nominal Dose (μg tiotropium) | 5.8 | 18 |
| FPF (<5.0 microns) as a percentage of the Nominal Dose | 54.8 ± 2.8 | 15.0 ± 1.2 |

TABLE 20

Tiotropium mass distribution on various components before entering the NGI at 4 kPa for both Formulation II using the RS01 inhaler and the SPIRIVA (tiotropium bromide) HANDIHALER (dry powder inhaler).

| Powder distribution on various components before entering the NGI | Formulation II using the RS01 inhaler at 60 LPM and 5.8 μg nominal dose (μg tiotropium) | SPIRIVA (tiotropium bromide) HANDIHALER (dry powder inhaler) at 39 LPM and 18 μg nominal dose (μg tiotropium) |
|---|---|---|
| Capsule | 0.09 ± 0.00 | 6.42 ± 0.53 |
| Dry Powder Inhaler | 0.23 ± 0.01 | 1.68 |
| Mouthpiece Adapter, Induction Port and Pre-separator | 0.63 ± 0.04 | 5.23 0.27 |

Aerosol testing was performed over a range of peak inspiratory flows (PIF) relevant to the intended COPD patient population. A flow rate range 20 L/min to 55 L/min, with a mid-point of 39 L/min was selected for testing SPIRIVA (tiotropium bromide) HANDIHALER (dry powder inhaler), which spans the PIF range that was measured for COPD patients with the product and is specified in the United States product package insert for SPIRIVA (tiotropium bromide) HANDIHALER (dry powder inhaler). For Formulation II, the corresponding flow rate range was calculated from the SPIRIVA (tiotropium bromide) HANDIHALER (dry powder inhaler) range by matching differential pressure based on the different resistances of the DPIs, resulting in a PIF range of 28 L/min to 84 L/min with a mid-point of 60 LPM. The DPI used for Formulation II was the RS01 HR inhaler, while the DPI used for the SPIRIVA (tiotropium bromide) product was the HANDIHALER (dry powder inhaler).

Figure 5:
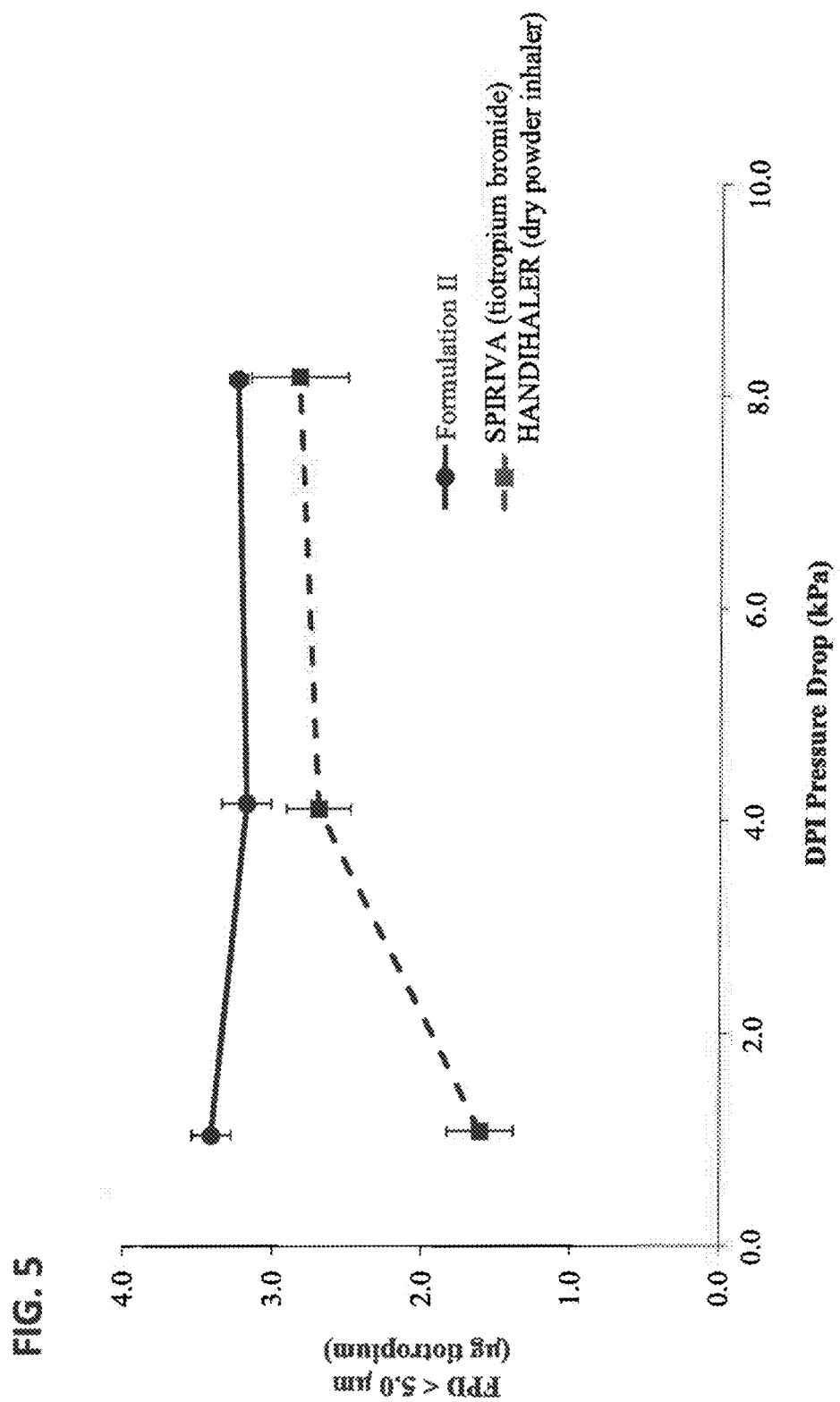
FIG. 5 is a graph depicting reduced flow rate dependence of Formulation II using the RS01 versus the SPIRIVA (tiotropium bromide) HANDIHALER (dry powder inhaler) across a range of patient relevant inhalation pressure drops.

Formulation II was produced and filled into size 3 HPMC capsules for dispersion in the RS01 dry powder inhaler. SPIRIVA (tiotropium bromide) was procured and dispersed from the HANDIHALER (dry powder inhaler). Fine particle dose (FPD<5.0 microns) is shown at 1, 4, and 8 kPa pressure drops across the dry powder inhaler for Formulation II and SPIRIVA (tiotropium bromide) HANDIHALER (dry powder inhaler) as determined using an NGI. Fine particle dose was found to be less sensitive to flow rate for Formulation II compared to the SPIRIVA (tiotropium bromide) HANDIHALER (dry powder inhaler). The flow rate dependence of the fine particle dose (less than 5 micrometers) for both products is shown in FIG. 5 and Table 21 (n=3-5 replicates; values presented are the mean±standard deviation). Formulation II using the RS01 HR inhaler was found to be less sensitive to the patient's simulated inspiratory flow rate, even at the low DPI pressure drop of 1 kPa. These results indicate that Formulation II using the RS01 would provide both improved efficiency in delivery of the nominal dose compared to SPIRIVA (tiotropium bromide) HANDIHALER (dry powder inhaler) and more consistent lung delivery across the patient population, including those with low PIF due to highly compromised lungs.

TABLE 21

Flow rate dependence of Formulation II using the RS01 versus the SPIRIVA (tiotropium bromide) HANDIHALER (dry powder inhaler)

| DPI Pressure Drop (kPa) | FPD (<5.0 microns) in micrograms of Tiotropium | |
|---|---|---|
| | Formulation II using the RS01 HR inhaler at 5.8 µg nominal dose | SPIRIVA (tiotropium bromide) HANDIHALER (dry powder inhaler) at 18 µg nominal dose |
| 1 | 3.41 ± 0.13 | 1.61 ± 0.22 |
| 4 | 3.19 ± 0.17 | 2.70 ± 0.22 |
| 8 | 3.26 ± 0.06 | 2.85 ± 0.33 |

Note:
N = 3 replicates for both inhalers at all conditions, except that N = 5 for the RS01 at the 4 kPa condition.

Example 7. Pharmacokinetic (PK) and Pharmacodynamics (PD) Effects of Monovalent Cation-Based Dry Powders of Tiotropium Bromide (Formulations In a Phase Ib study, three dose strengths of a monovalent cation-based dry powder of tiotropium bromide, Formulations I-III, were evaluated. This study was designed to enroll up to 40 COPD patients in a randomized, double blind, 5-way single-dose crossover study. Formulations I-III, placebo, and open label comparator product were the 5 arms of the study. There was a 7 day minimum washout period between doses. Plasma levels of tiotropium bromide were measured over time (see FIG. 6 and Table 23) and the bronchodilatory effect was measured (FIG. 7). Subjects were moderate to severe COPD patients. Formulation I provides a nominal dose of 3 µg, Formulation II provides a nominal dose of 6 µg, and Formulation III provides a nominal dose of 9 µg, as indicated in Table 22.

TABLE 22

Formulations I-III, Placebo and SPIRIVA (tiotropium bromide) HANDIHALER (dry powder inhaler) loadings.

| Formulation | Composition (wt %) | | | Nominal Dose in 10 mg Fill Weight (µg tiotropium) |
|---|---|---|---|---|
| | Tiotropium Bromide | Leucine | Sodium Chloride | |
| I | 0.04 | 19.99 | 79.97 | 3 |
| II | 0.07 | 19.99 | 79.94 | 6 |
| III | 0.11 | 19.98 | 79.91 | 9 |
| Placebo | 0.00 | 20.00 | 80.00 | 0 |

TABLE 23

Serum PK values at Cmax and AUC values over varying timeframes.

| | 3 micrograms | 6 micrograms | 9 micrograms | SPIRIVA (tiotropium bromide) HANDIHALER (dry powder inhaler) |
|---|---|---|---|---|
| $C_{max}$ | 7.98 | 15.9 | 30.1 | 7.24 |
| $AUC_{0-2}$ | 4.79 | 10.1 | 17.6 | 6.65 |
| $AUC_{0-6}$ | 6.09 | 14.9 | 25.5 | 12.5 |
| $AUC_{0-24}$ | 6.38 | 18.1 | 36 | 18.2 |

Note:
All time points and Cmax are in pg/mL and the AUC is in pg * hr/mL

Serum levels of tiotropium bromide were determined using LC-MS/MS (Liquid chromatography-tandem mass spectrometry) methods well known in the art, e.g. as described in Nilsson et al. PLoS One, 5(7):e11411 (2010). The following analytes were detected (Table 24):

TABLE 24

Tiotropium analytes.

| Analyte | Precursor ion (m/z) | Product ion (m/z) |
|---|---|---|
| Tiotropium | 392.1 | 152.1 |
| Tiotropium-D3 | 395.2 | 155.2 |

Pulmonary function tests were performed using a standard calibrated spirometer. As a measure of the bronchodilatory effects of Formulations I-III in human subjects, $FEV_1$ (forced expiratory volume in one second) was used. The predicted $FEV_1$ was obtained using the normal prediction equations by the ERS (European Respiratory Society) adjusting for race, gender and age. Quanjer et al. "Lung volume and forced ventilatory flows." Eur Respir J. 6: Suppl. 16, 5-40 (1993). Spirometry measurements were conducted in accordance with ATS/ERS (American Thoracic Society/European Respiratory Society) 2005 guidelines. The single highest $FEV_1$ and the single highest FVC (forced vital capacity) values from acceptable and repeatable maneuvers were reported and the $FEV_1$/FVC ratio determined. Data is reported in FIG. 7.

Unaudited data obtained from the Phase Ib study suggest that tiotropium bromide, exemplified by Formulations I-III, was effectively delivered to the lungs in monovalent cation-based dry powders, and tiotropium bromide could be measured in the blood.

Figure 6:
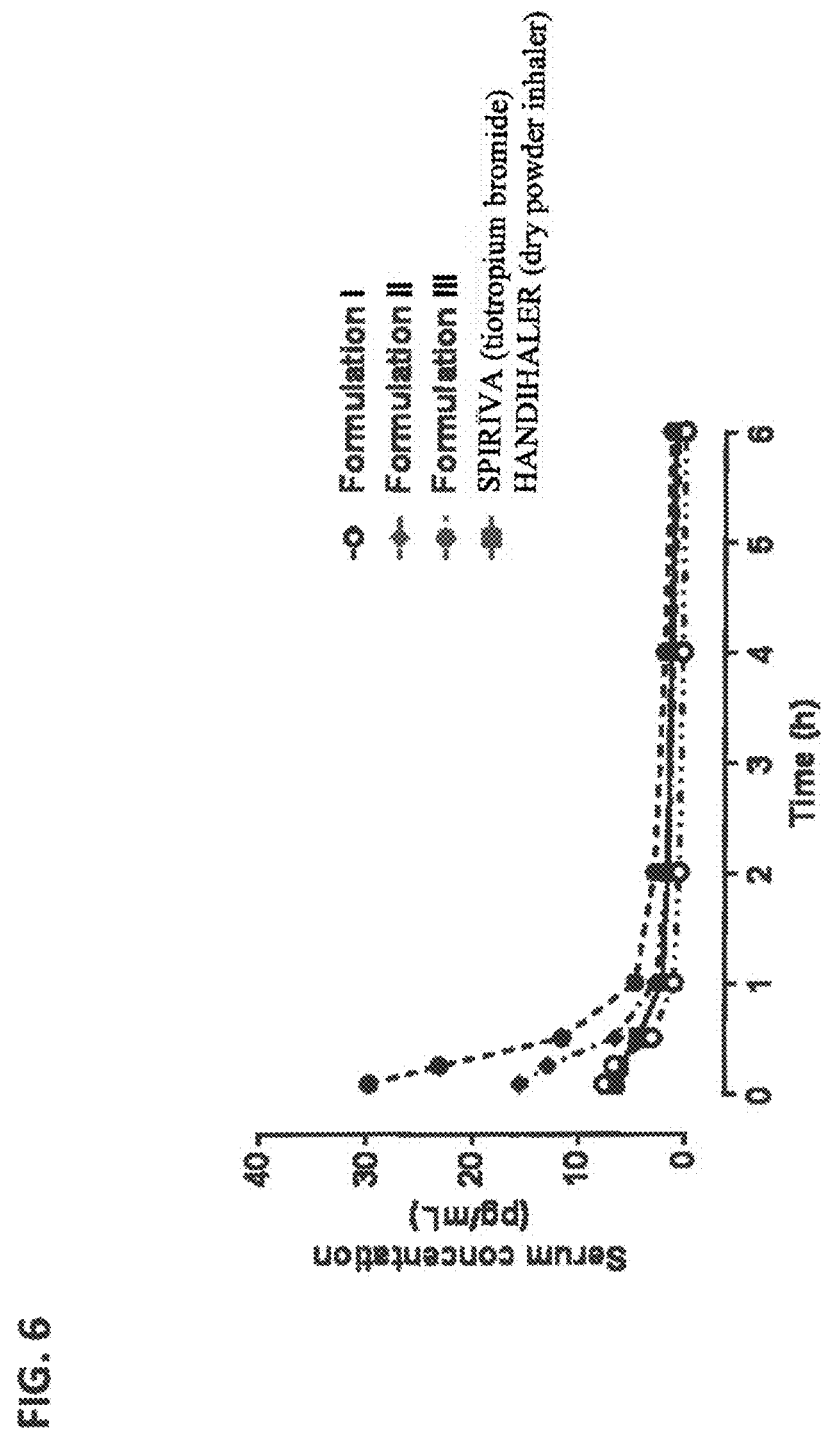
FIG. 6 is a graph depicting the geometric mean of plasma levels of tiotropium in pg/ml over time for exemplary Formulations I, II, III and SPIRIVA (tiotropium bromide) HANDIHALER (dry powder inhaler), respectively.
Figure 7:
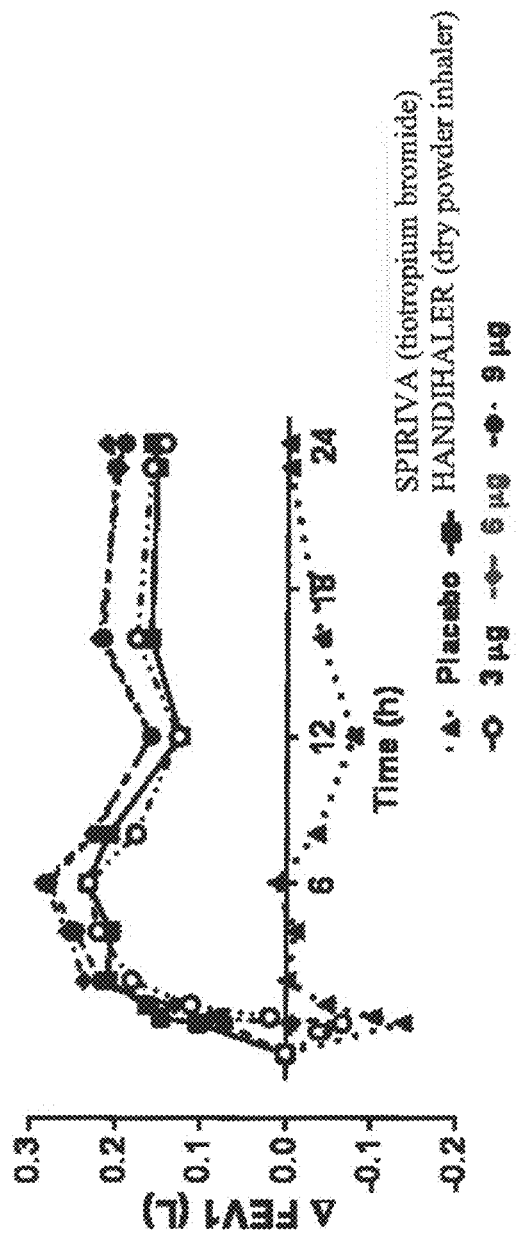
FIG. 7 is a graph depicting mean change in $FEV_1$ (forced expiratory volume in one second) from baseline over time for exemplary Formulations I (3 micrograms nominal dose, also called "3 μg"), II (6 micrograms nominal dose, also called "6 μg"), III (9 micrograms nominal dose, also called "9 μg"), SPIRIVA (tiotropium bromide) HANDIHALER (dry powder inhaler) and placebo.

FIG. 6 depicts the geometric mean PK profile of each nominal dose level (Formulations I-III, 3 µg, 6 µg, 9 µg, respectively), and the SPIRIVA (tiotropium bromide) HANDIHALER (dry powder inhaler) over a period of 6 hours. The maximal concentration for tiotropium ($C_{max}$) was detected at about 5 minutes after administration. SPIRIVA (tiotropium bromide) HANDIHALER (dry powder inhaler). Serum levels for Formulations I-III increased with dose and exhibited similar kinetics to the SPIRIVA (tiotropium bromide) HANDIHALER (dry powder inhaler). The $C_{max}$ and the $AUC_{0-2h}$ are similar between Formulation I and the SPIRIVA (tiotropium bromide) HANDIHALER (dry powder inhaler). $AUC_{0-24h}$ are similar between Formulation II and the SPIRIVA (tiotropium bromide) HANDIHALER (dry powder inhaler).

FIG. 7 depicts pharmacodynamic data that suggest that Formulations I-III all improved pulmonary function, each exerting a measurable bronchodilatory effect as measured by increased peak $FEV_1$ over the first 6 h after dosing and increased trough $FEV_1$ 24 h after dosing. Formulations I-III each resulted in a measurable and sustained increase in $FEV_1$, with the data showing significant and sustained increases in $FEV_1$ compared to the placebo. Formulation I matched the changes in $FEV_1$ to the SPIRIVA (tiotropium bromide) HANDIHALER (dry powder inhaler), both in "peak" and "trough" improvements. Formulations II and III result in a greater improvement in lung function than SPIRIVA (tiotropium bromide) HANDIHALER (dry powder inhaler).

This clinical data demonstrate the ability to match lung dose of SPIRIVA (tiotropium bromide) HANDIHALER (dry powder inhaler) with a significantly lower nominal dose. Formulation I is comparable to SPIRIVA (tiotropium bromide) HANDIHALER (dry powder inhaler) across multiple parameters and achieves a similar improvement in lung function to SPIRIVA (tiotropium bromide) HANDIHALER (dry powder inhaler) with significantly lower total systemic exposure. Formulation II, which has a similar total systemic exposure to SPIRIVA (tiotropium bromide) HANDIHALER (dry powder inhaler) as seen by $AUC_{0-24h}$ results in better lung function improvements at the same exposure dose.

A. Audited Clinical Data

As mentioned above in this example, the results presented were from unaudited data obtained from the Phase Ib study. Below is a presentation of the audited data from the same Phase Ib study as was presented earlier in this example, which support the observations and conclusions written above. The data above represent unaudited clinical data. It is noted that data in Tables 23 and 25 and FIG. 6 are geometric mean values, and data in Table 26 and FIG. 7 are mean values. It is noted that the SPIRIVA (tiotropium bromide) HANDIHALER (dry powder inhaler) was the comparator to Formulations I-III in the clinical trial. SPIRIVA (tiotropium bromide) HANDIHALER (dry powder inhaler) has a nominal dose of tiotropium of 18 micrograms, which is blended with 5.5 mg of lactose monohydrate, and has essentially a 5.5 mg capsule fill weight.

TABLE 25

Serum PK values at $C_{max}$ and AUC values (Values reported as geometric mean values. SD = Standard Deviation)

|  | Formulation I | Formulation II | Formulation III | SPIRIVA (tiotropium bromide) HANDIHALER (dry powder inhaler) |
|---|---|---|---|---|
| $C_{max}$ | 7.85 | 15.9 | 29.6 | 7.22 |
| SD | 6.84 | 13.4 | 18.9 | 6.85 |
| $AUC_{0-2\,h}$ | 4.70 | 9.08 | 15.8 | 6.56 |
| SD | 2.80 | 5.27 | 7.56 | 3.82 |
| $AUC_{0-6\,h}$ | 6.94 | 14.2 | 24.2 | 14.0 |
| SD | 4.19 | 7.15 | 10.8 | 6.69 |
| $AUC_{0-24\,h}$ | 8.77 | 21.2 | 38.0 | 24.7 |
| SD | 7.00 | 12.0 | 18.4 | 12.8 |

Note:
All time points and Cmax are in pg/mL and the AUC is in pg * hr/mL

Table 25 reports the audited clinical data for the serum PK values ($C_{max}$ and AUC) for different time periods up to 24 hours after dosing. The $C_{max}$ value of Formulation I was 7.85 pg/mL±6.84 pg/mL and closely matched that of SPIRIVA (tiotropium bromide) HANDIHALER (dry powder inhaler), which was 7.22 pg/mL±6.85 pg/mL. The $C_{max}$ values of Formulation II and III were 15.9 pg/mL±13.4 pg/mL and 29.6 pg/mL±18.9 pg/mL, respectively, which were both greater than $C_{max}$ of SPIRIVA (tiotropium bromide) HANDIHALER (dry powder inhaler). The $AUC_{0-24}$ of Formulation I was 8.77±7.00 pg*hr/mL, which was about ⅓ the $AUC_{0-24h}$ of SPIRIVA (tiotropium bromide) HANDIHALER (dry powder inhaler), which was 24.7±12.8 pg*hr/mL. This means that the systemic exposure of Formulation I was about ⅓ that of SPIRIVA (tiotropium bromide) HANDIHALER (dry powder inhaler). The $AUC_{0-24h}$ of Formulation II was 21.2±12.0 pg*hr/mL, which was about the same $AUC_{0-24h}$ of SPIRIVA (tiotropium bromide) HANDIHALER (dry powder inhaler), which was 24.7±12.8 pg*hr/mL. This means that the systemic exposure of Formulation II was about the same as that of SPIRIVA (tiotropium bromide) HANDIHALER (dry powder inhaler). The $AUC_{0-24h}$ of Formulation III was 38.0±18.4 pg*hr/mL, which was greater than the $AUC_{0-24h}$ of SPIRIVA (tiotropium bromide) HANDIHALER (dry powder inhaler) This means that the systemic exposure of Formulation III was greater than that of SPIRIVA (tiotropium bromide) HANDIHALER (dry powder inhaler).

The audited clinical data presented in Table 25 confirm the conclusions made from the unaudited data presented in Table 23 and FIG. 6.

TABLE 26

Absolute Value in $FEV_1$ and $FEV_1$ Change from Baseline at 6 hours and 24 hours after dosing. (Values reported as mean values. SD = Standard Deviation)

|  | Placebo | Formulation 1 (3 micrograms) | Formulation 2 (6 micrograms) | Formulation 2 (9 micrograms) | SPIRIVA (tiotropium bromide) HANDIHALER (dry powder inhaler) |
|---|---|---|---|---|---|
| Pre-dose $FEV_1$ (t = 0 hours) (L) | 1.297 | 1.321 | 1.282 | 1.296 | 1.288 |
| SD | 0.366 | 0.370 | 0.369 | 0.348 | 0.373 |
| Absolute $FEV_1$ (t = 6 hours) (L) | 1.311 | 1.561 | 1.577 | 1.588 | 1.529 |
| SD | 0.373 | 0.445 | 0.443 | 0.419 | 0.437 |
| Change in $FEV_1$ at t = 6 hours (L) | 0.014 | 0.239 | 0.294 | 0.292 | 0.240 |

TABLE 26-continued

Absolute Value in FEV$_1$ and FEV$_1$ Change from Baseline at 6 hours and 24 hours after dosing. (Values reported as mean values. SD = Standard Deviation)

| | Placebo | Formulation 1 (3 micrograms) | Formulation 2 (6 micrograms) | Formulation 2 (9 micrograms) | SPIRIVA (tiotropium bromide) HANDIHALER (dry powder inhaler) |
|---|---|---|---|---|---|
| SD | 0.112 | 0.163 | 0.166 | 0.168 | 0.189 |
| Absolute FEV$_1$ at Trough (t = 24 hours) (L) | 1.299 | 1.472 | 1.500 | 1.494 | 1.458 |
| SD | 0.366 | 0.392 | 0.421 | 0.387 | 0.357 |
| Change in FEV$_1$ at Trough (t = 24 hours) (L) | 0.001 | 0.151 | 0.218 | 0.198 | 0.169 |
| SD | 0.100 | 0.120 | 0.145 | 0.164 | 0.157 |

Table 26 reports the audited clinical data for the FEV$_1$ values over varying time-points up to 24 hours. At the 6 hour time point, administration of Formulation I had caused a change in FEV$_1$ of 0.239 L±0.163 L which closely matched the result observed for SPIRIVA (tiotropium bromide) HANDIHALER (dry powder inhaler), which had caused a change in FEV$_1$ of 0.240 L±0.189 L, indicating a similar lung function improvement at 6 hours. Formulations II and III had caused a change in FEV$_1$ of 0.294 L±0.166 L and 0.292 L±0.168 L, respectively, both of which are greater than the change in FEV1 of 0.240 L±0.189 L observed for SPIRIVA (tiotropium bromide) HANDIHALER (dry powder inhaler), indicating a greater lung function improvement at 6 hours. At the 24 hours time point, which was the trough FEV$_1$ observation point, administration of Formulation I had caused a change in FEV$_1$ of 0.151 L±0.120 L which was slightly less than the result observed for SPIRIVA (tiotropium bromide) HANDIHALER (dry powder inhaler), which had caused a change in FEV$_1$ of 0.169 L±0.157 L, indicating that Formulation I caused an improvement in lung function at 24 hours, but was slightly less than observed for SPIRIVA (tiotropium bromide) HANDIHALER (dry powder inhaler). Formulations II and III had caused a change in FEV$_1$ of 0.218 L±0.145 L and 0.198 L±0.164 L, respectively, both of which are greater than the change in FEV1 of 0.169 L±0.157 L observed for SPIRIVA (tiotropium bromide) HANDIHALER (dry powder inhaler), indicating a greater improvement in lung function at 24 hours.

The audited clinical data presented in Table 26 confirm the conclusions made from the unaudited data presented in FIG. 7.

Both the unaudited and audited data obtained from the Phase Ib study suggest that tiotropium bromide, exemplified by Formulations I-III, was effectively delivered to the lungs in monovalent cation-based dry powders, and that tiotropium bromide could be measured in the blood. The audited clinical data closely matched the unaudited clinical data and served to confirm the conclusions drawn from the unaudited data.

These clinical data demonstrate the ability to match lung dose of SPIRIVA (tiotropium bromide) HANDIHALER (dry powder inhaler) with a significantly lower nominal dose. Formulation I was comparable to SPIRIVA (tiotropium bromide) HANDIHALER (dry powder inhaler) in lung function improvement over the 24 hour time period, SPIRIVA (tiotropium bromide) HANDIHALER (dry powder inhaler) as demonstrated by the similar improvements in FEV$_1$ at the 6 hour timepoint and 24 hour trough timepoint. This similar lung function improvement was achieved with similar values for $C_{max}$, yet with a significantly lower total systemic exposure, as seen by $AUC_{0-24h}$ results of about ⅓ that observed for SPIRIVA (tiotropium bromide) HANDIHALER (dry powder inhaler). Formulation II, which has a similar total systemic exposure to SPIRIVA (tiotropium bromide) HANDIHALER (dry powder inhaler) as seen by $AUC_{0-24h}$ results in better lung function improvements at the same exposure dose, for example, FEV$_1$ change at 6 hours and at the 24 hour trough timepoint.

Example 8. An In Vitro Testing Comparing the Aerodynamic Particle Sizes of Tiotropium Bromide Formulation II from the RS01 UHR2 to the SPIRIVA (Tiotropium Bromide) HANDIHALER (Dry Powder Inhaler)

The example above was substantially repeated, as described in Example 6, with a different model of dry powder inhaler delivering Formulation II. In Example 6, Formulation II was delivered using the RS01 HR dry powder inhaler while in the current example, Formulation II was delivered from the RS01 UHR2 dry powder inhaler which has a higher resistance to airflow than the RS01 HR model. In vitro aerodynamic particle size distribution (aPSD) testing was performed which compared Formulation II delivered form the RS01 UHR2 dry powder inhaler to the SPIRIVA (tiotropium bromide) HANDIHALER (dry powder inhaler). The goals of this study were i) to inform the development of a formulation that achieved similar fine particle dose delivery across a range of flow rates relevant for COPD patients and ii) to determine if Formulation II, representative of all the Formulations I-IV, was less dependent on a patient's inspiratory flow rate than the SPIRIVA (tiotropium bromide) HANDIHALER (dry powder inhaler). This aPSD testing was performed across a range of flow rates relevant to the intended COPD patient population.

Figure 8:
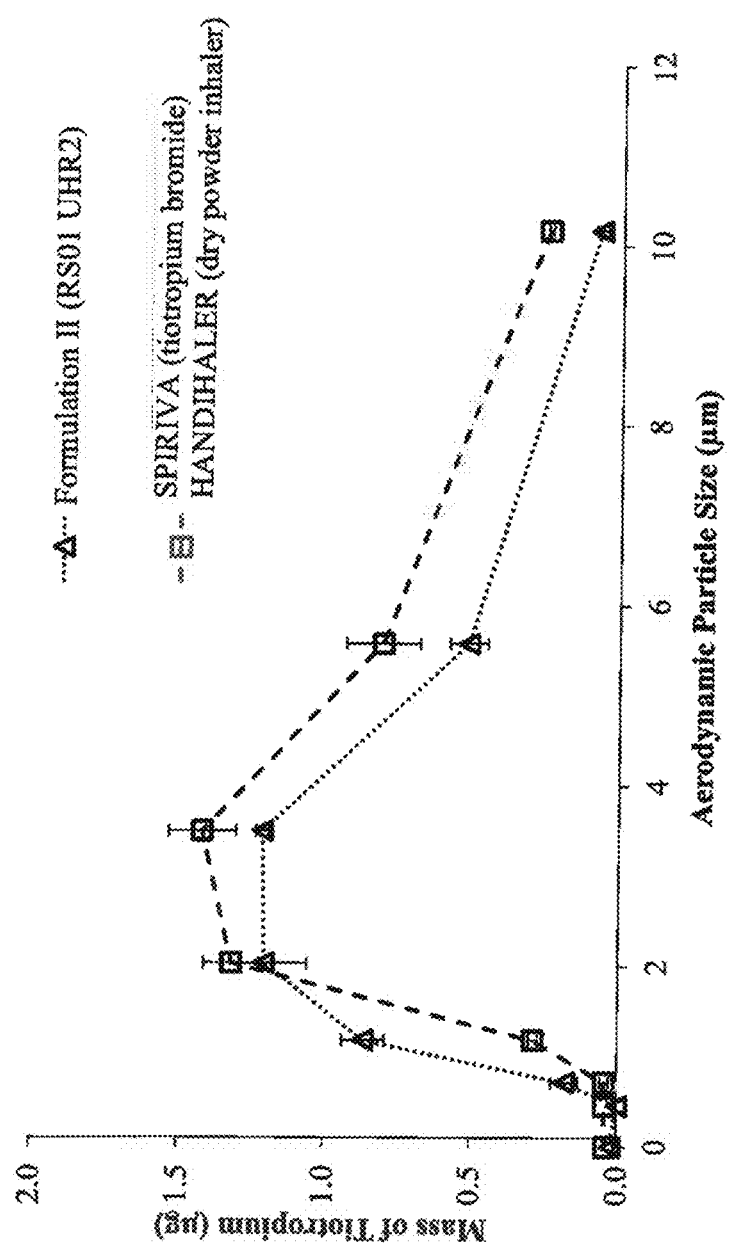
FIG. 8 is a graph of the aerodynamic size distributions at 4 kPA pressure drop for Formulation II delivered from the RS01 UHR2 at a 5.8 μg nominal dose and SPIRIVA (tiotropium bromide) HANDIHALER (dry powder inhaler) at a 18 μg nominal dose, illustrating a similar fine particle dose (FPD) for Formulation II with a reduced nominal drug loading.
Figure 9:
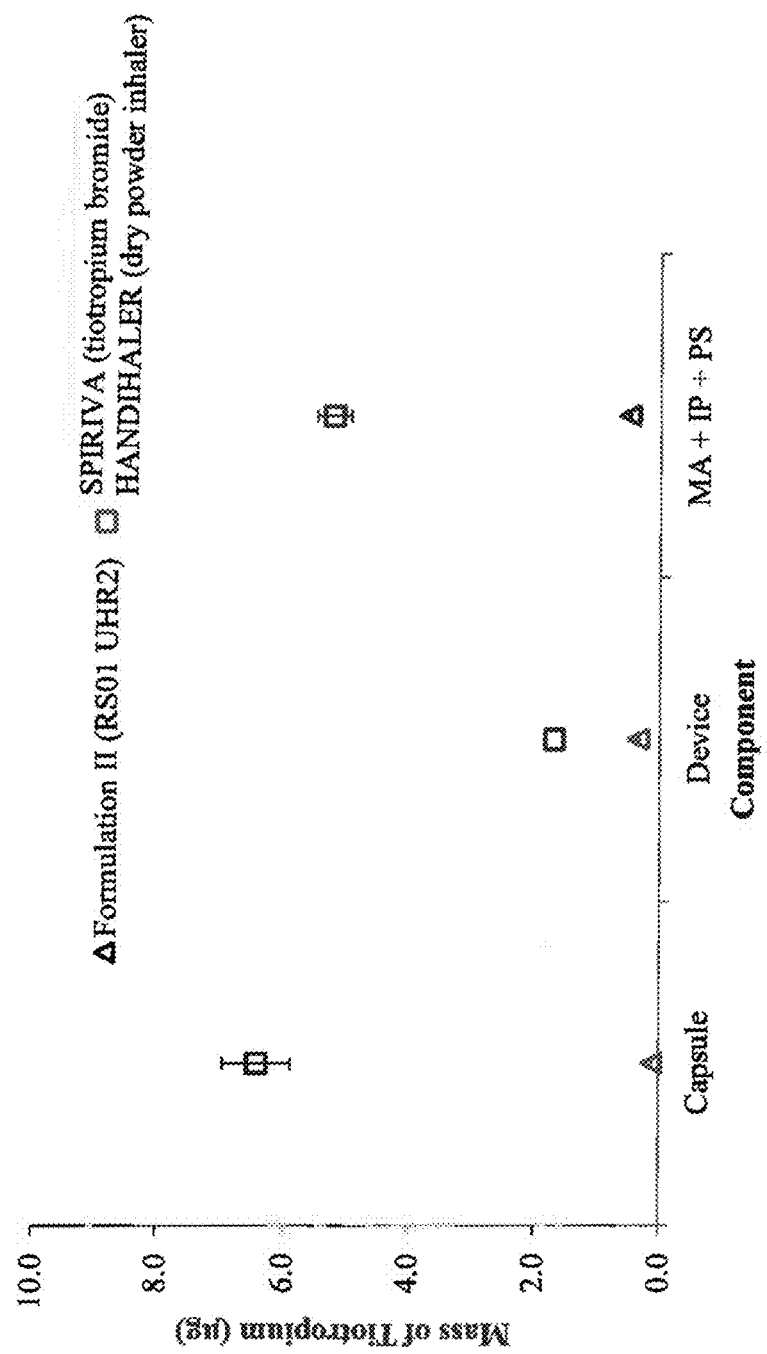
FIG. 9 is a graph showing that Formulation II delivered from the RS01 UHR2 has minimal oral deposition versus the SPIRIVA (tiotropium bromide) HANDIHALER (dry powder inhaler), reducing potential side effects.

Formulation II was produced and filled into size 3 HPMC capsules for dispersion in the RS01 UHR2 dry powder inhaler. SPIRIVA (tiotropium bromide) was procured and dispersed from the HANDIHALER (dry powder inhaler). A multi-stage next-generation impactor (NGI) was used to determine the mass median aerodynamic diameters, the fine particle fraction (FPF) less than 5 micrometers in diameter, and the fine particle dose (FPD) less than 5 micrometers in diameter. As both the RS01 UHR2 and SPIRIVA (tiotropium bromide) HANDIHALER (dry powder inhaler) dry powder inhaler have the similar airflow resistances, the formulations were compared at the same air flow rates and so similar pressure drops across the inhaler. The particle size distributions are shown at a 4 kPa pressure drop across each dry powder inhaler, which corresponds to 39 LPM through each dry powder inhaler. (See FIG. 8 and Table 27 below) Testing was performed with replicates, n=3 for the Formulation II using the RS01 UHR2 inhaler and n=3 for SPIRIVA (tiotropium bromide) HANDIHALER (dry powder inhaler). Similar aerodynamic particle size distributions are seen for the 3 products and the fine particle dose (FPD<5.0 µm) was found to be comparable for Formulation II using the RS01 inhaler and the SPIRIVA (tiotropium bromide) HANDIHALER (dry powder inhaler), even though the nominal dose of Formulation II was 5.8 micrograms and the nominal dose of SPIRIVA (tiotropium bromide) HANDIHALER (dry powder inhaler) was 18 micrograms. This means that the delivery efficiency for Formulation II using the RS01 UHR2 inhaler was over three times more efficient that the SPIRIVA (tiotropium bromide) HANDIHALER (dry powder inhaler). This result is further illustrated by the difference in the fine particle fraction (FPF<5.0 µm) relative to the nominal dose, which was 51.4% for Formulation II in the RS01 UHR2 and 15.0% for SPIRIVA (tiotropium bromide) HANDIHALER (dry powder inhaler). (See Table 28 below.) The loss of drug product for the SPIRIVA (tiotropium bromide) HANDIHALER (dry powder inhaler) was attributed to the relatively higher amounts of the therapeutic left in the capsule, device, mouthpiece adapter, induction port and pre-separator. (See FIG. 9 and Table 29 below) A pre-separator was not included in NGI testing with Formulation II with the RS01 UHR2 inhaler because carrier particles were not present in the spray-dried formulation.

TABLE 27

Tiotropium mass distribution by stage of the NGI at 4 kPa for Formulation II using the RS01 UHR2 inhaler per 5.8 µg tiotropium nominal dose and the SPIRIVA (tiotropium bromide) HANDIHALER (dry powder inhaler) per 18 µg nominal dose.

| Tiotropium mass distribution by stage of the NGI | Formulation II using the RS01 UHR2 inhaler at 39 LPM and 5.8 µg nominal dose (µg tiotropium) | SPIRIVA (tiotropium bromide) HANDIHALER (dry powder inhaler) at 39 LPM and 18 µg nominal dose (µg tiotropium) |
|---|---|---|
| Stage 1 | 0.07 ± 0.02 | 0.25 ± 0.01 |
| Stage 2 | 0.51 ± 0.06 | 0.81 ± 0.13 |
| Stage 3 | 1.21 ± 0.02 | 1.42 ± 0.11 |
| Stage 4 | 1.21 ± 0.15 | 1.32 ± 0.10 |
| Stage 5 | 0.87 ± 0.07 | 0.29 ± 0.02 |
| Stage 6 | 0.18 ± 0.05 | 0.04 ± 0.01 |
| Stage 7 | 0 | 0.04 |
| Micro-Orifice Collector | 0.02 | 0.04 |
| After Filter | 0 | 0.02 |

TABLE 28

Tiotropium nominal dose and FPF less than 5.0 microns as a percentage of the nominal dose using the RS01 UHR2 inhaler and the SPIRIVA (tiotropium bromide) HANDIHALER (dry powder inhaler).

| | Formulation II using the RS01 UHR2 inhaler | SPIRIVA (tiotropium bromide) HANDIHALER (dry powder inhaler) |
|---|---|---|
| Nominal Dose (µg tiotropium) | 5.8 | 18 |
| FPF (<5.0 microns) as a percentage of the Nominal Dose | 54.1 ± 3.3 | 15.0 ± 1.2 |

TABLE 29

Tiotropium mass distribution on various components before entering the NGI at 4 kPa for Formulation II using the RS01 UHR2 inhaler and the SPIRIVA (tiotropium bromide) HANDIHALER (dry powder inhaler).

| Powder distribution on various components before entering the NGI | Formulation II using the RS01 UHR2 inhaler at 39 LPM and 5.8 µg nominal dose (µg tiotropium) | SPIRIVA (tiotropium bromide) HANDIHALER (dry powder inhaler) at 39 LPM and 18 µg nominal dose (µg tiotropium) |
|---|---|---|
| Capsule | 0.12 ± 0.00 | 6.42 ± 0.53 |
| Dry Powder Inhaler | 0.34 ± 0.02 | 1.68 |
| Mouthpiece Adapter, Induction Port and Pre-separator | 0.50 ± 0.02 | 5.23 0.27 |

Aerosol testing was performed over a range of peak inspiratory flows (PIF) relevant to the intended COPD patient population. A flow rate range 20 L/min to 55 L/min, with a mid-point of 39 L/min (corresponding to 1, 4 and 8 kPa) was selected for testing SPIRIVA (tiotropium bromide) HANDIHALER (dry powder inhaler) and Formulation II from the RS01 UHR2, which spans the PIF range that was measured for COPD patients with the product and is specified in the United States product package insert for SPIRIVA (tiotropium bromide) HANDIHALER (dry powder inhaler).

Formulation II was produced and filled into size 3 HPMC capsules for dispersion in the RS01 UHR2 dry powder inhaler. SPIRIVA (tiotropium bromide) was procured and dispersed from the HANDIHALER (dry powder inhaler). Fine particle dose (FPD<5.0 microns) is shown at 1, 4, and 8 kPa pressure drops across the dry powder inhaler for Formulation II from both RS01 inhalers and SPIRIVA (tiotropium bromide) HANDIHALER (dry powder inhaler) as determined using an NGI. Fine particle dose was found to be less sensitive to flow rate for Formulation II in the RS01 UHR2 inhaler compared to the SPIRIVA (tiotropium bromide) HANDIHALER (dry powder inhaler). The flow rate dependence of the fine particle dose (less than 5 micrometers) for both products is shown in FIG. 10 and Table 30 (n=3 replicates; values presented are the mean±standard deviation). Formulation II using the RS01 UHR2 inhaler was found to be less sensitive to the patient's simulated inspiratory flow rate, even at the low DPI pressure drop of 1 kPa. These results indicate that Formulation II using the RS01 UHR2 inhaler would provide both improved efficiency in delivery of the nominal dose compared to SPIRIVA (tiotropium bromide) HANDIHALER (dry powder inhaler) and more consistent lung delivery across the patient population, including those with low PIF due to highly compromised lungs.

TABLE 30

Flow rate dependence of Formulation II using the RS01 UHR2 versus the SPIRIVA (tiotropium bromide) HANDIHALER (dry powder inhaler)

| DPI Pressure Drop (kPa) | FPD (<5.0 microns) in micrograms of Tiotropium | |
|---|---|---|
| | Formulation II using the RS01 UHR2 inhaler at 5.8 μg nominal dose | SPIRIVA (tiotropium bromide) HANDIHALER (dry powder inhaler) at 18 μg nominal dose |
| 1 | 3.14 ± 0.07 | 1.61 ± 0.22 |
| 4 | 3.15 ± 0.19 | 2.70 ± 0.22 |
| 8 | 3.24 ± 0.20 | 2.85 ± 0.33 |

What is claimed is:

1. A receptacle comprising a respirable dry powder consisting of homogenous respirable dry particles that comprise sodium chloride, leucine, and tiotropium bromide, wherein the sodium chloride is 67% to 84% by weight, the leucine is 12% to 28% by weight, the tiotropium bromide is about 0.01% to about 0.5% by weight, and optionally one or more additional therapeutic agents up to about 20% by weight, wherein all percentages are weight percentages on a dry basis and all the components of the respirable dry particles amount to 100%, wherein the receptacle contains a nominal dose of tiotropium between about 1.5 to about 12 micrograms.

2. The receptacle of claim 1, wherein the receptacle is a capsule or a blister, and wherein the receptacle contains about 15 mg of dry powder or less.

3. The receptacle of claim 1, wherein the receptacle contains a nominal dose of tiotropium between about 3 to about 12 micrograms.

4. The receptacle of claim 1, wherein the receptacle contains a nominal dose of tiotropium between about 3 to about 9 micrograms.

5. The receptacle of claim 1, wherein the receptacle contains a nominal dose of tiotropium between about 3 to about 6 micrograms.

6. The receptacle of claim 1, wherein the respirable dry powder has a fine particle dose less than 5.0 microns of between about 1 microgram and about 5 micrograms of tiotropium.

7. The receptacle of claim 1, wherein the respirable dry powder has a fine particle dose less than 4.4 microns of between about 1 microgram and about 4 micrograms of tiotropium.

8. The receptacle of claim 1, wherein the respirable dry powder has a fine particle dose less than 4.4 microns of between about 1.5 micrograms and about 3.5 micrograms of tiotropium.

9. The receptacle of claim 1, wherein the receptacle is a capsule, and wherein the capsule contains less than 6 mg of dry powder.

10. The receptacle of claim 1, wherein the sodium chloride is about 79.5% to about 80.5% by weight and the leucine is about 19.5% to about 20.5% by weight.

11. The receptacle of claim 1, wherein the respirable dry particles have a volume median geometric diameter (VMGD) of about 5 micrometers or less.

12. The receptacle of claim 1, wherein the respirable dry powder has a mass median aerodynamic diameter (MMAD) of between about 1 micron and about 5 microns.

13. The receptacle of claim 1, wherein the respirable dry particles have a 1/4 bar dispersibility ratio (1/4 bar) of less than 1.5 as measured by laser diffraction.

14. The receptacle of claim 1, wherein the respirable dry particles have a tap density greater than 0.4 g/cc to about 1.2 $g/cm^3$.

15. The receptacle of claim 1, wherein the one or more additional therapeutic agent is one or more corticosteroids.

16. A receptacle comprising a respirable dry powder consisting of homogenous respirable dry particles that comprise sodium chloride, leucine, and tiotropium bromide, wherein the sodium chloride is 67% to 84% by weight, the leucine is 12% to 28% by weight, the tiotropium bromide is about 0.01% to about 0.5% by weight, and optionally one or more additional therapeutic agents up to about 20% by weight, wherein all percentages are weight percentages on a dry basis and all the components of the respirable dry particles amount to 100%, wherein the receptacle contains a nominal dose of tiotropium between about 0.5 to about 6 micrograms.

17. The receptacle of claim 16, wherein the receptacle contains a nominal dose of tiotropium between about 0.5 microgram to about 3 micrograms.

18. The receptacle of claim 16, wherein the respirable dry powder has a fine particle dose less than 5.0 microns of between about 1 microgram and about 5 micrograms of tiotropium.

19. The receptacle of claim 1, wherein the respirable dry powder has a fine particle dose less than 4.4 microns of between about 1.5 micrograms and about 3.5 micrograms of tiotropium.

20. A method for treating a respiratory disease selected from the group consisting of COPD, chronic bronchitis, emphysema, asthma, cystic fibrosis, or non-cystic fibrosis bronchiectasis, comprising administering to the respiratory tract of a patient in need thereof an effective amount of a respirable dry powder of claim 1.

21. A method for treating or reducing the incidence or severity of an acute exacerbation of a respiratory disease selected from the group consisting of COPD, chronic bronchitis, emphysema, asthma, cystic fibrosis, or non-cystic fibrosis bronchiectasis, comprising administering to the respiratory tract of a patient in need thereof an effective amount of a respirable dry powder of claim 1.

22. The method of claim 20, wherein the respiratory disease is COPD.

23. A dry powder inhaler that contains the receptacle of claim 1, wherein the dry powder inhaler is a capsule-based dry powder inhaler or a blister-based dry powder inhaler.

* * * * *